United States Patent
Lee et al.

(10) Patent No.: US 9,453,261 B2
(45) Date of Patent: Sep. 27, 2016

(54) ALTERNATIVE SPLICING VARIANTS OF GENES ASSOCIATED WITH PROSTATE CANCER RISK AND SURVIVAL

(71) Applicant: The George Washington University, Washington, DC (US)

(72) Inventors: Norman H. Lee, Dayton, MD (US); Steven R. Patierno, Chapel Hill, NC (US); Bi-Dar Wang, Potomac, MD (US)

(73) Assignee: The George Washington University, Washington, DC (US)

( * ) Notice: Subject to any disclaimer, the term of this patent is extended or adjusted under 35 U.S.C. 154(b) by 0 days.

(21) Appl. No.: 14/344,509

(22) PCT Filed: Sep. 20, 2012

(86) PCT No.: PCT/US2012/056346
§ 371 (c)(1),
(2) Date: Mar. 12, 2014

(87) PCT Pub. No.: WO2013/043878
PCT Pub. Date: Mar. 28, 2013

(65) Prior Publication Data
US 2014/0364483 A1 Dec. 11, 2014

Related U.S. Application Data

(60) Provisional application No. 61/536,957, filed on Sep. 20, 2011.

(51) Int. Cl.
| | | |
|---|---|---|
| C07H 21/04 | (2006.01) | |
| C12Q 1/68 | (2006.01) | |
| C07K 14/47 | (2006.01) | |
| C12N 15/113 | (2010.01) | |

(52) U.S. Cl.
CPC ............ *C12Q 1/6886* (2013.01); *C07K 14/47* (2013.01); *C07K 14/4748* (2013.01); *C12N 15/1137* (2013.01); *C12Q 2600/118* (2013.01); *C12Q 2600/156* (2013.01)

(58) Field of Classification Search
CPC ............................ C12N 5/111; C12N 15/113
See application file for complete search history.

(56) References Cited

U.S. PATENT DOCUMENTS

| | | |
|---|---|---|
| 4,683,195 A | 7/1987 | Mullis et al. |
| 4,683,203 A | 7/1987 | Anton et al. |
| 6,333,155 B1 | 12/2001 | Lockhart et al. |
| 7,691,997 B2 * | 4/2010 | Khvorova ............ A61K 31/713 536/24.5 |
| 8,008,474 B2 | 8/2011 | Khvorova et al. |
| 2004/0266780 A1 | 12/2004 | Sadhu et al. |
| 2006/0159681 A1 | 7/2006 | Lozano et al. |
| 2006/0189557 A1 | 8/2006 | Slack et al. |
| 2006/0269971 A1 | 11/2006 | Diamandis |
| 2008/0234941 A1 | 9/2008 | Jackson et al. |
| 2010/0105134 A1 | 4/2010 | Quay et al. |
| 2011/0136123 A1 | 6/2011 | Klinck et al. |
| 2011/0152346 A1 | 6/2011 | Karleson et al. |
| 2011/0207713 A1 | 8/2011 | Castanedo et al. |

FOREIGN PATENT DOCUMENTS

WO WO 2008109375 A2 * 9/2008 ........... C12N 15/113

OTHER PUBLICATIONS

H. Caren et al., "Genetic and Epigenetic Changes in the Common I p36 Deletion in Neuroblastoma Tumours," British Journal of Cancer, 2007, vol. 97. pp. 1416-1424.
Y. Tian et al., "Differences in Exon Expression and Alternatively Spliced Genes in Blood of Multiple Sclerosis Compared to Healthy Control Subjects," Journal of Neuroimmunology, vol. 230, 2011, pp. 124-129.
"Exon Probeset Annotations and Transcript Cluster Groupins"; Revision Date: Sep. 27, 2005; Revision Version 1 0: pp. 1-11; Exon Array Whitepaper Collection. Affymetrix GeneChip.
H. Bollers, MD, et al. "Current Protocols in Molecular Biology", Molecular Biology, Mar. 3, 1989: vol. 261: No. 9: pp. 1348: John Wily & Sons, Inc., New York.
S.L. Beaucage et al., "Deoxynucleoside Phosphoramadites—A New Class of Key Intermediates for Deoxypolynucleotide Synthesis", Tetrahedron Letters. 1981, vol. 22, No. 20, pp. 1859-1862, Pergamon Press Ltd., Great Britain.
Anice E. Thigpen, et al., "Molecular Genetics of Steroid 5α-Reductase 2 Deficiency", J. Clin. Invest. Sep. 1992, vol. 90, pp. 799-809. The American Society for Clinical Investigation, Inc.
R. K. Saiki, et al.: "Primer-Directed Enzymatic Amplification of DNA with Thermostable DNA Polymerase"; Science New Series, Jan. 29, 1988, vol. 239, No. 4839, pp. 487-491; American Association for the Advancement of Science.
H. Caren et al., "Genetic and Epigenetic Changes in the Common I p36 Deletion in Neuroblastoma Tumours," British Journal of Cancer. 2007, vol. 97, pp 1416-1424.
Novel Finding of P110 Delta and Btk Genesin the Etiology of Primary B-Cell Immunodeficiency, NTU Institution Repository Document NSC91-2314-13-002-189, Jul. 26, 2006, pp. 1-11.
International Search Report and Written Opinion issued on Mar. 8, 2013, in International Patent Application No. PCT/US2012/056346, 20 pages.

* cited by examiner

*Primary Examiner* — Amy Bowman
(74) *Attorney, Agent, or Firm* — Blank Rome, LLP

(57) ABSTRACT

Disclosed are novel splicing variants of the genes associated with prostate cancer risk and survival, particularly splicing variants of PIK3CD, FGFR3, TSC2, RASGRP2, ITGA4, MET, NF1 and BAK1. The disclosure also relates risk assessment, detection, diagnosis, or prognosis of prostate cancer. More specifically, this disclosure relates to the detection of certain splicing variants of PIK3CD, FGFR3, TSC2, RASGRP2, ITGA4, MET, NF1 and BAK1.

8 Claims, 10 Drawing Sheets

SEQUENCE LISTING

<160> NUMBER OF SEQ ID NOS: 87

<210> SEQ ID NO 1
<211> LENGTH: 3135
<212> TYPE: DNA

<213> ORGANISM: Homo sapiens

<400> SEQUENCE: 1

```
atgcccctg gggtggactg ccccatggaa ttctggacca aggaggagaa tcagagcgtt      60
gtggttgact tcctgctgcc cacaggggtc tacctgaact tccctgtgtc ccgcaatgcc    120
aacctcagca ccatcaagca gctgctgtgg caccgcgccc agtatgagcc gctcttccac    180
atgctcagtg gccccgaggc ctatgtgttc acctgcatca accagacagc ggagcagcaa    240
gagctggagg acgagcaacg cgtctgtgt gacgtgcagc ccttcctgcc cgtcctgcgc    300
ctggtggccc gtgagggcga ccgcgtgaag aagctcatca actcacagat cagcctcctc    360
atcggcaaag gcctccacga gtttgactcc ttgtgcgacc cagaagtgaa cgactttcgc    420
gccaagatgt gccaattctg cgaggaggcg gccgcccgcc ggcagcagct gggctgggag    480
gcctggctgc agtacagttt ccccctgcag ctggagccct cggctcaaac ctgggggcct    540
ggtaccctgc ggctcccgaa ccgggcccct ctggtcaacg ttaagtttga gggcagcgag    600
gagagcttca ccttccaggt gtccaccaag acgtgccgc tggcgctgat ggcctgtgcc    660
ctgcggaaga aggccacagt gttccggcag ccgctggtgg agcagccgga agactacacg    720
ctgcaggtga acgcaggca tgagtacctg tatggcagct cccgctctg ccagttccag    780
tacatctgca gctgcctgca cagtgggttg acccctcacc tgaccatggt ccattcctcc    840
tccatcctcg ccatgcggga tgagcagagc aaccctgccc ccaggtcca gaaaccgcgt    900
gccaaaccac ctcccattcc tgcgaagaag ccttcctctg tgtccctgtg gtccctggag    960
cagccgttcc gcatcgagct catccagggc agcaaagtga acgccgacga gcggatgaag   1020
ctggtggtgc aggccgggct ttccacggc aacgagatgc tgtgcaagac ggtgtccagc   1080
tcggaggtga gcgtgtgctc ggagcccgtg tggaagcagc ggctggagtt cgacatcaac   1140
atctgcgacc tgccccgcat ggcccgtctc tgctttgcgc tgtacgccgt gatcgagaaa   1200
gccaagaagg ctcgctccac caagaagaag tccaagaagg cggactgccc cattgcctgg   1260
gccaacctca tgctgtttga ctacaaggac cagcttaaga ccggggaacg ctgcctctac   1320
atgtggccct ccgtcccaga tgagaaggc gagctgctga ccccacggg cactgtgcgc   1380
agtaacccca acacggatag cgccgctgcc ctgctcatct gcctgcccga ggtggccccg   1440
caccccgtgt actaccccgc cctggagaag atcttggagc tggggcgaca cagcgagtgt   1500
gtgcatgtca ccgaggagga gcagctgcag ctgcgggaaa tcctggagcg cggggggtct   1560
ggggagctgt atgagcacga aaggacctg tgtggaagc tgcggcatga agtccaggag   1620
cacttcccgg aggcgctagc ccggctgctg ctggtcacca agtggaacaa gcatgaggat   1680
gtggcccaga tgctctacct gctgtgctcc tggccggagc tgccgtcct gagcgccctg   1740
gagctgctag acttcagctt ccccgattgc cacgtaggct ccttcgccat caagtcgctg   1800
cggaaactga cggacgatga gctgttccag tacctgctgc agctggtgca ggtgctcaag   1860
tacgagtcct acctggactg cgagctgacc aaattcctgc tggaccgggc cctggccaac   1920
cgcaagatcg ccacttcct tttctggcac ctccgctccg agatgcacgt gccgtcggtg   1980
gccctgcgct tcggcctcat cctggaggcc tactgcaggg gcagcaccca ccacatgaag   2040
gtgctgatga agcagggga agcactgagc aaactgaagg ccctgaatga cttcgtcaag   2100
ctgagctctc agaagacccc caagcccag accaaggagc tgatgcactt gtgcatgcgg   2160
caggaggcct acctagaggc cctctcccac ctgcagtccc cactcgaccc cagcaccctg   2220
ctggctgaag tctgcgtgga gcagtgcacc ttcatggact ccaagatgaa gccctgtgg   2280
```

```
atcatgtaca gcaacgagga ggcaggcagc ggcggcagcg tgggcatcat ctttaagaac    2340
ggggatgacc tccggcagga catgctgacc ctgcagatga tccagctcat ggacgtcctg    2400
tggaagcagg aggggctgga cctgaggatg accccctatg gctgcctccc caccggggac    2460
cgcacaggcc tcattgaggt ggtactccgt tcagacacca tcgccaacat ccaactcaac    2520
aagagcaaca tggcagccac agccgccttc aacaaggatg ccctgctcaa ctggctgaag    2580
tccaagaacc cggggggaggc cctggatcga gccattgagg agttcacccct ctcctgtgct    2640 ggctattgtg tggccacata tgtgctgggc attggcgatc ggcacagcga caacatcatg    2700
atccgagaga gtgggcagct gttccacatt gattttggcc actttctggg gaatttcaag    2760
accaagtttg gaatcaaccg cgagcgtgtc ccattcatcc tcacctacga ctttgtccat    2820
gtgattcagc aggggaagac taataatagt gagaaatttg aacggttccg gggctactgt    2880
gaaagggcct acaccatcct gcggcgccac gggcttctct tcctccacct ctttgccctg    2940
atgcgggcgg caggcctgcc tgagctcagc tgctccaaag acatccagta tctcaaggac    3000
tccctggcac tggggaaaac agaggaggag gcactgaagc acttccgagt gaagtttaac    3060
gaagccctcc gtgagagctg gaaaaccaaa gtgaactggc tggcccacaa cgtgtccaaa    3120
gacaacaggc agtag                                                      3135
```

<210> SEQ ID NO 2
<211> LENGTH: 21
<212> TYPE: DNA
<213> ORGANISM: Artificial Sequence
<220> FEATURE:
<223> OTHER INFORMATION: Primers for qRT-PCR validations of PI3KCD
      splice variants

<400> SEQUENCE: 2
caaactgaag gccctgaatg a                                              21

<210> SEQ ID NO 3
<211> LENGTH: 21
<212> TYPE: DNA
<213> ORGANISM: Artificial Sequence
<220> FEATURE:
<223> OTHER INFORMATION: Primers for qRT-PCR validations of PIK3CD
      splice variants

<400> SEQUENCE: 3
tctcggatca tgatgttgtc g                                              21

<210> SEQ ID NO 4
<211> LENGTH: 19
<212> TYPE: RNA
<213> ORGANISM: Artificial Sequence
<220> FEATURE:
<223> OTHER INFORMATION: siRNA targeting PI3KCD exon 23

<400> SEQUENCE: 4
ccaacaucca acucaacaa                                                 19

<210> SEQ ID NO 5
<211> LENGTH: 19
<212> TYPE: RNA
<213> ORGANISM: Artificial Sequence
<220> FEATURE:
<223> OTHER INFORMATION: siRNA targeting exon 23

<400> SEQUENCE: 5

| | |
|---|---|
| uuguugaguu ggauguugg | 19 |

<210> SEQ ID NO 6
<211> LENGTH: 20
<212> TYPE: DNA
<213> ORGANISM: Artificial Sequence
<220> FEATURE:
<223> OTHER INFORMATION: Synthetic

<400> SEQUENCE: 6

| | |
|---|---|
| tgcgaagaag ctggtggtgc | 20 |

<210> SEQ ID NO 7
<211> LENGTH: 3045
<212> TYPE: DNA
<213> ORGANISM: Homo sapiens

<400> SEQUENCE: 7

| | |
|---|---|
| atgcccctg gggtggactg ccccatggaa ttctggacca aggaggagaa tcagagcgtt | 60 |
| gtggttgact tcctgctgcc cacaggggtc tacctgaact ccctgtgtc ccgcaatgcc | 120 |
| aacctcagca ccatcaagca gctgctgtgg caccgcgccc agtatgagcc gctcttccac | 180 |
| atgctcagtg cccccgaggc ctatgtgttc acctgcatca accagacagc ggagcagcaa | 240 |
| gagctggagg acgagcaacg gcgtctgtgt gacgtgcagc ccttcctgcc cgtcctgcgc | 300 |
| ctggtggccc gtgagggcga ccgcgtgaag aagctcatca actcacagat cagcctcctc | 360 |
| atcggcaaag gcctccacga gtttgactcc ttgtgcgacc agaagtgaa cgactttcgc | 420 |
| gccaagatgt gccaattctg cgaggaggcg gccgcccgcc ggcagcagct gggctggagc | 480 |
| gcctggctgc agtacagttt ccccctgcag ctggagccct cggctcaaac ctggggcct | 540 |
| ggtaccctgc ggctcccgaa ccgggccctt ctggtcaacg ttaagtttga gggcagcgag | 600 |
| gagagcttca ccttccaggt gtccaccaag gacgtgccgc tggcgctgat ggcctgtgcc | 660 |
| ctgcggaaga aggccacagt gttccggcag ccgctggtgg agcagccgga agactacacg | 720 |
| ctgcaggtga acggcaggca tgagtacctg tatggcagct acccgctctg ccagttccag | 780 |
| tacatctgca gctgcctgca cagtgggttg acccctcacc tgaccatggt ccattcctcc | 840 |
| tccatcctcg ccatgcggga tgagcagagc aaccctgccc ccaggtcca gaaaccgcgt | 900 |
| gccaaaccac ctcccattcc tgcgaagaag ctggtggtgc aggccgggct tttccacggc | 960 |
| aacgagatgc tgtgcaagac ggtgtccagc tcggaggtga gcgtgtgctc ggagcccgtg | 1020 |
| tggaagcagc ggctggagtt cgacatcaac atctgcgacc tgccccgcat ggcccgtctc | 1080 |
| tgctttgcgc tgtacgccgt gatcgagaaa gccaagaagg ctcgctccac caagaagaag | 1140 |
| tccaagaagg cggactgccc cattgcctgg gccaacctca tgctgtttga ctacaaggac | 1200 |
| cagcttaaga ccggggaacg ctgcctctac atgtggccct ccgtcccaga tgagaagggc | 1260 |
| gagctgctga cccccacggg cactgtgcgc agtaacccca acacggatag cgccgctgcc | 1320 |
| ctgctcatct gcctgcccga ggtggcccg caccccgtgt actacccgc cctggagaag | 1380 |
| atcttggagc tggggcgaca cagcgagtgt gtgcatgtca ccgaggagga gcagctgcag | 1440 |
| ctgcgggaaa tcctggagcg gcgggggtct ggggagctgt atgagcacga gaaggacctg | 1500 |
| gtgtggaagc tgcggcatga agtccaggag cacttcccgg aggcgctagc ccggctgctg | 1560 |
| ctggtcacca gtggaacaa gcatgaggat gtgcccagga tgctctacct gctgtgctcc | 1620 |
| tggccggagc tgcccgtcct gagcgccctg gagctgctag acttcagctt ccccgattgc | 1680 |
| cacgtaggct ccttcgccat caagtcgctg cggaaactga cggacgatga gctgttccag | 1740 |

```
tacctgctgc agctggtgca ggtgctcaag tacgagtcct acctggactg cgagctgacc      1800
aaattcctgc tggaccgggc cctggccaac cgcaagatcg gccacttcct tttctggcac      1860
ctccgctccg agatgcacgt gccgtcggtg gccctgcgct tcggcctcat cctggaggcc      1920
tactgcaggg gcagcaccca ccacatgaag gtgctgatga agcaggggga agcactgagc      1980
aaactgaagg ccctgaatga cttcgtcaag ctgagctctc agaagacccc caagccccag      2040
accaaggagc tgatgcactt gtgcatgcgg caggaggcct acctagaggc cctctcccac      2100
ctgcagtccc cactcgaccc cagcaccctg ctggctgaag tctgcgtgga gcagtgcacc      2160
ttcatggact ccaagatgaa gcccctgtgg atcatgtaca gcaacgagga ggcaggcagc      2220
ggcggcagcg tgggcatcat ctttaagaac ggggatgacc tccggcagga catgctgacc      2280
ctgcagatga tccagctcat ggacgtcctg tggaagcagg aggggctgga cctgaggatg      2340
accccctatg gctgcctccc caccggggac cgcacaggcc tcattgaggt ggtactccgt      2400
tcagacacca tcgccaacat ccaactcaac aagagcaaca tggcagccac agccgccttc      2460
aacaaggatg ccctgctcaa ctggctgaag tccaagaacc gggggaggc cctggatcga      2520 gccattgagg agttcaccct ctcctgtgct ggctattgtg tggccacata tgtgctgggc      2580
attggcgatc ggcacagcga caacatcatg atccgagaga gtgggcagct gttccacatt      2640
gattttggcc acttctgtgg gaatttcaag accaagtttg gaatcaaccg cgagcgtgtc      2700
ccattcatcc tcacctacga ctttgtccat gtgattcagc aggggaagac taataatagt      2760
gagaaatttg aacggttccg gggctactgt gaaagggcct acaccatcct gcggcgccac      2820
gggcttctct tcctccacct ctttgccctg atgcgggcgg caggcctgcc tgagctcagc      2880
tgctccaaag acatccagta tctcaaggac tccctggcac tggggaaaac agaggaggag      2940
gcactgaagc acttccgagt gaagtttaac gaagccctcc gtgagagctg gaaaaccaaa      3000
gtgaactggc tggcccacaa cgtgtccaaa gacaacaggc agtag                      3045
```

<210> SEQ ID NO 8
<211> LENGTH: 19
<212> TYPE: RNA
<213> ORGANISM: Artificial Sequence
<220> FEATURE:
<223> OTHER INFORMATION: Synthetic

<400> SEQUENCE: 8
cugcgaagaa gcuggugguu                                                  19

<210> SEQ ID NO 9
<211> LENGTH: 19
<212> TYPE: RNA
<213> ORGANISM: Artificial Sequence
<220> FEATURE:
<223> OTHER INFORMATION: Synthetic

<400> SEQUENCE: 9
accaccagcu ucuucgcag                                                   19

<210> SEQ ID NO 10
<211> LENGTH: 19
<212> TYPE: DNA
<213> ORGANISM: Artificial Sequence
<220> FEATURE:
<223> OTHER INFORMATION: Synthetic

<400> SEQUENCE: 10
tggacctgag ggaggccct                                                      19

<210> SEQ ID NO 11
<211> LENGTH: 2967
<212> TYPE: DNA
<213> ORGANISM: Homo sapiens

<400> SEQUENCE: 11

| | | | | | |
|---|---|---|---|---|---|
| atgcccctg | gggtggactg | ccccatggaa | ttctggacca | aggaggagaa | tcagagcgtt | 60 |
| gtggttgact | tcctgctgcc | cacaggggtc | tacctgaact | tccctgtgtc | ccgcaatgcc | 120 |
| aacctcagca | ccatcaagca | gctgctgtgg | caccgcgccc | agtatgagcc | gctcttccac | 180 |
| atgctcagtg | ccccgaggc | ctatgtgttc | acctgcatca | accagacagc | ggagcagcaa | 240 |
| gagctggagg | acgagcaacg | cgtctgtgt | gacgtgcagc | ccttcctgcc | cgtcctgcgc | 300 |
| ctggtggccc | gtgagggcga | ccgcgtgaag | aagctcatca | actcacagat | cagcctcctc | 360 |
| atcggcaaag | gcctccacga | gtttgactcc | ttgtgcgacc | cagaagtgaa | cgactttcgc | 420 |
| gccaagatgt | gccaattctg | cgaggaggcg | ccgcccgcc | ggcagcagct | gggctggag | 480 |
| gcctggctgc | agtacagttt | ccccctgcag | ctggagccct | cggctcaaac | ctgggggcct | 540 |
| ggtaccctgc | ggctcccgaa | ccgggccctt | ctggtcaacg | ttaagtttga | gggcagcgag | 600 |
| gagagcttca | ccttccaggt | gtccaccaag | gacgtgccgc | tggcgctgat | ggcctgtgcc | 660 |
| ctgcggaaga | aggccacagt | gttccggcag | ccgctggtgg | agcagccgga | agactacacg | 720 |
| ctgcaggtga | acggcaggca | tgagtacctg | tatggcagct | acccgctctg | ccagttccag | 780 |
| tacatctgca | gctgcctgca | cagtgggttg | accctcacc | tgaccatggt | ccattcctcc | 840 |
| tccatcctcg | ccatgcggga | tgagcagagc | aaccctgccc | ccaggtcca | gaaaccgcgt | 900 |
| gccaaaccac | ctcccattcc | tgcgaagaag | ccttcctctg | tgtccctgtg | gtccctggag | 960 |
| cagccgttcc | gcatcgagct | catccagggc | agcaaagtga | acgccgacga | gcggatgaag | 1020 |
| ctggtggtgc | aggccgggct | tttccacggc | aacgagatgc | tgtgcaagac | ggtgtccagc | 1080 |
| tcggaggtga | gcgtgtgctc | ggagcccgtg | tggaagcagc | ggctggagtt | cgacatcaac | 1140 |
| atctgcgacc | tgccccgcat | ggcccgtctc | tgctttgcgc | tgtacgccgt | gatcgagaaa | 1200 |
| gccaagaagg | ctcgctccac | caagaagaag | tccaagaagg | cggactgccc | cattgcctgg | 1260 |
| gccaacctca | tgctgtttga | ctacaaggac | cagcttaaga | ccggggaacg | ctgcctctac | 1320 |
| atgtggccct | ccgtcccaga | tgagaagggc | gagctgctga | ccccacgggg | cactgtgcgc | 1380 |
| agtaacccca | cacggatag | cgccgctgcc | ctgctcatct | gcctgcccga | ggtggccccg | 1440 |
| caccccgtgt | actaccccgc | cctggagaag | atcttggagc | tggggcgaca | cagcgagtgt | 1500 |
| gtgcatgtca | ccgaggagga | gcagctgcag | ctgcgggaaa | tcctggagcg | gcgggggtct | 1560 |
| ggggagctgt | atgagcacga | gaaggacctg | gtgtggaagc | tgcggcatga | agtccaggag | 1620 |
| cacttcccgg | aggcgctagc | ccggctgctg | ctggtcacca | gtggaacaa | gcatgaggat | 1680 |
| gtggcccaga | tgctctacct | gctgtgctcc | tggccggagc | tgccgtcct | gagcgccctg | 1740 |
| gagctgctag | acttcagctt | ccccgattgc | cacgtaggct | ccttcgccat | caagtcgctg | 1800 |
| cggaaactga | cggacgatga | gctgttccag | tacctgctgc | agctggtgca | ggtgctcaag | 1860 |
| tacgagtcct | acctggactg | cgagctgacc | aaattcctgc | tggaccgggc | cctggccaac | 1920 |
| cgcaagatcg | gccacttcct | tttctgcac | ctccgctccg | agatgcacgt | gccgtcggtg | 1980 |
| gccctgcgct | tcggctcat | cctggaggcc | tactgcaggg | gcagcacca | ccacatgaag | 2040 |
| gtgctgatga | agcaggggga | agcactgagc | aaactgaagg | ccctgaatga | cttcgtcaag | 2100 |

```
ctgagctctc agaagacccc caagcccag accaaggagc tgatgcactt gtgcatgcgg    2160
caggaggcct acctagaggc cctctcccac ctgcagtccc cactcgaccc cagcaccctg    2220
ctggctgaag tctgcgtgga gcagtgcacc ttcatggact ccaagatgaa gcccctgtgg    2280
atcatgtaca gcaacgagga ggcaggcagc ggcggcagcg tgggcatcat ctttaagaac    2340
ggggatgacc tccggcagga catgctgacc ctgcagatga tccagctcat ggacgtcctg    2400
tggaagcagg aggggctgga cctgagggag gccctggatc gagccattga ggagttcacc    2460
ctctcctgtg ctggctattg tgtggccaca tatgtgctgg gcattggcga tcggcacagc    2520
gacaacatca tgatccgaga gagtgggcag ctgttccaca ttgattttgg ccactttctg    2580
gggaatttca agaccaagtt tggaatcaac cgcgagcgtg tcccattcat cctcacctac    2640
gactttgtcc atgtgattca gcaggggaag actaataata gtgagaaatt tgaacggttc    2700
cggggctact gtgaagggc ctacaccatc ctgcggcgcc acgggcttct cttcctccac    2760
ctctttgccc tgatgcgggc ggcaggcctg cctgagctca gctgctccaa agacatccag    2820
tatctcaagg actccctggc actggggaaa acagaggagg aggcactgaa gcacttccga    2880
gtgaagttta cgaagccct ccgtgagagc tggaaaacca agtgaactg gctggcccac    2940 aacgtgtcca agacaacag gcagtag                                        2967
```

<210> SEQ ID NO 12
<211> LENGTH: 20
<212> TYPE: RNA
<213> ORGANISM: Artificial Sequence
<220> FEATURE:
<223> OTHER INFORMATION: Synthetic

<400> SEQUENCE: 12

```
ugagggaggc ccuggaucga                                                 20
```

<210> SEQ ID NO 13
<211> LENGTH: 20
<212> TYPE: RNA
<213> ORGANISM: Artificial Sequence
<220> FEATURE:
<223> OTHER INFORMATION: Synthetic

<400> SEQUENCE: 13

```
ucgauccagg gccuccuca                                                  20
```

<210> SEQ ID NO 14
<211> LENGTH: 2877
<212> TYPE: DNA
<213> ORGANISM: Homo sapiens

<400> SEQUENCE: 14

```
atgccccctg gggtggactg ccccatggaa ttctggacca aggaggagaa tcagagcgtt     60
gtggttgact tcctgctgcc cacaggggtc tacctgaact ccctgtgtc ccgcaatgcc    120 aacctcagca ccatcaagca gctgctgtgg caccgcgccc agtatgagcc gctcttccac    180
atgctcagtg gccccgaggc ctatgtgttc acctgcatca accagacagc ggagcagcaa    240
gagctggagg acgagcaacg gcgtctgtgt gacgtgcagc ccttcctgcc cgtcctgcgc    300
ctggtggccc gtgagggcga ccgcgtgaag aagctcatca actcacagat cagcctcctc    360
atcggcaaag gcctccacga gtttgactcc ttgtgcgacc cagaagtgaa cgactttcgc    420
gccaagatgt gccaattctg cgaggaggcg gccgcccgcc ggcagcagct gggctgggag    480
```

```
gcctggctgc agtacagttt cccccctgcag ctggagccct cggctcaaac ctgggggcct      540
ggtaccctgc ggctcccgaa ccgggcccctt ctggtcaacg ttaagtttga gggcagcgag     600
gagagcttca ccttccaggt gtccaccaag gacgtgccgc tggcgctgat ggcctgtgcc      660
ctgcggaaga aggccacagt gttccggcag ccgctggtgg agcagccgga agactacacg      720
ctgcaggtga acggcaggca tgagtacctg tatggcagct acccgctctg ccagttccag      780
tacatctgca gctgcctgca cagtgggttg acccctcacc tgaccatggt ccattcctcc      840
tccatcctcg ccatgcggga tgagcagagc aaccctgccc ccaggtccag gaaaccgcgt      900
gccaaaccac ctcccattcc tgcgaagaag ctggtggtgc aggccgggct tttccacggc      960
aacgagatgc tgtgcaagac ggtgtccagc tcggaggtga gcgtgtgctc ggagcccgtg     1020
tggaagcagc ggctggagtt cgacatcaac atctgcgacc tgccccgcat ggcccgtctc     1080
tgctttgcgc tgtacgccgt gatcgagaaa gccaagaagg ctcgctccac caagaagaag     1140
tccaagaagg cggactgccc cattgcctgg ccaacctca tgctgtttga ctacaaggac       1200
cagcttaaga ccggggaacg ctgcctctac atgtggccct ccgtcccaga tgagaagggc     1260
gagctgctga cccccacggg cactgtgcgc agtaacccca acacggatag cgccgctgcc     1320
ctgctcatct gcctgcccga ggtggcccg caccccgtgt actacccgc cctggagaag       1380
atcttggagc tggggcgaca cagcgagtgt gtgcatgtca ccgaggagga gcagctgcag     1440
ctgcgggaaa tcctggagcg gcgggggtct ggggagctgt atgagcacga aaggacctg      1500
gtgtggaagc tgcggcatga agtccaggag cacttcccgg aggcgctagc ccggctgctg     1560
ctggtcacca gtggaacaa gcatgaggat gtggcccaga tgctctacct gctgtgctcc      1620
tggccggagc tgcccgtcct gagcgccctg gagctgctag acttcagctt ccccgattgc    1680
cacgtaggct ccttcgccat caagtcgctg cggaaactga cggacgatga gctgttccag     1740
tacctgctgc agctggtgca ggtgctcaag tacgagtcct acctggactg cgagctgacc     1800
aaattcctgc tggaccgggc cctggccaac cgcaagatcg gccacttcct tttctgcac     1860
ctccgctccg agatgcacgt gccgtcggtg gccctgcgct tcggcctcat cctggaggcc   1920
tactgcaggg gcagcacccca ccacatgaag gtgctgatga gcagggggga agcactgagc   1980
aaactgaagg ccctgaatga cttcgtcaag ctgagctctc agaagacccc caagcccag     2040
accaaggagc tgatgcactt gtgcatgcgg caggaggcct acctagaggc cctctcccac    2100
ctgcagtccc cactcgaccc cagcacccctg ctggctgaag tctgcgtgga gcagtgcacc    2160
ttcatggact ccaagatgaa gccctgtgg atcatgtaca gcaacgagga ggcaggcagc     2220
ggcggcagcg tgggcatcat ctttaagaac ggggatgacc tccggcagga catgctgacc   2280
ctgcagatga tccagctcat ggacgtcctg tggaagcagg aggggctgga cctgagggag    2340
gccctggatc gagccattga ggagttcacc ctctcctgtg ctggctattg tgtggccaca   2400
tatgtgctgg gcattggcga tcggcacagc gacaacatca tgatccgaga gagtgggcag   2460
ctgttccaca ttgattttgg ccactttctg gggaatttca gaccaagttt ggaatcaac    2520
cgcgagcgtg tcccattcat cctcacctac gactttgtcc atgtgattca gcaggggaag    2580
actaataata gtgagaaatt tgaacggttc cggggctact gtgaaagggc ctacaccatc     2640
ctgcggcgcc acgggcttct cttcctccac ctctttgccc tgatgcggg ggcaggcctg    2700
cctgagctca gctgctccaa agacatccag tatctcaagg actccctggc actggggaaa   2760
acagaggagg aggcactgaa gcacttccga gtgaagtttta cgaagccct ccgtgagagc   2820
tggaaaaacca aagtgaactg gctggcccac aacgtgtcca aagacaacag gcagtag       2877
```

<210> SEQ ID NO 15
<211> LENGTH: 19
<212> TYPE: DNA
<213> ORGANISM: Artificial Sequence
<220> FEATURE:
<223> OTHER INFORMATION: Synthetic

<400> SEQUENCE: 15

```
acatgtggcc cctctcctg                                              19
```

<210> SEQ ID NO 16
<211> LENGTH: 1836
<212> TYPE: DNA
<213> ORGANISM: Homo sapiens

<400> SEQUENCE: 16

```
atgcccctg gggtggactg ccccatggaa ttctggacca aggaggagaa tcagagcgtt     60
gtggttgact tcctgctgcc cacaggggtc tacctgaact tccctgtgtc ccgcaatgcc    120
aacctcagca ccatcaagca gctgctgtgg caccgcgccc agtatgagcc gctcttccac    180
atgctcagtg gccccgaggc ctatgtgttc acctgcatca accagacagc ggagcagcaa    240
gagctggagg acgagcaacg gcgtctgtgt gacgtgcagc ccttcctgcc cgtcctgcgc    300
ctggtggccc gtgagggcga ccgcgtgaag aagctcatca actcacagat cagcctcctc    360
atcggcaaag gcctccacga gtttgactcc ttgtgcgacc agaagtgaa cgactttcgc     420 gccaagatgt gccaattctg cgaggaggcg ccgcccgcc ggcagcagct gggctgggag     480
gcctggctgc agtacagttt cccctgcag ctggagccct cggctcaaac ctggggcct     540 ggtaccctgc ggctcccgaa ccgggcccctt ctggtcaacg ttaagtttga gggcagcgag    600
gagagcttca ccttccaggt gtccaccaag gacgtgccgc tggcgctgat ggcctgtgcc    660
ctgcggaaga aggccacagt gttccggcag ccgctggtgg agcagccgga agactacacg    720
ctgcaggtga acggcaggca tgagtacctg tatggcagct acccgctctg ccagttccag    780
tacatctgca gctgcctgca cagtgggttg acccctcacc tgaccatggt ccattcctcc    840
tccatcctcg ccatgcggga tgagcagagc aaccctgccc ccaggtcca gaaaccgcgt     900 gccaaaccac ctcccattcc tgcgaagaag ccttcctctg tgtccctgtg gtccctggag    960
cagccgttcc gcatcgagct catccagggc agcaaagtga acgccgacga gcggatgaag   1020
ctggtggtgc aggccgggct tttccacggc aacgagatgc tgtgcaagac ggtgtccagc   1080
tcggaggtga gcgtgtgctc ggagcccgtg tggaagcagc ggctggagtt cgacatcaac   1140
atctgcgacc tgccccgcat ggcccgtctc tgctttgcgc tgtacgccgt gatcgagaaa   1200
gccaagaagg ctcgctccac caagaagaag tccaagaagg cggactgccc cattgcctgg   1260
gccaacctca tgctgtttga ctacaaggac cagcttaaga ccggggaacg ctgcctctac   1320
atgtggcccc tctcctgtgc tggctattgt gtggccacat atgtgctggg cattggcgat   1380
cggcacagcg acaacatcat gatccgagag agtgggcagc tgttccacat tgattttggc   1440
cactttctgg ggaatttcaa gaccaagttt ggaatcaacc gcgagcgtgt cccattcatc   1500
ctcacctacg actttgtcca tgtgattcag caggggaaga ctaataatag tgagaaattt   1560
gaacggttcc ggggctactg tgaaagggcc tacaccatcc tgcggcgcca cgggcttctc   1620
ttcctccacc tctttgccct gatgcgggcg gcaggcctgc ctgagctcag ctgctccaaa   1680
gacatccagt atctcaagga ctccctggca ctggggaaaa cagaggagga ggcactgaag   1740
```

| cacttccgag tgaagtttaa cgaagccctc cgtgagagct ggaaaaccaa agtgaactgg | 1800 |
| ctggcccaca acgtgtccaa agacaacagg cagtag | 1836 |

<210> SEQ ID NO 17
<211> LENGTH: 19
<212> TYPE: RNA
<213> ORGANISM: Artificial Sequence
<220> FEATURE:
<223> OTHER INFORMATION: Synthetic

<400> SEQUENCE: 17

| ccucuccugu gcuggcuau | 19 |

<210> SEQ ID NO 18
<211> LENGTH: 19
<212> TYPE: RNA
<213> ORGANISM: Artificial Sequence
<220> FEATURE:
<223> OTHER INFORMATION: Synthetic

<400> SEQUENCE: 18

| auagccagca caggagagg | 19 |

<210> SEQ ID NO 19
<211> LENGTH: 2421
<212> TYPE: DNA
<213> ORGANISM: Homo sapiens

<400> SEQUENCE: 19

| atgggcgccc ctgcctgcgc cctcgcgctc tgcgtggccg tggccatcgt ggccggcgcc | 60 |
| tcctcggagt ccttggggac ggagcagcgc gtcgtggggc gagcggcaga agtcccgggc | 120 |
| ccagagcccg gccagcagga gcagttggtc ttcggcagcg gggatgctgt ggagctgagc | 180 |
| tgtccccgc ccggggtgg tcccatgggg cccactgtct gggtcaagga tggcacaggg | 240 |
| ctggtgccct cggagcgtgt cctggtgggg cccagcggc tgcaggtgct gaatgcctcc | 300 |
| cacgaggact ccggggccta cagctgccgg cagcggctca cgcagcgcgt actgtgccac | 360 |
| ttcagtgtgc gggtgacaga cgctccatcc tcgggagatg acgaagacgg ggaggacgag | 420 |
| gctgaggaca caggtgtgga cacaggggcc ccttactgga cacggcccga gcggatggac | 480 |
| aagaagctgc tggccgtgcc ggccgccaac accgtccgct tccgctgccc agccgctggc | 540 |
| aaccccactc cctccatctc ctggctgaag aacggcaggg agttccgcgg cgagcaccgc | 600 |
| attggaggca tcaagctgcg gcatcagcag tggagcctgg tcatggaaag cgtggtgccc | 660 |
| tcggaccgcg gcaactacac ctgcgtcgtg gagaacaagt ttggcagcat ccggcagacg | 720 |
| tacacgctgg acgtgctgga gcgctccccg caccggccca tcctgcaggc ggggctgccg | 780 |
| gccaaccaga cggcggtgct gggcagcgac gtggagttcc actgcaaggt gtacagtgac | 840 |
| gcacagcccc acatccagtg gctcaagcac gtggaggtga atggcagcaa ggtgggcccg | 900 |
| gacggcacac cctacgttac cgtgctcaag acggcgggcg ctaacaccac cgacaaggag | 960 |
| ctagaggttc tctccttgca caacgtcacc tttgaggacg ccggggagta cacctgcctg | 1020 |
| gcgggcaatt ctattgggtt ttctcatcac tctgcgtggc tggtggtgct gccagccgag | 1080 |
| gaggagctgg tggaggctga cgaggcgggc agtgtgtatg caggcatcct cagctacggg | 1140 |
| gtgggcttct tcctgttcat cctggtggtg gcggctgtga cgctctgccg cctgcgcagc | 1200 |
| cccccaaga aaggcctggg ctccccacc gtgcacaaga tctcccgctt ccgctcaag | 1260 |
| cgacaggtgt ccctggagtc caacgcgtcc atgagctcca acacaccact ggtgcgcatc | 1320 |

```
gcaaggctgt cctcagggga gggccccacg ctggccaatg tctccgagct cgagctgcct    1380
gccgacccca atgggagct gtctcgggcc cggctgaccc tgggcaagcc ccttggggag    1440
ggctgcttcg gccaggtggt catggcggag ccatcggca ttgacaagga ccgggccgcc    1500
aagcctgtca ccgtagccgt gaagatgctg aaagacgatg ccactgacaa ggacctgtcg    1560
gacctggtgt ctgagatgga gatgatgaag atgatcggga aacacaaaaa catcatcaac    1620
ctgctgggcg cctgcacgca gggcgggccc ctgtacgtgc tggtggagta cgcggccaag    1680
ggtaacctgc gggagtttct gcgggcgcgg cggcccccgg gcctggacta ctccttcgac    1740
acctgcaagc cgcccgagga gcagctcacc ttcaaggacc tggtgtcctg tgcctaccag    1800
gtggcccggg gcatggagta cttggcctcc cagaagtgca tccacaggga cctggctgcc    1860
cgcaatgtgc tggtgaccga ggacaacgtg atgaagatcg cagacttcgg gctggccgg    1920 gacgtgcaca acctcgacta ctacaagaag acgaccaacg gccggctgcc cgtgaagtgg    1980
atggcgcctg aggccttgtt tgaccgagtc tacactcacc agagtgacgt ctggtccttt    2040
ggggtcctgc tctgggagat cttcacgctg gggggctccc cgtaccccgg catccctgtg    2100
gaggagctct tcaagctgct gaaggagggc accgcatgg acaagcccgc caactgcaca    2160
cacgacctgt acatgatcat gcgggagtgc tggcatgccg cgccctccca gaggcccacc    2220
ttcaagcagc tggtggagga cctggaccgt gtccttaccg tgacgtccac cgacgagtac    2280
ctggacctgt cggcgccttt cgagcagtac tccccgggtg gccaggacac ccccagctcc    2340
agctcctcag gggacgactc cgtgtttgcc cacgacctgc tgcccccggc cccacccagc    2400
agtgggggct cgcggacgtg a                                              2421
```

```
<210> SEQ ID NO 20
<211> LENGTH: 20
<212> TYPE: DNA
<213> ORGANISM: Artificial Sequence
<220> FEATURE:
<223> OTHER INFORMATION: Synthetic

<400> SEQUENCE: 20
acaacgtgat gaagatcgca                                                  20

<210> SEQ ID NO 21
<211> LENGTH: 19
<212> TYPE: DNA
<213> ORGANISM: Artificial Sequence
<220> FEATURE:
<223> OTHER INFORMATION: Synthetic

<400> SEQUENCE: 21
aggtcgtgtg tgcagttgg                                                   19

<210> SEQ ID NO 22
<211> LENGTH: 19
<212> TYPE: RNA
<213> ORGANISM: Artificial Sequence
<220> FEATURE:
<223> OTHER INFORMATION: Synthetic

<400> SEQUENCE: 22
cucgacuacu acaagaaga                                                   19

<210> SEQ ID NO 23
<211> LENGTH: 19
<212> TYPE: RNA
```

```
<213> ORGANISM: Artificial Sequence
<220> FEATURE:
<223> OTHER INFORMATION: Synthetic

<400> SEQUENCE: 23
ucuucuugua guagucgag                                                      19

<210> SEQ ID NO 24
<211> LENGTH: 23
<212> TYPE: DNA
<213> ORGANISM: Artificial Sequence
<220> FEATURE:
<223> OTHER INFORMATION: Synthetic

<400> SEQUENCE: 24
ttggcctccc agaagggccg gct                                                 23

<210> SEQ ID NO 25
<211> LENGTH: 2298
<212> TYPE: DNA
<213> ORGANISM: Homo sapiens

<400> SEQUENCE: 25
atgggcgccc ctgcctgcgc cctcgcgctc tgcgtggccg tggccatcgt ggccggcgcc         60
tcctcggagt ccttggggac ggagcagcgc gtcgtggggc gagcggcaga agtcccgggc        120
ccagagcccg gccagcagga gcagttggtc ttcggcagcg gggatgctgt ggagctgagc        180
tgtccccccg ccggggggtgg tcccatgggg cccactgtct gggtcaagga tggcacaggg        240
ctggtgccct cggagcgtgt cctggtgggg cccagcggc tgcaggtgct gaatgcctcc         300
cacgaggact ccggggccta cagctgccgg cagcggctca cgcagcgcgt actgtgccac        360
ttcagtgtgc gggtgacaga cgctccatcc tcgggagatg acgaagacgg ggaggacgag        420
gctgaggaca caggtgtgga cacaggggcc ccttactgga cacggcccga gcggatggac        480
aagaagctgc tggccgtgcc ggccgccaac accgtccgct tccgctgccc agccgctggc        540
aaccccactc cctccatctc ctggctgaag aacggcaggg agttccgcgg cgagcaccgc        600
attggaggca tcaagctgcg gcatcagcag tggagcctgg tcatggaaag cgtggtgccc        660
tcggaccgcg gcaactacac ctgcgtcgtg gagaacaagt ttggcagcat ccggcagacg        720
tacacgctgg acgtgctgga cgctcccccg caccggccca tcctgcaggc ggggctgccg        780
gccaaccaga cggcggtgct gggcagcgac gtggagttcc actgcaaggt gtacagtgac        840
gcacagcccc acatccagtg gctcaagcac gtggaggtga atggcagcaa ggtgggcccg        900
gacggcacac cctacgttac cgtgctcaag acggcgggcg ctaacaccac cgacaaggag        960
ctagaggttc tctccttgca caacgtcacc tttgaggacg ccggggagta cacctgcctg       1020
gcgggcaatt ctattgggtt ttctcatcac tctgcgtggc tggtggtgct gccagccgag       1080
gaggagctgg tggaggctga cgaggcgggc agtgtgtatg caggcatcct cagctacggg       1140
gtgggcttct tcctgttcat cctggtggtg gcggctgtga cgctctgccg cctgcgcagc       1200
cccccaagaa aaggcctggg ctcccccacc gtgcacaaga tctcccgctt cccgctcaag       1260
cgacaggtgt ccctggagtc caacgcgtcc atgagctcca acacaccact ggtgcgcatc       1320
gcaaggctgt cctcagggga gggcccacg ctggccaatg tctccgagct cgagctgcct       1380
gccgacccca aatgggagct gtctcgggcc cggctgaccc tgggcaagcc ccttggggag       1440
ggctgcttcg gccaggtggt catggcggag gccatcggca ttgacaagga ccgggccgcc       1500
aagcctgtca ccgtagccgt gaagatgctg aaagacgatg ccactgacaa ggacctgtcg       1560
```

```
gacctggtgt ctgagatgga gatgatgaag atgatcggga aacacaaaaa catcatcaac    1620
ctgctgggcg cctgcacgca gggcgggccc ctgtacgtgc tggtggagta cgcggccaag    1680
ggtaacctgc gggagtttct gcgggcgcgg cggcccccgg gcctggacta ctccttcgac    1740
acctgcaagc cgcccgagga gcagctcacc ttcaaggacc tggtgtcctg tgcctaccag    1800
gtggcccggg gcatggagta cttggcctcc cagaagggcc ggctgcccgt gaagtggatg    1860
gcgcctgagg ccttgtttga ccgagtctac actcaccaga gtgacgtctg gtcctttggg    1920
gtcctgctct gggagatctt cacgctgggg ggctccccgt accccggcat ccctgtggag    1980
gagctcttca agctgctgaa ggagggccac cgcatggaca gcccgccaa ctgcacacac    2040 gacctgtaca tgatcatgcg ggagtgctgg catgccgcgc cctcccagag gcccaccttc    2100
aagcagctgg tggaggacct ggaccgtgtc cttaccgtga cgtccaccga cgagtacctg    2160
gacctgtcgg cgcctttcga gcagtactcc ccgggtggcc aggacacccc cagctccagc    2220
tcctcagggg acgactccgt gtttgcccac gacctgctgc cccggcccc acccagcagt    2280 gggggctcgc ggacgtga                                                 2298

<210> SEQ ID NO 26
<211> LENGTH: 19
<212> TYPE: RNA
<213> ORGANISM: Artificial Sequence
<220> FEATURE:
<223> OTHER INFORMATION: Synthetic

<400> SEQUENCE: 26
ccucccagaa gggccggcu                                                  19

<210> SEQ ID NO 27
<211> LENGTH: 19
<212> TYPE: RNA
<213> ORGANISM: Artificial Sequence
<220> FEATURE:
<223> OTHER INFORMATION: Synthetic

<400> SEQUENCE: 27
agccggcccu ucugggagg                                                  19

<210> SEQ ID NO 28
<211> LENGTH: 5424
<212> TYPE: DNA
<213> ORGANISM: Homo sapiens

<400> SEQUENCE: 28
atggccaaac caacaagcaa agattcaggc ttgaaggaga agtttaagat tctgttggga      60
ctgggaacac cgaggccaaa tcccaggtct gcagagggta acagacgga gtttatcatc     120 accgcggaaa tactgagaga actgagcatg gaatgtggcc tcaacaatcg catccggatg     180 ataggggcaga tttgtgaagt cgcaaaaacc aagaaatttg aagagcacgc agtggaagca     240
ctctggaagg cggtcgcgga tctgttgcag ccggagcggc cgctggaggc ccggcacgcg     300
gtgctggctc tgctgaaggc catcgtgcag gggcagggcg agcgtttggg ggtcctcaga     360
gccctcttct ttaaggtcat caaggattac ccttccaacg aagaccttca cgaaaggctg     420
gaggttttca aggccctcac agacaatggg agacacatca cctacttgga ggaagagctg     480
gctgactttg tcctgcagtg gatggatgtt ggcttgtcct cggaattcct tctggtgctg     540
gtgaacttgg tcaaattcaa tagctgttac ctcgacgagt acatcgcaag gatggttcag     600
```

| | |
|---|---|
| atgatctgtc tgctgtgcgt ccggaccgcg tcctctgtgg acatagaggt ctccctgcag | 660 |
| gtgctggacg ccgtggtctg ctacaactgc ctgccggctg agagcctccc gctgttcatc | 720 |
| gttaccctct gtcgcaccat caacgtcaag gagctctgcg agccttgctg gaagctgatg | 780 |
| cggaacctcc ttggcaccca cctgggccac agcgccatct acaacatgtg ccacctcatg | 840 |
| gaggacagag cctacatgga ggacgcgccc ctgctgagag agccgtgtt ttttgtgggc | 900 |
| atggctctct ggggagccca ccggctctat tctctcagga actcgccgac atctgtgttg | 960 |
| ccatcatttt accaggccat ggcatgtccg aacgaggtgg tgtcctatga gatcgtcctg | 1020 |
| tccatcacca ggctcatcaa gaagtatagg aaggagctcc aggtggtggc gtgggacatt | 1080 |
| ctgctgaaca tcatcgaacg gctccttcag cagctccaga ccttggacag cccggagctc | 1140 |
| aggaccatcg tccatgacct gttgaccacg gtggaggagc tgtgtgacca gaacgagttc | 1200 |
| cacgggtctc aggagagata cttttgaactg gtggagagat gtgcggacca gaggcctgag | 1260 |
| tcctccctcc tgaacctgat ctcctataga gcgcagtcca tccacccggc caaggacggc | 1320 |
| tggattcaga acctgcaggc gctgatggag agattcttca ggagcgagtc ccgaggcgcc | 1380 |
| gtgcgcatca aggtgctgga cgtgctgtcc tttgtgctgc tcatcaacag gcagttctat | 1440 |
| gaggaggagc tgattaactc agtggtcatc tcgcagctct cccacatccc cgaggataaa | 1500 |
| gaccaccagg tccgaaagct ggccacccag ttgctggtgg acctggcaga gggctgccac | 1560 |
| acacaccact caacagcct gctggacatc atcgagaagg tgatggcccg ctccctctcc | 1620 |
| ccaccccgg agctggaaga aagggatgtg ccgcatact cggcctcctt ggaggatgtg | 1680 |
| aagacagccg tcctggggct tctggtcatc cttcagacca gctgtacac cctgcctgca | 1740 |
| agccacgcca cgcgtgtgta tgagatgctg gtcagccaca ttcagctcca ctacaagcac | 1800 |
| agctacaccc tgccaatcgc gagcagcatc cggctgcagg cctttgactt cctgttgctg | 1860 |
| ctgcgggccg actcactgca ccgcctgggc ctgcccaaca aggatggagt cgtgcggttc | 1920 |
| agccccctact cgctctgcga ctacatggag ccagagagag gctctgagaa aagaccagc | 1980 |
| ggcccccttt ctcctcccac agggcctcct ggccggcgc ctgcaggccc cgccgtgcgg | 2040 |
| ctgggggtccg tgcctactc cctgctcttc cgcgtcctgc tgcagtgctt gaagcaggag | 2100 |
| tctgactgga aggtgctgaa gctggttctg ggcaggctgc ctgagtccct gcgctataaa | 2160 |
| gtgctcatct ttacttcccc ttgcagtgtg accagctgt gctctgctct ctgctccatg | 2220 |
| ctttcaggcc caaagacact ggagcggctc cgaggcgccc cagaaggctt ctccagaact | 2280 |
| gacttgcacc tggccgtggt tccagtgctg acagcattaa tctcttacca taactacctg | 2340 |
| gacaaaacca aacagcgcga gatggtctac tgcctggagc agggcctcat ccaccgctgt | 2400 |
| gccagccagt gcgtcgtggc cttgtccatc tgcagcgtgg agatgcctga catcatcatc | 2460 |
| aaggcgctgc ctgttctggt ggtgaagctc acgcacatct cagccacagc cagcatggcc | 2520 |
| gtcccactgc tggagttcct gtccactctg gccaggctgc cgcacctcta caggaacttt | 2580 |
| gccgcggagc agtatgccag tgtgttcgcc atctccctgc cgtacaccaa cccctccaag | 2640 |
| tttaatcagt acatcgtgtg tctggcccat cacgtcatag ccatgtggtt catcaggtgc | 2700 |
| cgcctgccct ccggaagga ttttgtccct ttcatcacta agggcctgcg gtccaatgtc | 2760 |
| ctcttgtctt tgatgacac ccccgagaag gacagcttca gggcccggag tactagtctc | 2820 |
| aacgagagac ccaagagtct gaggatagcc agacccccca aacaaggctt gaataactct | 2880 |
| ccacccgtga agaattcaa ggagagctct gcagccgagg ccttccggtg ccgcagcatc | 2940 |
| agtgtgtctg aacatgtggt ccgcagcagg atacagacgt ccctcaccag tgccagcttg | 3000 |

```
gggtctgcag atgagaactc cgtggcccag gctgacgata gcctgaaaaa cctccacctg   3060
gagctcacgg aaacctgtct ggacatgatg gctcgatacg tcttctccaa cttcacggct   3120
gtcccgaaga ggtctcctgt gggcgagttc ctcctagcgg gtggcaggac caaaacctgg   3180
ctggttggga acaagcttgt cactgtgacg acaagcgtgg gaaccgggac ccggtcgtta   3240
ctaggcctgg actcggggga gctgcagtcc ggcccggagt cgagctccag ccccggggtg   3300
catgtgagac agaccaagga ggcgccggcc aagctggagt cccaggctgg gcagcaggtg   3360
tcccgtgggg cccgggatcg ggtccgttcc atgtcggggg gccatggtct tcgagttggc   3420
gccctggacg tgccggcctc ccagttcctg ggcagtgcca cttctccagg accacggact   3480
gcaccagccg cgaaacctga gaaggcctca gctggcaccc gggttcctgt gcaggagaag   3540
acgaacctgg cggcctatgt gcccctgctg acccagggct gggcggagat cctggtccgg   3600
aggcccacag ggaacaccag ctggctgatg agcctggaga acccgctcag ccctttctcc   3660
tcggacatca acaacatgcc cctgcaggag ctgtctaacg ccctcatggc ggctgagcgc   3720
ttcaaggagc accgggacac agccctgtac aagtcactgt cggtgccggc agccagcacg   3780
gccaaacccc ctcctctgcc tcgctccaac acagtggcct cttctcctc cctgtaccag   3840 tccagctgcc aaggacagct gcacaggagc gtttcctggg cagactccgc cgtggtcatg   3900
gaggagggaa gtccgggcga ggttcctgtg ctggtggagc ccccagggtt ggaggacgtt   3960
gaggcagcgc taggcatgga caggcgcacg gatgcctaca gcaggtcgtc ctcagtctcc   4020
agccaggagg agaagtcgct ccacgcggag gagctggttg gcaggggcat ccccatcgag   4080
cgagtcgtct cctcggaggg tggccggccc tctgtggacc tctccttcca gccctcgcag   4140
cccctgagca gtccagctc ctctcccgag ctgcagactc tgcaggacat cctcggggac   4200
cctggggaca aggccgacgt gggccggctg agccctgagg ttaaggcccg gtcacagtca   4260
gggaccctgg acggggaaag tgctgcctgg tcggcctcgg gcgaagacag tcggggccag   4320
cccgagggtc ccttgccttc cagctccccc cgctcgccca gtggcctccg gccccgaggt   4380
tacaccatct ccgactcggc cccatcacgc aggggcaaga gagtagagag ggacgccta   4440 aagagcagag ccacagcctc caatgcagag aaagtgccag gcatcaaccc cagtttcgtg   4500
ttcctgcagc tctaccattc cccttctttt ggcgacgagt caaacaagcc aatcctgctg   4560
cccaatgagt cacagtcctt tgagcggtcg gtgcagctcc tcgaccagat ccatcatac   4620 gacacccaca agatcgccgt cctgtatgtt ggagaaggcc agagcaacag cgagctcgcc   4680
atcctgtcca atgagcatgg ctcctacagg tacacggagt tcctgacggg cctgggccgg   4740
ctcatcgagc tgaaggactg ccagccggac aaggtgtacc tgggaggcct ggacgtgtgt   4800
ggtgaggacg ccagttcac ctactgctgg cacgatgaca tcatgcaagc cgtcttccac   4860
atcgccaccc tgatgcccac caaggacgtg gacaagcacc gctgcgacaa gaagcgccac   4920
ctgggcaacg acttttgtgtc cattgtctac aatgactccg gtgaggactt caagcttggc   4980
accatcaagg gccagttcaa ctttgtccac gtgatcgtca cccgctgga ctacgagtgc   5040 aacctggtgt ccctgcagtg caggaaagac atggagggcc ttgtggacac cagcgtggcc   5100
aagatcgtgt ctgaccgcaa cctgcccttc gtggcccgcc agatggccct gcacgcaaat   5160
atggcctcac aggtgcatca tagccgctcc aaccccaccg atatctaccc ctccaagtgg   5220
attgcccggc tccgccacat caagcggctc cgccagcgga tctgcgagga agccgcctac   5280 tccaaccccca gcctacctct ggtgcaccct ccgtcccata gcaaagcccc tgcacagact   5340
```

```
ccagccgagc ccacacctgg ctatgaggtg ggccagcgga agcgcctcat ctcctcggtg    5400
gaggacttca ccgagtttgt gtga                                           5424
```

<210> SEQ ID NO 29
<211> LENGTH: 20
<212> TYPE: DNA
<213> ORGANISM: Artificial Sequence
<220> FEATURE:
<223> OTHER INFORMATION: Synthetic

<400> SEQUENCE: 29

```
tttgacttcc tgttgctgct                                                  20
```

<210> SEQ ID NO 30
<211> LENGTH: 19
<212> TYPE: DNA
<213> ORGANISM: Artificial Sequence
<220> FEATURE:
<223> OTHER INFORMATION: Synthetic

<400> SEQUENCE: 30

```
tgagcacttt atagcgcag                                                   19
```

<210> SEQ ID NO 31
<211> LENGTH: 19
<212> TYPE: RNA
<213> ORGANISM: Artificial Sequence
<220> FEATURE:
<223> OTHER INFORMATION: Synthetic

<400> SEQUENCE: 31

```
cugcgcuaua aagugcuca                                                   19
```

<210> SEQ ID NO 32
<211> LENGTH: 19
<212> TYPE: RNA
<213> ORGANISM: Artificial Sequence
<220> FEATURE:
<223> OTHER INFORMATION: Synthetic

<400> SEQUENCE: 32

```
ugagcacuuu auagcgcag                                                   19
```

<210> SEQ ID NO 33
<211> LENGTH: 20
<212> TYPE: DNA
<213> ORGANISM: Artificial Sequence
<220> FEATURE:
<223> OTHER INFORMATION: Synthetic

<400> SEQUENCE: 33

```
cttgaagcag ctttcaggcc                                                  20
```

<210> SEQ ID NO 34
<211> LENGTH: 5301
<212> TYPE: DNA
<213> ORGANISM: Homo sapiens

<400> SEQUENCE: 34

```
atggccaaac caacaagcaa agattcaggc ttgaaggaga agtttaagat tctgttggga     60
ctgggaacac cgaggccaaa tcccaggtct gcagagggta aacagacgga gtttatcatc    120 accgcgaaa tactgagaga actgagcatg gaatgtggcc tcaacaatcg catccggatg    180
atagggcaga tttgtgaagt cgcaaaaaacc aagaaatttg aagagcacgc agtggaagca    240
```

```
ctctggaagg cggtcgcgga tctgttgcag ccggagcggc cgctggaggc ccggcacgcg    300
gtgctggctc tgctgaaggc catcgtgcag gggcagggcg agcgtttggg ggtcctcaga    360
gccctcttct ttaaggtcat caaggattac ccttccaacg aagaccttca cgaaaggctg    420
gaggttttca aggccctcac agacaatggg agacacatca cctacttgga ggaagagctg    480
gctgactttg tcctgcagtg gatggatgtt ggcttgtcct cggaattcct tctggtgctg    540
gtgaacttgg tcaaattcaa tagctgttac ctcgacgagt acatcgcaag gatggttcag    600
atgatctgtc tgctgtgcgt ccggaccgcg tcctctgtgg acatagaggt ctccctgcag    660
gtgctggacg ccgtggtctg ctacaactgc ctgccggctg agagcctccc gctgttcatc    720
gttaccctct gtcgcaccat caacgtcaag gagctctgcg agccttgctg gaagctgatg    780
cggaacctcc ttggcaccca cctgggccac agcgccatct acaacatgtg ccacctcatg    840
gaggacagag cctacatgga ggacgcgccc ctgctgagag agccgtgtt ttttgtgggc    900 atggctctct ggggagccca ccggctctat tctctcagga actcgccgac atctgtgttg    960
ccatcatttt accaggccat ggcatgtccg aacgaggtgg tgtcctatga gatcgtcctg   1020
tccatcacca ggctcatcaa gaagtatagg aaggagctcc aggtggtggc gtgggacatt   1080
ctgctgaaca tcatcgaacg gctccttcag cagctccaga ccttggacag cccggagctc   1140
aggaccatcg tccatgacct gttgaccacg gtggaggagc tgtgtgacca gaacgagttc   1200
cacgggtctc aggagagata ctttgaactg gtggagagat gtgcggacca gaggcctgag   1260
tcctccctcc tgaacctgat ctcctataga gcgcagtcca tccacccggc caaggacggc   1320
tggattcaga acctgcaggc gctgatggag agattcttca ggagcgagtc ccgaggcgcc   1380
gtgcgcatca aggtgctgga cgtgctgtcc tttgtgctgc tcatcaacag gcagttctat   1440
gaggaggagc tgattaactc agtggtcatc tcgcagctct cccacatccc cgaggataaa   1500
gaccaccagg tccgaaagct ggccacccag ttgctggtgg acctggcaga gggctgccac   1560
acacaccact tcaacagcct gctggacatc atcgagaagg tgatggcccg ctccctctcc   1620 ccaccccgg agctgaagga aagggatgtg ccgcatact cggcctcctt ggaggatgtg   1680
aagacagccg tcctggggct tctggtcatc cttcagacca agctgtacac cctgcctgca   1740
agccacgcca cgcgtgtgta tgagatgctg tcagccaca ttcagctcca ctacaagcac   1800
agctacaccc tgccaatcgc gagcagcatc cggctgcagg cctttgactt cctgttgctg   1860
ctgcgggccg actcactgca ccgcctgggc ctgcccaaca aggatggagt cgtgcggttc   1920
agcccctact gcgtctgcga ctacatggag ccagagagag gctctgagaa gaagaccagc   1980 ggccccctt ctcctcccac agggcctcct ggccggcgc ctgcaggccc gccgtgcgg   2040 ctggggtccg tgccctactc cctgctcttc cgcgtcctgc tgcagtgctt gaagcagctt   2100
tcaggcccaa agacactgga gcggctccga ggcgcccag aaggcttctc cagaactgac   2160
ttgcacctgg ccgtggttcc agtgctgaca gcattaatct cttaccataa ctacctggac   2220
aaaaccaaac agcgcgagat ggtctactgc ctggagcagg cctcatccca ccgctgtgcc   2280
agccagtgcg tcgtggcctt gtccatctgc agcgtggaga tgcctgacat catcatcaag   2340
gcgctgcctg ttctggtggt gaagctcacg cacatctcag ccacagccag catggccgtc   2400
ccactgctgg agttcctgtc cactctggcc aggctgccgc acctctacag gaactttgcc   2460
gcggagcagt atgccagtgt gttcgccatc tccctgccgt acaccaaccc ctccaagttt   2520
aatcagtaca tcgtgtgtct ggcccatcac gtcatagcca tgtggtcat caggtgccgc   2580
```

```
ctgcccttcc ggaaggattt tgtcccttc atcactaagg gcctgcggtc caatgtcctc    2640
ttgtcttttg atgacacccc cgagaaggac agcttcaggg cccggagtac tagtctcaac    2700
gagagaccca agagtctgag gatagccaga ccccccaaac aaggcttgaa taactctcca    2760
cccgtgaaag aattcaagga gagctctgca gccgaggcct tccggtgccg cagcatcagt    2820
gtgtctgaac atgtggtccg cagcaggata cagacgtccc tcaccagtgc cagcttgggg    2880
tctgcagatg agaactccgt ggcccaggct gacgatagcc tgaaaaacct ccacctggag    2940
ctcacggaaa cctgtctgga catgatggct cgatacgtct tctccaactt cacggctgtc    3000
ccgaagaggt ctcctgtggg cgagttcctc ctagcgggtg gcaggaccaa aacctggctg    3060
gttgggaaca agcttgtcac tgtgacgaca agcgtgggaa ccgggacccg gtcgttacta    3120
ggcctggact cgggggagct gcagtccggc ccggagtcga gctccagccc cggggtgcat    3180
gtgagacaga ccaaggaggc gccggccaag ctggagtccc aggctgggca gcaggtgtcc    3240
cgtggggccc gggatcgggt ccgttccatg tcgggggggcc atggtcttcg agttggcgcc    3300
ctggacgtgc cggcctccca gttcctgggc agtgccactt ctccaggacc acggactgca    3360
ccagccgcga aacctgagaa ggcctcagct ggcacccggg ttcctgtgca ggagaagacg    3420
aacctggcgg cctatgtgcc cctgctgacc cagggctggg cggagatcct ggtccggagg    3480
cccacaggga acaccagctg gctgatgagc ctggagaacc cgctcagccc tttctcctcg    3540
gacatcaaca acatgcccct gcaggagctg tctaacgccc tcatggcggc tgagcgcttc    3600
aaggagcacc gggacacagc cctgtacaag tcactgtcgg tgccggcagc cagcacggcc    3660 aaacccctc ctctgcctcg ctccaacaca gtggcctctt tctcctccct gtaccagtcc    3720
agctgccaag gacagctgca caggagcgtt tcctgggcag actccgccgt ggtcatggag    3780
gagggaagtc cgggcgaggt tcctgtgctg gtggagcccc cagggttgga ggacgttgag    3840
gcagcgctag gcatggacag gcgcacggat gcctacagca ggtcgtcctc agtctccagc    3900
caggaggaga agtcgctcca cgcggaggag ctggttggca gggcatccc catcgagcga    3960 gtcgtctcct cggagggtgg ccggccctct gtggacctct ccttccagcc ctcgcagccc    4020
ctgagcaagt ccagctcctc tcccgagctg cagactctgc aggacatcct cggggaccct    4080
ggggacaagg ccgacgtggg ccggctgagc cctgaggtta aggcccggtc acagtcaggg    4140 acctggacg gggaaagtgc tgcctggtcg gcctcgggcg aagacagtcg gggccagccc    4200
gagggtccct tgccttccag ctcccccgc tcgcccagtg gcctccggcc ccgaggttac    4260
accatctccg actcggcccc atcacgcagg ggcaagagag tagagaggga cgccttaaag    4320
agcagagcca cagcctccaa tgcagagaaa gtgccaggca tcaaccccag tttcgtgttc    4380
ctgcagctct accattcccc cttctttggc gacgagtcaa acaagccaat cctgctgccc    4440
aatgagtcac agtcctttga gcggtcggtg cagctcctcg accagatccc atcatacgac    4500
acccacaaga tcgccgtcct gtatgttgga aaggccaga gcaacagcga gctcgccatc    4560
ctgtccaatg agcatggctc ctacaggtac acggagttcc tgacgggcct gggccggctc    4620
atcgagctga aggactgcca gccggacaag gtgtacctgg aggcctgga cgtgtgtggt    4680 gaggacggcc agttcaccta ctgctggcac gatgacatca tgcaagccgt cttccacatc    4740
gccaccctga tgcccaccaa ggacgtggac aagcaccgct gcgacaagaa gcgccacctg    4800
ggcaacgact ttgtgtccat tgtctacaat gactccggtg aggacttcaa gcttggcacc    4860 atcaagggc agttcaactt tgtccacgtg atcgtcaccc gctgactga cgagtgcaac    4920 ctggtgtccc tgcagtgcag gaaagacatg gagggccttg tggacaccag cgtggccaag    4980
```

```
atcgtgtctg accgcaacct gcccttcgtg gcccgccaga tggccctgca cgcaaatatg    5040
gcctcacagg tgcatcatag ccgctccaac cccaccgata tctacccctc caagtggatt    5100
gcccggctcc gccacatcaa gcggctccgc cagcggatct gcgaggaagc cgcctactcc    5160
aaccccagcc tacctctggt gcaccctccg tcccatagca aagcccctgc acagactcca    5220
gccgagccca cacctggcta tgaggtgggc cagcggaagc gcctcatctc ctcggtggag    5280
gacttcaccg agtttgtgtg a                                              5301
```

<210> SEQ ID NO 35
<211> LENGTH: 19
<212> TYPE: RNA
<213> ORGANISM: Artificial Sequence
<220> FEATURE:
<223> OTHER INFORMATION: Synthetic

<400> SEQUENCE: 35

```
gaagcagcuu ucaggccca                                                  19
```

<210> SEQ ID NO 36
<211> LENGTH: 19
<212> TYPE: RNA
<213> ORGANISM: Artificial Sequence
<220> FEATURE:
<223> OTHER INFORMATION: Synthetic

<400> SEQUENCE: 36

```
ugggccugaa agcugcuuc                                                  19
```

<210> SEQ ID NO 37
<211> LENGTH: 1830
<212> TYPE: DNA
<213> ORGANISM: Homo sapiens

<400> SEQUENCE: 37

```
atggcaggca ccctggacct ggacaagggc tgcacggtgg aggagctgct ccgcgggtgc      60
atcgaagcct tcgatgactc cgggaaggtg cgggacccgc agctggtgcg catgttcctc     120
atgatgcacc cctggtacat cccctcctct cagctgcgg ccaagctgct ccacatctac      180
caacaatccc ggaaggacaa ctccaattcc ctgcaggtga aaacgtgcca cctggtcagg     240
tactggatct ccgccttccc agcggagttt gacttgaacc cggagttggc tgagcagatc     300
aaggagctga aggctctgct agaccaagaa gggaaccgac ggcacagcag cctaatcgac     360
atagacagcg tccctaccta caagtggaag cggcaggtga ctcagcggaa ccctgtggga     420
cagaaaaagc gcaagatgtc cctgttgttt gaccacctgg agcccatgga gctggcggag     480 catctcaccct acttggagta tcgctccttc tgcaagatcc tgtttcagga ctatacagt     540 ttcgtgactc atggctgcac tgtggacaac cccgtcctgg agcggttcat ctccctcttc     600
aacagcgtct cacagtgggt gcagctcatg atcctcagca aacccacagc cccgcagcgg     660
gccctggtca tcacacactt tgtccacgtg gcggagaagc tgctacagct gcagaacttc     720
aacacgctga tggcagtggt cggggccctg agccacagct ccatctcccg cctcaaggag     780
acccacagcc acgttagccc tgagaccatc aagctctggg agggtctcac ggaactagtg     840
acggcgacag gcaactatgg caactaccgg cgtcggctgg cagcctgtgt gggcttccgc     900
ttcccgatcc tgggtgtgca cctcaaggac ctggtggccc tgcagctggc actgcctgac     960
tggctggacc cagcccggac ccggctcaac ggggccaaga tgaagcagct ctttagcatc    1020
```

```
ctggaggagc tggccatggt gaccagcctg cggccaccag tacaggccaa ccccgacctg    1080
ctgagcctgc tcacggtgtc tctggatcag tatcagacgg aggatgagct gtaccagctg    1140
tccctgcagc gggagccgcg ctccaagtcc tcgccaacca gccccacgag ttgcacccca    1200
ccaccccggc ccccggtact ggaggagtgg acctcggctg ccaaacccaa gctggatcag    1260
gccctcgtgg tggagcacat cgagaagatg gtggagtctg tgttccggaa ctttgacgtc    1320
gatggggatg ccacatctc acaggaagaa ttccagatca tccgtgggaa cttcccttac    1380
ctcagcgcct ttggggacct cgaccagaac caggatggct gcatcagcag ggaggagatg    1440
gtttcctatt tcctgcgctc cagctctgtg ttggggggggc gcatgggctt cgtacacaac    1500
ttccaggaga gcaactcctt cgccccgtc gcctgccgcc actgcaaagc cctgatcctg    1560
ggcatctaca gcagggcct caaatgccga gcctgtggag tgaactgcca caagcagtgc    1620
aaggatcgcc tgtcagttga gtgtcggcgc agggcccaga gtgtgagcct ggagggtct    1680 gcaccctcac cctcacccat gcacagccac catcaccgcg ccttcagctt ctctctgccc    1740
cgccctggca ggcgaggctc caggcctcca gagatccgtg aggaggaggt acagacggtg    1800
gaggatgggg tgtttgacat ccacttgtaa                                    1830

<210> SEQ ID NO 38
<211> LENGTH: 21
<212> TYPE: DNA
<213> ORGANISM: Artificial Sequence
<220> FEATURE:
<223> OTHER INFORMATION: Synthetic

<400> SEQUENCE: 38
tcacggtgtc tctggatcag t                                              21

<210> SEQ ID NO 39
<211> LENGTH: 21
<212> TYPE: DNA
<213> ORGANISM: Artificial Sequence
<220> FEATURE:
<223> OTHER INFORMATION: Synthetic

<400> SEQUENCE: 39
ccaccatctt ctcgatgtgc t                                              21

<210> SEQ ID NO 40
<211> LENGTH: 19
<212> TYPE: RNA
<213> ORGANISM: Artificial Sequence
<220> FEATURE:
<223> OTHER INFORMATION: Synthetic

<400> SEQUENCE: 40
guggagcaca ucgagaaga                                                 19

<210> SEQ ID NO 41
<211> LENGTH: 19
<212> TYPE: RNA
<213> ORGANISM: Artificial Sequence
<220> FEATURE:
<223> OTHER INFORMATION: Synthetic

<400> SEQUENCE: 41
ucuucucgau gugcuccac                                                 19

<210> SEQ ID NO 42
<211> LENGTH: 19
```

```
<212> TYPE: RNA
<213> ORGANISM: Artificial Sequence
<220> FEATURE:
<223> OTHER INFORMATION: Synthetic

<400> SEQUENCE: 42
ccacaucuca caggaagaa                                                  19

<210> SEQ ID NO 43
<211> LENGTH: 19
<212> TYPE: RNA
<213> ORGANISM: Artificial Sequence
<220> FEATURE:
<223> OTHER INFORMATION: Synthetic

<400> SEQUENCE: 43
uucuuccugu gagaugugg                                                  19

<210> SEQ ID NO 44
<211> LENGTH: 20
<212> TYPE: DNA
<213> ORGANISM: Artificial Sequence
<220> FEATURE:
<223> OTHER INFORMATION: Synthetic

<400> SEQUENCE: 44
caagtcctcg tctgtgttcc                                                 20

<210> SEQ ID NO 45
<211> LENGTH: 1707
<212> TYPE: DNA
<213> ORGANISM: Homo sapiens

<400> SEQUENCE: 45
atggcaggca ccctggacct ggacaagggc tgcacggtgg aggagctgct ccgcgggtgc      60
atcgaagcct tcgatgactc cgggaaggtg cgggacccgc agctggtgcg catgttcctc     120
atgatgcacc cctggtacat ccctcctct cagctggcgg ccaagctgct ccacatctac     180
caacaatccc ggaaggacaa ctccaattcc ctgcaggtga aaacgtgcca cctggtcagg     240
tactggatct ccgccttccc agcggagttt gacttgaacc cggagttggc tgagcagatc     300
aaggagctga aggctctgct agaccaagaa gggaaccgac ggcacagcag cctaatcgac     360
atagacagcg tccctaccta caagtggaag cggcaggtga ctcagcggaa ccctgtggga     420
cagaaaaagc gcaagatgtc cctgttgttt gaccacctgg agcccatgga gctggcggag     480
catctcaccc acttggagta tcgctccttc tgcaagatcc tgtttcagga ctatcacagt     540
ttcgtgactc atggctgcac tgtggacaac cccgtcctgg agcggttcat ctccctcttc     600
aacagcgtct cacagtgggt gcagctcatg atcctcagca acccacagc cccgcagcgg     660 gccctggtca tcacacactt tgtccacgtg gcggagaagc tgctacagct gcagaacttc     720
aacacgctga tggcagtggt cgggggcctg agccacagct ccatctcccg cctcaaggag     780
acccacagcc acgttagccc tgagaccatc aagctctggg agggtctcac ggaactagtg     840
acggcgacag gcaactatgg caactaccgg cgtcggctgg cagcctgtgt gggcttccgc     900
ttcccgatcc tgggtgtgca cctcaaggac ctggtggccc tgcagctggc actgcctgac     960
tggctggacc cagcccggac ccggctcaac ggggccaaga tgaagcagct ctttagcatc    1020
ctggaggagc tggccatggt gaccagcctg cggccaccag tacaggccaa ccccgacctg    1080
ctgagcctgc tcacggtgtc tctggatcag tatcagacgg aggatgagct gtaccagctg    1140
```

-continued

| | | |
|---|---|---|
| tccctgcagc gggagccgcg ctccaagtcc tcgtctgtgt tccggaactt tgacgtcgat | 1200 | |
| ggggatggcc acatctcaca ggaagaattc cagatcatcc gtgggaactt cccttacctc | 1260 | |
| agcgcctttg gggacctcga ccagaaccag gatggctgca tcagcaggga ggagatggtt | 1320 | |
| tcctatttcc tgcgctccag ctctgtgttg ggggggcgca tgggcttcgt acacaacttc | 1380 | |
| caggagagca actccttgcg ccccgtcgcc tgccgccact gcaaagccct gatcctgggc | 1440 | |
| atctacaagc agggcctcaa atgccgagcc tgtggagtga actgccacaa gcagtgcaag | 1500 | |
| gatcgcctgt cagttgagtg tcggcgcagg gcccagagtg tgagcctgga ggggtctgca | 1560 | |
| ccctcaccct cacccatgca cagccaccat caccgcgcct tcagcttctc tctgccccgc | 1620 | |
| cctggcaggc gaggctccag gcctccagag atccgtgagg aggaggtaca gacggtggag | 1680 | |
| gatggggtgt ttgacatcca cttgtaa | 1707 | |

<210> SEQ ID NO 46
<211> LENGTH: 19
<212> TYPE: RNA
<213> ORGANISM: Artificial Sequence
<220> FEATURE:
<223> OTHER INFORMATION: Synthetic

<400> SEQUENCE: 46
ccucgucugu guuccggaa                                                19

<210> SEQ ID NO 47
<211> LENGTH: 19
<212> TYPE: RNA
<213> ORGANISM: Artificial Sequence
<220> FEATURE:
<223> OTHER INFORMATION: Synthetic

<400> SEQUENCE: 47
uuccggaaca cagacgagg                                                19

<210> SEQ ID NO 48
<211> LENGTH: 20
<212> TYPE: DNA
<213> ORGANISM: Artificial Sequence
<220> FEATURE:
<223> OTHER INFORMATION: Synthetic

<400> SEQUENCE: 48
gatggtggag ggatggctgc                                               20

<210> SEQ ID NO 49
<211> LENGTH: 1714
<212> TYPE: DNA
<213> ORGANISM: Homo sapiens

<400> SEQUENCE: 49

| | | |
|---|---|---|
| atggcaggca ccctggacct ggacaagggc tgcacggtgg aggagctgct ccgcgggtgc | 60 | |
| atcgaagcct tcgatgactc cgggaaggtg cgggacccgc agctggtgcg catgttcctc | 120 | |
| atgatgcacc cctggtacat cccctcctct cagctggcgg ccaagctgct ccacatctac | 180 | |
| caacaatccc ggaaggacaa ctccaattcc ctgcaggtga aaacgtgcca cctggtcagg | 240 | |
| tactggatct ccgccttccc agcggagttt gacttgaacc cggagttggc tgagcagatc | 300 | |
| aaggagctga aggctctgct agaccaagaa gggaaccgac ggcacagcag cctaatcgac | 360 | |
| atagacagcg tccctaccta caagtggaag cggcaggtga ctcagcggaa ccctgtggga | 420 | |
| cagaaaaagc gcaagatgtc cctgttgttt gaccaccctg gagcccatgga gctggcggag | 480 | |

```
catctcacct acttggagta tcgctccttc tgcaagatcc tgtttcagga ctatcacagt    540
ttcgtgactc atggctgcac tgtggacaac cccgtcctgg agcggttcat ctccctcttc    600
aacagcgtct cacagtgggt gcagctcatg atcctcagca aacccacagc ccgcagcgg    660 gccctggtca tcacacactt tgtccacgtg cggagaagc tgctacagct gcagaacttc    720
aacacgctga tggcagtggt cggggcctg agccacagct ccatctcccg cctcaaggag    780
acccacagcc acgttagccc tgagaccatc aagctctggg agggtctcac ggaactagtg    840
acggcgacag gcaactatgg caactaccgg cgtcggctgg cagcctgtgt gggcttccgc    900
ttcccgatcc tgggtgtgca cctcaaggac ctggtggccc tgcagctggc actgcctgac    960
tggctggacc cagcccggac ccggctcaac ggggccaaga tgaagcagct ctttagcatc   1020
ctggaggagc tggccatggt gaccagcctg cggccaccag tacaggccaa ccccgacctg   1080
ctgagcctgc tcacggtgtc tctggatcag tatcagacgg aggatgagct gtaccagctg   1140
tccctgcagc gggagccgcg ctccaagtcc tcgccaacca gccccacgag ttgcacccca   1200
ccaccccggc ccccggtact ggaggagtgg acctcggctg ccaaacccaa gctggatcag   1260
gccctcgtgg tggagcacat cgagaagatg gtggagggat ggctgcatca gcagggagga   1320
gatggtttcc tatttcctgc gctccagctc tgtgttgggg gggcgcatgg gcttcgtaca   1380
caacttccag gagagcaact ccttgcgccc cgtcgcctgc cgccactgca aagccctgat   1440
cctgggcatc tacaagcagg gcctcaaatg ccgagcctgt ggagtgaact gccacaagca   1500
gtgcaaggat cgcctgtcag ttgagtgtcg gcgcagggcc cagagtgtga gcctggaggg   1560
gtctgcaccc tcaccctcac ccatgcacag ccaccatcac cgcgccttca gcttctctct   1620
gccccgccct ggcaggcgag gctccaggcc tccagagatc cgtgaggagg aggtacagac   1680
ggtggaggat ggggtgtttg acatccactt gtaa                               1714
```

<210> SEQ ID NO 50
<211> LENGTH: 19
<212> TYPE: RNA
<213> ORGANISM: Artificial Sequence
<220> FEATURE:
<223> OTHER INFORMATION: Synthetic

<400> SEQUENCE: 50
gguggaggga uggcugcau                                                  19

<210> SEQ ID NO 51
<211> LENGTH: 19
<212> TYPE: RNA
<213> ORGANISM: Artificial Sequence
<220> FEATURE:
<223> OTHER INFORMATION: Synthetic

<400> SEQUENCE: 51
augcagccau cccuccacc                                                  19

<210> SEQ ID NO 52
<211> LENGTH: 3099
<212> TYPE: DNA
<213> ORGANISM: Homo sapiens

<400> SEQUENCE: 52
atggcttggg aagcgaggcg cgaacccggc ccccgaaggg ccgccgtccg ggagacggtg     60
atgctgttgc tgtgcctggg ggtcccgacc ggccgcccct acaacgtgga cactgagagc    120

```
gcgctgctttt accagggccc ccacaacacg ctgttcggct actcggtcgt gctgcacagc    180
cacggggcga accgatggct cctagtgggt gcgcccactg ccaactggct cgccaacgct    240
tcagtgatca atcccggggc gatttacaga tgcaggatcg gaaagaatcc cggccagacg    300
tgcgaacagc tccagctggg tagccctaat ggagaacctt gtggaaagac ttgtttggaa    360
gagagagaca atcagtggtt gggggtcaca cttttccagac agccaggaga aaatggatcc    420
atcgtgactt gtgggcatag atggaaaaat atattttaca taaagaatga aaataagctc    480
cccactggtg gttgctatgg agtgcccccct gatttacgaa cagaactgag taaaagaata    540
gctccgtgtt atcaagatta tgtgaaaaaa tttggagaaa attttgcatc atgtcaagct    600
ggaatatcca gttttacac aaaggattta attgtgatgg gggccccagg atcatcttac    660
tggactggct ctcttttttgt ctacaatata actacaaata aatacaaggc ttttttagac    720
aaacaaaatc aagtaaaatt tggaagttat ttaggatatt cagtcggagc tggtcatttt    780
cggagccagc atactaccga agtagtcgga ggagctcctc aacatgagca gattggtaag    840
gcatatatat tcagcattga tgaaaaagaa ctaaatatct tacatgaaat gaaaggtaaa    900
aagcttggat cgtactttgg agcttctgtc tgtgctgtgg acctcaatgc agatggcttc    960
tcagatctgc tcgtgggagc acccatgcag agcaccatca gagaggaagg aagagtgttt   1020
gtgtacatca actctggctc gggagcagta atgaatgcaa tggaaacaaa cctcgttgga   1080
agtgacaaat atgctgcaag atttggggaa tctatagtta atcttggcga cattgacaat   1140
gatggctttg aagatgttgc tatcggagct ccacaagaag atgacttgca aggtgctatt   1200
tatatttaca atggccgtgc agatgggatc tcgtcaacct tctcacagag aattgaagga   1260
cttcagatca gcaaatcgtt aagtatgttt ggacagtcta tatcaggaca aattgatgca   1320
gataataatg ctatgtaga gtagcagtt ggtgcttttc ggtctgattc tgctgtcttg   1380
ctaaggacaa gacctgtagt aattgttgac gcttctttaa gccaccctga gtcagtaaat   1440
agaacgaaat ttgactgtgt tgaaaatgga tggccttctg tgtgcataga tctaacactt   1500
tgtttctcat ataagggcaa ggaagttcca ggttacattg ttttgtttta acatgagt   1560 ttggatgtga acagaaaggc agagtctcca ccaagattct atttctcttc taatggaact   1620
tctgacgtga ttacaggaag catacaggtg tccagcagag aagctaactg tagaacacat   1680
caagcattta tgcggaaaga tgtgcgggac atcctcaccc caattcagat tgaagctgct   1740
taccaccttg gtcctcatgt catcagtaaa cgaagtacag aggaattccc accacttcag   1800
ccaattcttc agcagaagaa agaaaaagac ataatgaaaa aaacaataaa ctttgcaagg   1860
ttttgtgccc atgaaaattg ttctgctgat ttacaggttt ctgcaaagat tgggtttttg   1920
aagccccatg aaaataaaac atatcttgct gttgggagta tgaagacatt gatgttgaat   1980
gtgtccttgt ttaatgctgg agatgatgca tatgaaacga ctctacatgt caaactaccc   2040
gtgggtcttt atttcattaa gattttagag ctggaagaga agcaaataaa ctgtgaagtc   2100
acagataact ctggcgtggt acaacttgac tgcagtattg ctatatata tgtagatcat   2160 ctctcaagga tagatattag cttttctcctg gatgtgagct cactcagcag agcggaagag   2220
gacctcagta tcacagtgca tgctacctgt gaaaatgaag aggaaatgga caatctaaag   2280
cacagcagag tgactgtagc aataccttta aaatatgagg ttaagctgac tgttcatggg   2340
tttgtaaacc caacttcatt tgtgtatgga tcaaatgatg aaaatgagcc tgaaacgtgc   2400
atggtggaga aaatgaactt aactttccat gttatcaaca ctggcaatag tatggctccc   2460
aatgttagtg tggaaataat ggtaccaaat tcttttagcc cccaaactga taagctgttc   2520
```

-continued

```
aacattttgg atgtccagac tactactgga gaatgccact ttgaaaatta tcaaagagtg   2580
tgtgcattag agcagcaaaa gagtgcaatg cagaccttga aaggcatagt ccggttcttg   2640
tccaagactg ataagaggct attgtactgc ataaaagctg atccacattg tttaaatttc   2700
ttgtgtaatt ttgggaaaat ggaaagtgga aagaagcca gtgttcatat ccaactggaa   2760
ggccggccat ccattttaga aatggatgag acttcagcac tcaagtttga aataagagca   2820
acaggttttc cagagccaaa tccaagagta attgaactaa acaaggatga gaatgttgcg   2880
catgttctac tggaaggact acatcatcaa agacccaaac gttatttcac catagtgatt   2940
atttcaagta gcttgctact tggacttatt gtacttctat tgatctcata tgttatgtgg   3000
aaggctggct tctttaaaag acaatacaaa tctatcctac aagaagaaaa cagaagagac   3060
agttggagtt atatcaacag taaaagcaat gatgattaa                          3099
```

<210> SEQ ID NO 53
<211> LENGTH: 21
<212> TYPE: DNA
<213> ORGANISM: Artificial Sequence
<220> FEATURE:
<223> OTHER INFORMATION: Synthetic

<400> SEQUENCE: 53
tcttgctgtt gggagtatga a                                             21

<210> SEQ ID NO 54
<211> LENGTH: 21
<212> TYPE: DNA
<213> ORGANISM: Artificial Sequence
<220> FEATURE:
<223> OTHER INFORMATION: Synthetic

<400> SEQUENCE: 54
tgatactgag gtcctcttcc g                                             21

<210> SEQ ID NO 55
<211> LENGTH: 19
<212> TYPE: RNA
<213> ORGANISM: Artificial Sequence
<220> FEATURE:
<223> OTHER INFORMATION: Synthetic

<400> SEQUENCE: 55
gggaguauga agacauuga                                                19

<210> SEQ ID NO 56
<211> LENGTH: 19
<212> TYPE: RNA
<213> ORGANISM: Artificial Sequence
<220> FEATURE:
<223> OTHER INFORMATION: Synthetic

<400> SEQUENCE: 56
ucaaugucuu cauacuccc                                                19

<210> SEQ ID NO 57
<211> LENGTH: 21
<212> TYPE: DNA
<213> ORGANISM: Artificial Sequence
<220> FEATURE:
<223> OTHER INFORMATION: Synthetic

<400> SEQUENCE: 57
gggtttttga agaagagaag c                                          21

<210> SEQ ID NO 58
<211> LENGTH: 2948
<212> TYPE: DNA
<213> ORGANISM: Homo sapiens

<400> SEQUENCE: 58

| | | | | | |
|---|---|---|---|---|---|
| atggcttggg | aagcgaggcg | cgaacccggc | ccccgaaggg | ccgccgtccg | ggagacggtg | 60 |
| atgctgttgc | tgtgcctggg | ggtcccgacc | ggccgcccct | acaacgtgga | cactgagagc | 120 |
| gcgctgcttt | accagggccc | ccacaacacg | ctgttcggct | actcggtcgt | gctgcacagc | 180 |
| cacggggcga | accgatggct | cctagtgggt | gcgcccactg | ccaactggct | cgccaacgct | 240 |
| tcagtgatca | atcccggggc | gatttacaga | tgcaggatcg | gaaagaatcc | cggccagacg | 300 |
| tgcgaacagc | tccagctggg | tagccctaat | ggagaacctt | gtggaaagac | ttgtttggaa | 360 |
| gagagagaca | tcagtggtt | gggggtcaca | ctttccagac | agccaggaga | aaatggatcc | 420 |
| atcgtgactt | gtgggcatag | atggaaaaat | atattttaca | taaagaatga | aaataagctc | 480 |
| cccactggtg | gttgctatgg | agtgccccct | gatttacgaa | cagaactgag | taaaagaata | 540 |
| gctccgtgtt | atcaagatta | tgtgaaaaaa | tttggagaaa | attttgcatc | atgtcaagct | 600 |
| ggaatatcca | gttttttacac | aaaggattta | attgtgatgg | gggccccagg | atcatcttac | 660 |
| tggactggct | ctcttttttgt | ctacaatata | actacaaata | aatacaaggc | ttttttagac | 720 |
| aaacaaaatc | aagtaaaatt | tggaagttat | ttaggatatt | cagtcggagc | tggtcatttt | 780 |
| cggagccagc | atactaccga | agtagtcgga | ggagctcctc | aacatgagca | gattggtaag | 840 |
| gcatatatat | tcagcattga | tgaaaaagaa | ctaaatatct | tacatgaaat | gaaaggtaaa | 900 |
| aagcttggat | cgtactttgg | agcttctgtc | tgtgctgtgg | acctcaatgc | agatggcttc | 960 |
| tcagatctgc | tcgtgggagc | acccatgcag | agcaccatca | gagaggaagg | aagagtgttt | 1020 |
| gtgtacatca | actctggctc | gggagcagta | atgaatgcaa | tggaaacaaa | cctcgttgga | 1080 |
| agtgacaaat | atgctgcaag | atttgggaa | tctatagtta | atcttggcga | cattgacaat | 1140 |
| gatggctttg | aagatgttgc | tatcggagct | ccacaagaag | atgacttgca | aggtgctatt | 1200 |
| tatatttaca | atggccgtgc | agatgggatc | tcgtcaacct | tctcacagag | aattgaagga | 1260 |
| cttcagatca | gcaaatcgtt | aagtatgttt | ggacagtcta | tatcaggaca | aattgatgca | 1320 |
| gataataatg | ctatgtaga | tgtagcagtt | ggtgcttttc | ggtctgattc | tgctgtcttg | 1380 |
| ctaaggacaa | gacctgtagt | aattgttgac | gcttctttaa | gccaccctga | gtcagtaaat | 1440 |
| agaacgaaat | ttgactgtgt | tgaaaatgga | tggccttctg | tgtgcataga | tctaacactt | 1500 |
| tgtttctcat | ataagggcaa | ggaagttcca | ggttacattg | ttttgttttta | taacatgagt | 1560 |
| ttggatgtga | acagaaaggc | agagtctcca | ccaagattct | atttctcttc | taatggaact | 1620 |
| tctgacgtga | ttacaggaag | catacaggtg | tccagcagag | aagctaactg | tagaacacat | 1680 |
| caagcatttta | tgcggaaaga | tgtgcgggac | atcctcaccc | caattcagat | tgaagctgct | 1740 |
| taccaccttg | gtcctcatgt | catcagtaaa | cgaagtacag | aggaattccc | accacttcag | 1800 |
| ccaattcttc | agcagaagaa | agaaaaagac | ataatgaaaa | aaacaataaa | ctttgcaagg | 1860 |
| ttttgtgccc | atgaaaattg | ttctgctgat | ttacaggttt | ctgcaaagat | tgggttttttg | 1920 |
| aagaagagaa | gcaaataaac | tgtgaagtca | cagataactc | tggcgtggta | caacttgact | 1980 |
| gcagtattgg | ctatatatat | gtagatcatc | tctcaaggat | agatattagc | tttctcctgg | 2040 |
| atgtgagctc | actcagcaga | gcggaagagg | acctcagtat | cacagtgcat | gctacctgtg | 2100 |

-continued

```
aaaatgaaga ggaaatggac aatctaaagc acagcagagt gactgtagca atacctttaa    2160
aatatgaggt taagctgact gttcatgggt ttgtaaaccc aacttcattt gtgtatggat    2220
caaatgatga aaatgagcct gaaacgtgca tggtggagaa aatgaactta actttccatg    2280
ttatcaacac tggcaatagt atggctccca atgttagtgt ggaaataatg gtaccaaatt    2340
cttttagccc ccaaactgat aagctgttca acattttgga tgtccagact actactggag    2400
aatgccactt tgaaaattat caagagtgt gtgcattaga gcagcaaaag agtgcaatgc    2460
agaccttgaa aggcatagtc cggttcttgt ccaagactga taagaggcta ttgtactgca    2520
taaaagctga tccacattgt ttaaatttct tgtgtaattt tgggaaaatg gaaagtggaa    2580
aagaagccag tgttcatatc caactggaag gccggccatc cattttagaa atggatgaga    2640
cttcagcact caagtttgaa ataagagcaa caggttttcc agagccaaat ccaagagtaa    2700
ttgaactaaa caaggatgag aatgttgcgc atgttctact ggaaggacta catcatcaaa    2760
gacccaaacg ttatttcacc atagtgatta tttcaagtag cttgctactt ggacttattg    2820
tacttctatt gatctcatat gttatgtgga aggctggctt cttaaaaga caatacaaat    2880 ctatcctaca agaagaaaac agaagagaca gttggagtta tatcaacagt aaaagcaatg    2940
atgattaa                                                           2948

<210> SEQ ID NO 59
<211> LENGTH: 19
<212> TYPE: RNA
<213> ORGANISM: Artificial Sequence
<220> FEATURE:
<223> OTHER INFORMATION: Synthetic

<400> SEQUENCE: 59
gaagaagaga agcaaauaa                                                  19

<210> SEQ ID NO 60
<211> LENGTH: 19
<212> TYPE: RNA
<213> ORGANISM: Artificial Sequence
<220> FEATURE:
<223> OTHER INFORMATION: Synthetic

<400> SEQUENCE: 60
uuauuugcuu cucuucuuc                                                  19

<210> SEQ ID NO 61
<211> LENGTH: 19
<212> TYPE: DNA
<213> ORGANISM: Artificial Sequence
<220> FEATURE:
<223> OTHER INFORMATION: Synthetic

<400> SEQUENCE: 61
ctggaaatta agggaaatg                                                  19

<210> SEQ ID NO 62
<211> LENGTH: 4226
<212> TYPE: DNA
<213> ORGANISM: Homo sapiens

<400> SEQUENCE: 62
atgaaggccc ccgctgtgct tgcacctggc atcctcgtgc tcctgtttac cttggtgcag      60
aggagcaatg ggagtgtaaa gaggcactag caaagtccga gatgaatgtg aatatgaagt     120
```

```
atcagcttcc caacttcacc gcggaaacac ccatccagaa tgtcattcta catgagcatc    180
acattttcct tggtgccact aactacattt atgttttaaa tgaggaagac cttcagaagg    240
ttgctgagta caagactggg cctgtgctgg aacacccaga ttgtttccca tgtcaggact    300
gcagcagcaa agccaattta tcaggaggtg tttggaaaga taacatcaac atggctctag    360
ttgtcgacac ctactatgat gatcaactca ttagctgtgg cagcgtcaac agagggacct    420
gccagcgaca tgtctttccc cacaatcata ctgctgacat acagtcggag gttcactgca    480
tattctcccc acagatagaa gagcccagcc agtgtcctga ctgtgtggtg agcgccctgg    540
gagccaaagt cctttcatct gtaaaggacc ggttcatcaa cttctttgta ggcaatacca    600
taaattcttc ttatttccca gatcatccat tgcattcgat atcagtgaga aggctaaagg    660
aaacgaaaga tggttttatg tttttgacgg accagtccta cattgatgtt ttacctgagt    720
tcagagattc ttaccccatt aagtatgtcc atgcctttga agcaacaat tttatttact    780 tcttgacggt ccaaagggaa actctagatg ctcagacttt tcacacaaga ataatcaggt    840
tctgttccat aaactctgga ttgcattcct acatggaaat gcctctggag tgtattctca    900
cagaaaagag aaaaaagaga tccacaaaga aggaagtgtt taatatactt caggctgcgt    960
atgtcagcaa gcctggggcc cagcttgcta gacaaatagg agccagcctg aatgatgaca   1020
ttcttttcgg ggtgttcgca caaagcaagc cagattctgc cgaaccaatg gatcgatctg   1080
ccatgtgtgc attccctatc aaatatgtca acgacttctt caacaagatc gtcaacaaaa   1140
acaatgtgag atgtctccag cattttacg gacccaatca tgagcactgc tttaatagga   1200
cacttctgag aaaattcatc ggctgtgaag cgcgccgtga tgaatatcga acagagttta   1260
ccacagcttt gcagcgcgtt gacttattca tgggtcaatt cagcgaagtc ctcttaacat   1320
ctatatccac cttcattaaa ggagacctca ccatagctaa tcttgggaca tcagagggtc   1380
gcttcatgca ggttgtggtt tctcgatcag gaccatcaac ccctcatgtg aatttttctcc   1440 tggactccca tccagtgtct ccagaagtga ttgtggagca tacattaaac caaaatggct   1500
acacactggt tatcactggg aagaagatca cgaagatccc attgaatggc ttgggctgca   1560
gacatttcca gtcctgcagt caatgcctct ctgccccacc ctttgttcag tgtggctggt   1620
gccacgacaa atgtgtgcga tcggaggaat gcctgagcgg acatggact caacagatct   1680 gtctgcctgc aatctacaag gttttcccaa atagtgcacc ccttgaagga gggacaaggc   1740
tgaccatatg tggctgggac tttggatttc ggaggaataa taaatttgat ttaaagaaaa   1800
ctagagttct ccttggaaat gagagctgca ccttgacttt aagtgagagc acgatgaata   1860
cattgaaatg cacagttggt cctgccatga ataagcattt caatatgtcc ataattattt   1920
caaatggcca cggacaaca caatacagta cattctccta tgtggatcct gtaataacaa   1980
gtatttcgcc gaaatacggt cctatggctg gtggcacttt acttactta actgaaaatt   2040 acctaaacag tgggaattct agacacattt caattggtgg aaaaacatgt actttaaaaa   2100
gtgtgtcaaa cagtattctt gaatgttata ccccagccca aaccatttca actgagtttg   2160
ctgttaaatt gaaaattgac ttagccaacc gagagacaag catcttcagt taccgtgaag   2220
atcccattgt ctatgaaatt catccaacca aatctttat tagtacttgg tggaaagaac   2280
ctctcaacat tgtcagtttt ctattttgct ttgccagtgg tgggagcaca ataacaggtg   2340
ttgggaaaaa cctgaattca gttagtgtcc cgagaatggt cataaatgtg catgaagcag   2400
gaaggaactt tacagtggca tgtcaacatc gctctaattc agagataatc tgttgtacca   2460
ctccttccct gcaacagctg aatctgcaac tcccctgaa aaccaaagcc tttttcatgt   2520
```

```
tagatgggat cctttccaaa tactttgatc tcatttatgt acataatcct gtgtttaagc    2580
cttttgaaaa gccagtgatg atctcaatgg gcaatgaaaa tgtactggaa attaagggaa    2640
atgatattga ccctgaagca gttaaaggtg aagtgttaaa agttggaaat aagagctgtg    2700
agaatataca cttacattct gaagccgttt tatgcacggt ccccaatgac ctgctgaaat    2760
tgaacagcga gctaaatata gagtggaagc aagcaatttc ttcaaccgtc cttggaaaag    2820
taatagttca accagatcag aatttcacag gattgattgc tggtgttgtc tcaatatcaa    2880
cagcactgtt attactactt gggttttttcc tgtggctgaa aaagagaaag caaattaaag    2940
atctgggcag tgaattagtt cgctacgatg caagagtaca cactcctcat ttggataggc    3000
ttgtaagtgc ccgaagtgta agcccaacta cagaaatggt ttcaaatgaa tctgtagact    3060
accgagctac ttttccagaa gatcagtttc ctaattcatc tcagaacggt tcatgccgac    3120
aagtgcagta tcctctgaca gacatgtccc ccatcctaac tagtggggac tctgatatat    3180
ccagtccatt actgcaaaat actgtccaca ttgacctcag tgctctaaat ccagagctgg    3240
tccaggcagt gcagcatgta gtgattgggc ccagtagcct gattgtgcat ttcaatgaag    3300
tcataggaag agggcatttt ggttgtgtat atcatgggac tttgttggac aatgatggca    3360
agaaaattca ctgtgctgtg aaatccttga acagaatcac tgacatagga gaagtttccc    3420
aatttctgac cgagggaatc atcatgaaag attttagtca tcccaatgtc ctctcgctcc    3480
tgggaatctg cctgcgaagt gaagggtctc cgctggtggt cctaccatac atgaaacatg    3540
gagatcttcg aaatttcatt cgaaatgaga ctcataatcc aactgtaaaa gatcttattg    3600
gctttggtct tcaagtagcc aaaggcatga atatcttgc aagcaaaaag tttgtccaca    3660
gagacttggc tgcaagaaac tgtatgctgg atgaaaaatt cacagtcaag gttgctgatt    3720
ttggtcttgc cagagacatg tatgataaag aatactatag tgtacacaac aaaacaggtg    3780
caaagctgcc agtgaagtgg atggctttgg aaagtctgca aactcaaaag tttaccacca    3840
agtcagatgt gtggtccttt ggcgtgctcc tctgggagct gatgacaaga ggagccccac    3900
cttatcctga cgtaaacacc tttgatataa ctgtttactt gttgcaaggg agaagactcc    3960
tacaacccga atactgccca gacccttat atgaagtaat gctaaaatgc tggcacccta    4020
aagccgaaat gcgcccatcc ttttctgaac tggtgtcccg gatatcagcg atcttctcta    4080 cttttcattgg ggagcactat gtccatgtga acgctactta tgtgaacgta aaatgtgtcg    4140
ctccgtatcc ttctctgttg tcatcagaag ataacgctga tgatgaggtg gacacacgac    4200
cagcctcctt ctgggagaca tcatag                                        4226
```

<210> SEQ ID NO 63
<211> LENGTH: 19
<212> TYPE: RNA
<213> ORGANISM: Artificial Sequence
<220> FEATURE:
<223> OTHER INFORMATION: Synthetic

<400> SEQUENCE: 63
guacuggaaa uuaagggaa                                                   19

<210> SEQ ID NO 64
<211> LENGTH: 19
<212> TYPE: RNA
<213> ORGANISM: Artificial Sequence
<220> FEATURE:
<223> OTHER INFORMATION: Synthetic

<400> SEQUENCE: 64
uucccuuaau uuccaguac                                                    19

<210> SEQ ID NO 65
<211> LENGTH: 4651
<212> TYPE: DNA
<213> ORGANISM: Homo sapiens

<400> SEQUENCE: 65

| | | | | | |
|---|---|---|---|---|---|
| atgaaggccc | ccgctgtgct | tgcacctggc | atcctcgtgc | tcctgtttac | cttggtgcag | 60 |
| aggagcaatg | ggagtgtaaa | gaggcactag | caaagtccga | gatgaatgtg | aatatgaagt | 120 |
| atcagcttcc | caacttcacc | gcggaaacac | ccatccagaa | tgtcattcta | catgagcatc | 180 |
| acattttcct | tggtgccact | aactacattt | atgttttaaa | tgaggaagac | cttcagaagg | 240 |
| ttgctgagta | caagactggg | cctgtgctgg | aacacccaga | ttgtttccca | tgtcaggact | 300 |
| gcagcagcaa | agccaattta | tcaggaggtg | tttggaaaga | taacatcaac | atggctctag | 360 |
| ttgtcgacac | ctactatgat | gatcaactca | ttagctgtgg | cagcgtcaac | agagggacct | 420 |
| gccagcgaca | tgtctttccc | cacaatcata | ctgctgacat | acagtcggag | gttcactgca | 480 |
| tattctcccc | acagatagaa | gagcccagcc | agtgtcctga | ctgtgtggtg | agcgccctgg | 540 |
| gagccaaagt | cctttcatct | gtaaaggacc | ggttcatcaa | cttctttgta | ggcaatacca | 600 |
| taaattcttc | ttatttccca | gatcatccat | gcattcgat | atcagtgaga | aggctaaagg | 660 |
| aaacgaaaga | tggttttatg | tttttgacgg | accagtccta | cattgatgtt | ttacctgagt | 720 |
| tcagagattc | ttacccccatt | aagtatgtcc | atgcctttga | aagcaacaat | tttatttact | 780 |
| tcttgacggt | ccaaagggaa | actctagatg | ctcagacttt | tcacacaaga | ataatcaggt | 840 |
| tctgttccat | aaactctgga | ttgcattcct | acatggaaat | gcctctggag | tgtattctca | 900 |
| cagaaaagag | aaaaaagaga | tccacaaaga | aggaagtgtt | taatatactt | caggctgcgt | 960 |
| atgtcagcaa | gcctgggggcc | cagcttgcta | gacaaatagg | agccagcctg | aatgatgaca | 1020 |
| ttctttttcgg | ggtgttcgca | caaagcaagc | cagattctgc | cgaaccaatg | gatcgatctg | 1080 |
| ccatgtgtgc | attccctatc | aaatatgtca | acgacttctt | caacaagatc | gtcaacaaaa | 1140 |
| acaatgtgag | atgtctccag | catttttacg | gacccaatca | tgagcactgc | tttaatagga | 1200 |
| cacttctgag | aaaattcatca | ggctgtgaag | cgcgccgtga | tgaatatcga | acagagttta | 1260 |
| ccacagcttt | gcagcgcgtt | gacttattca | tgggtcaatt | cagcgaagtc | ctcttaacat | 1320 |
| ctatatccac | cttcattaaa | ggagacctca | ccatagctaa | tcttgggaca | tcagagggtc | 1380 |
| gcttcatgca | ggttgtggtt | tctcgatcag | gaccatcaac | ccctcatgtg | aattttctcc | 1440 |
| tggactccca | tccagtgtct | ccagaagtga | ttgtggagca | tacattaaac | caaaatggct | 1500 |
| acacactggt | tatcactggg | aagaagatca | cgaagatccc | attgaatggc | ttgggctgca | 1560 |
| gacatttcca | gtcctgcagt | caatgcctct | ctgccccacc | ctttgttcag | tgtggctggt | 1620 |
| gccacgacaa | atgtgtgcga | tcggaggaat | gcctgagcgg | gacatggact | caacagatct | 1680 |
| gtctgcctgc | aatctacaag | gttttcccaa | atagtgcacc | ccttgaagga | gggacaaggc | 1740 |
| tgaccatatg | tggctgggac | tttgattttc | ggaggaataa | taaatttgat | taaagaaaa | 1800 |
| ctagagttct | ccttggaaat | gagagctgca | ccttgacttt | aagtgagagc | acgatgaata | 1860 |
| cattgaaatg | cacagttggt | cctgccatga | taagcatt | caatatgtcc | ataattattt | 1920 |
| caaatggcca | cgggacaaca | caatacagta | cattctccta | tgtggatcct | gtaataacaa | 1980 |
| gtatttcgcc | gaaatacggt | cctatggctg | gtggcacttt | acttacttta | actggaaatt | 2040 |

```
acctaaacag tgggaattct agacacattt caattggtgg aaaaacatgt actttaaaaa    2100
gtgtgtcaaa cagtattctt gaatgttata ccccagccca aaccatttca actgagtttg    2160
ctgttaaatt gaaaattgac ttagccaacc gagagacaag catcttcagt taccgtgaag    2220
atcccattgt ctatgaaatt catccaacca aatcttttat tagtacttgg tggaaagaac    2280
ctctcaacat tgtcagtttt ctattttgct ttgccagtgg tgggagcaca ataacaggtg    2340
ttgggaaaaa cctgaattca gttagtgtcc cgagaatggt cataaatgtg catgaagcag    2400
gaaggaactt tacagtggca tgtcaacatc gctctaattc agagataatc tgttgtacca    2460
ctccttccct gcaacagctg aatctgcaac tcccccctgaa aaccaaagcc tttttcatgt    2520
tagatgggat cctttccaaa tactttgatc tcatttatgt acataatcct gtgtttaagc    2580
cttttgaaaa gccagtgatg atctcaatgg gcaatgaaaa tgtactggaa attaaggtgg    2640
gagcagtggc aattcaggga gattatttta gtatcatggt tcaatatttt ttcatacttc    2700
atttttctta tgtatgagag gaaagcaaag gcataagaga atatttgttg tgtcagcaat    2760
ctaactcttt atcaatacgt taagttgatc acattaaaac ttctacctct cagccaggca    2820
cggtagctca tacctgtaat cccagcactt tgggaggcca aggcgggtga atcacttgag    2880
atcaggagtt caagaccagc ctggccaaaa tggtgaaacc ccatctccac taaaaataca    2940
aaaattagct gggcatggtg gtgggtgcct gtaatcccag ctactcagga ggctgaggga    3000
cggaggtgac ctgagtcctg aaggcggagg ttgcagtgag ccaagatggc accactgcac    3060
tggaaatgat attgaccctg aagcagttaa aggtgaagtg ttaaaagttg gaataagag    3120
ctgtgagaat atacacttac attctgaagc cgttttatgc acggtcccca atgacctgct    3180
gaaattgaac agcgagctaa atatagagtg gaagcaagca atttcttcaa ccgtccttgg    3240
aaaagtaata gttcaaccag atcagaattt cacaggattg attgctggtg ttgtctcaat    3300
atcaacagca ctgttattac tacttgggtt tttcctgtgg ctgaaaaaga gaaagcaaat    3360
taaagatctg ggcagtgaat tagttcgcta cgatgcaaga gtacacactc ctcatttgga    3420
taggcttgta agtgcccgaa gtgtaagccc aactacagaa atggtttcaa atgaatctgt    3480
agactaccga gctacttttc cagaagatca gtttcctaat tcatctcaga acggttcatg    3540
ccgacaagtg cagtatcctc tgacagacat gtcccccatc ctaactagtg gggactctga    3600
tatatccagt ccattactgc aaaatactgt ccacattgac ctcagtgctc taaatccaga    3660
gctggtccag gcagtgcagc atgtagtgat tgggcccagt agcctgattg tgcatttcaa    3720
tgaagtcata ggaagagggc attttggttg tgtatatcat gggactttgt tggacaatga    3780
tggcaagaaa attcactgtg ctgtgaaatc cttgaacaga atcactgaca taggagaagt    3840
ttcccaattt ctgaccgagg gaatcatcat gaaagatttt agtcatccca atgtcctctc    3900
gctcctggga atctgcctgc gaagtgaagg gtctccgctg gtggtcctac catacatgaa    3960
acatggagat cttcgaaatt tcattcgaaa tgagactcat aatccaactg taaaagatct    4020
tattggcttt ggtcttcaag tagccaaagg catgaaatat cttgcaagca aaagtttgt    4080
ccacagagac ttggctgcaa gaaactgtat gctggatgaa aaattcacag tcaaggttgc    4140
tgattttggt cttgccagag acatgtatga taaagaatac tatagtgtac acaacaaaac    4200
aggtgcaaag ctgccagtga agtggatggc tttggaaagt ctgcaaactc aaaagtttac    4260
caccaagtca gatgtgtggt cctttggcgt gctcctctgg gagctgatga caagaggagc    4320
cccaccttat cctgacgtaa acacctttga tataactgtt tacttgttgc aagggagaag    4380
```

```
actcctacaa cccgaatact gcccagaccc cttatatgaa gtaatgctaa aatgctggca    4440
ccctaaagcc gaaatgcgcc catccttttc tgaactggtg tcccggatat cagcgatctt    4500
ctctactttc attggggagc actatgtcca tgtgaacgct acttatgtga acgtaaaatg    4560
tgtcgctccg tatccttctc tgttgtcatc agaagataac gctgatgatg aggtggacac    4620
acgaccagcc tccttctggg agacatcata g                                  4651
```

<210> SEQ ID NO 66
<211> LENGTH: 20
<212> TYPE: DNA
<213> ORGANISM: Artificial Sequence
<220> FEATURE:
<223> OTHER INFORMATION: Synthetic

<400> SEQUENCE: 66

```
tggtggaaag aacctctcaa                                                 20
```

<210> SEQ ID NO 67
<211> LENGTH: 20
<212> TYPE: DNA
<213> ORGANISM: Artificial Sequence
<220> FEATURE:
<223> OTHER INFORMATION: Synthetic

<400> SEQUENCE: 67

```
atcttggctc actgcaacct                                                 20
```

<210> SEQ ID NO 68
<211> LENGTH: 19
<212> TYPE: RNA
<213> ORGANISM: Artificial Sequence
<220> FEATURE:
<223> OTHER INFORMATION: Synthetic

<400> SEQUENCE: 68

```
cagcaaucua acucuuuau                                                  19
```

<210> SEQ ID NO 69
<211> LENGTH: 19
<212> TYPE: RNA
<213> ORGANISM: Artificial Sequence
<220> FEATURE:
<223> OTHER INFORMATION: Synthetic

<400> SEQUENCE: 69

```
auaaagaguu agauugcug                                                  19
```

<210> SEQ ID NO 70
<211> LENGTH: 8520
<212> TYPE: DNA
<213> ORGANISM: Homo sapiens

<400> SEQUENCE: 70

```
atggccgcgc acaggccggt ggaatgggtc caggccgtgg tcagccgctt cgacgagcag      60
cttccaataa aaacaggaca gcagaacaca cataccaaag tcagtactga gcacaacaag     120
gaatgtctaa tcaatatttc caaatacaag ttttctttgg ttataagcgg cctcactact     180
attttaaaga atgttaacaa tatgagaata tttggagaag ctgctgaaaa aaatttatat     240
ctctctcagt tgattatatt ggatacactg gaaaaatgtc ttgctgggca accaaaggac     300
acaatgagat tagatgaaac gatgctggtc aaacagttgc tgccagaaat ctgccatttt     360
cttcacacct gtcgtgaagg aaaccagcat gcagctgaac ttcggaattc tgcctctggg     420
```

```
gttttatttt ctctcagctg caacaacttc aatgcagtct ttagtcgcat ttctaccagg    480
ttacaggaat taactgtttg ttcagaagac aatgttgatg ttcatgatat agaattgtta    540
cagtatatca atgtggattg tgcaaaatta aaacgactcc tgaaggaaac agcatttaaa    600
tttaaagccc taaagaaggt tgcgcagtta gcagttataa atagcctgga aaaggcattt    660
tggaactggg tagaaaatta tccagatgaa tttacaaaac tgtaccagat cccacagact    720
gatatggctg aatgtgcaga aaagctattt gacttggtgg atggttttgc tgaaagcacc    780
aaacgtaaag cagcagtttg gccactacaa atcattctcc ttatcttgtg tccagaaata    840
atccaggata tatccaaaga cgtggttgat gaaaacaaca tgaataagaa gttatttctg    900
gacagtctac gaaaagctct tgctggccat ggaggaagta ggcagctgac agaaagtgct    960
gcaattgcct gtgtcaaact gtgtaaagca agtacttaca tcaattggga agataactct   1020
gtcattttcc tacttgttca gtccatggtg gttgatctta agaacctgct ttttaatcca   1080
agtaagccat tctcaagagg cagtcagcct gcagatgtgg atctaatgat tgactgcctt   1140
gtttcttgct ttcgtataag ccctcacaac aaccaacact ttaagatctg cctggctcag   1200
aattcacctt ctacatttca ctatgtgctg gtaaattcac tccatcgaat catcaccaat   1260
tccgcattgg attggtggcc taagattgat gctgtgtatt gtcactcggt tgaacttcga   1320
aatatgtttg gtgaaacact tcataaagca gtgcaaggtt gtggagcaca cccagcaata   1380
cgaatggcac cgagtcttac atttaaagaa aaagtaacaa gccttaaatt taagaaaaaa   1440
cctacagacc tggagacaag aagctataag tatcttctct tgtccatggt gaaactaatt   1500
catgcagatc caaagctctt gctttgtaat ccaagaaaac aggggcccga acccaaggc    1560 agtacagcag aattaattac agggctcgtc caactggtcc ctcagtcaca catgccagag   1620
attgctcagg aagcaatgga ggctctgctg gttcttcatc agttagatag cattgatttg   1680
tggaatcctg atgctcctgt agaaacattt gggagatta gctcacaaat gcttttttac    1740
atctgcaaga aattaactag tcatcaaatg cttagtagca cagaaattct caagtggttg   1800
cgggaaatat tgatctgcag gaataaattt cttcttaaaa ataagcaggc agatagaagt   1860
tcctgtcact ttctcctttt ttacggggta ggatgtgata ttccttctag tggaaatacc   1920
agtcaaatgt ccatggatca tgaagaatta ctacgtactc ctggagcctc tctccggaag   1980
ggaaaaggga actcctctat ggatagtgca gcaggatgca gcggaacccc cccgatttgc   2040
cgacaagccc agaccaaact agaagtggcc ctgtacatgt ttctgtggaa ccctgacact   2100
gaagctgttc tggttgccat gtcctgtttc cgccacctct gtgaggaagc agatatccgg   2160
tgtggggtgg atgaagtgtc agtgcataac ctcttgccca actataacac attcatggag   2220
tttgcctctg tcagcaatat gatgtcaaca ggaagagcag cacttcagaa aagagtgatg   2280
gcactgctga ggcgcattga gcatcccact gcaggaaaca ctgaggcttg ggaagataca   2340
catgcaaaat gggaacaagc aacaaagcta atccttaact atccaaaagc caaaatggaa   2400
gatggccagg ctgctgaaag ccttcacaag accattgtta agaggcgaat gtcccatgtg   2460
agtggaggag gatccataga tttgtctgac acagactccc tacaggaatg gatcaacatg   2520
actggcttcc tttgtgccct tggggagtg tgcctccagc agagaagcaa ttctggcctg    2580
gcaacctata gcccacccat gggtccagtc agtgaacgta gggttctat gatttcagtg     2640 atgtcttcag agggaaacgc agatacacct gtcagcaaat ttatggatcg gctgttgtcc   2700
ttaatggtgt gtaaccatga gaaagtggga cttcaaatac ggaccaatgt taaggatctg   2760
```

```
gtgggtctag aattgagtcc tgctctgtat ccaatgctat ttaacaaatt gaagaatacc    2820
atcagcaagt ttttgactc ccaaggacag gttttattga ctgataccaa tactcaattt    2880
gtagaacaaa ccatagctat aatgaagaac ttgctagata atcatactga aggcagctct    2940
gaacatctag ggcaagctag cattgaaaca atgatgttaa atctggtcag gtatgttcgt    3000
gtgcttggga atatggtcca tgcaattcaa ataaaaacga aactgtgtca attagttgaa    3060
gtaatgatgg caaggagaga tgacctctca ttttgccaag agatgaaatt taggaataag    3120
atggtagaat acctgacaga ctgggttatg gaacatcaa accaagcagc agatgatgat    3180
gtaaaatgtc ttacaagaga tttggaccag gcaagcatgg aagcagtagt ttcacttcta    3240
gctggtctcc ctctgcagcc tgaagaagga gatggtgtgg aattgatgga agccaaatca    3300
cagttatttc ttaaatactt cacattattt atgaaccttt tgaatgactg cagtgaagtt    3360
gaagatgaaa gtgcgcaaac aggtggcagg aaacgtggca tgtctcggag gctggcatca    3420
ctgaggcact gtacggtcct tgcaatgtca aacttactca atgccaacgt agacagtggt    3480
ctcatgcact ccataggctt aggttaccac aaggatctcc agacaagagc tacatttatg    3540
gaagttctga caaaaatcct tcaacaaggc acagaatttg acacacttgc agaaacagta    3600
ttggctgatc ggtttgagag attggtggaa ctggtcacaa tgatgggtga tcaaggagaa    3660
ctccctatag cgatggctct ggccaatgtg gttccttgtt ctcagtggga tgaactagct    3720
cgagttctgg ttactctgtt tgattctcgg catttactct accaactgct ctggaacatg    3780
ttttctaaag aagtagaatt ggcagactcc atgcagactc tcttccgagg caacagcttg    3840
gccagtaaaa taatgacatt ctgtttcaag gtatatggtg ctacctatct acaaaaactc    3900
ctggatcctt tattacgaat tgtgatcaca tcctctgatt ggcaacatgt tagctttgaa    3960
gtggatccta ccaggttaga accatcagag agccttgagg aaaaccagcg gaacctcctt    4020
cagatgactg aaaagttctt ccatgccatc atcagttcct cctcagaatt ccccccctcaa    4080 cttcgaagtg tgtgccactg tttataccag gcaacttgcc actccctact gaataaagct    4140
acagtaaaag aaaaaaagga aaacaaaaaa tcagtggtta gccagcgttt ccctcagaac    4200
agcatcggtg cagtaggaag tgccatgttc ctcagattta tcaatcctgc cattgtctca    4260
ccgtatgaag cagggatttt agataaaaag ccaccaccta gaatcgaaag gggcttgaag    4320
ttaatgtcaa agatacttca gagtattgcc aatcatgttc tcttcacaaa agaagaacat    4380
atgcggcctt tcaatgattt tgtgaaaagc aactttgatg cagcacgcag gttttttcctt    4440 gatatagcat ctgattgtcc tacaagtgat gcagtaaatc atagtctttc cttcataagt    4500
gacggcaatg tgcttgcttt acatcgtcta ctctggaaca atcaggagaa aattgggcag    4560 tatcttttcca gcaacaggga tcataaagct gttggaagac gacctttttga taagatggca    4620 acacttcttg catacctggg tcctccagag cacaaacctg tggcagatac acactggtcc    4680
agccttaacc ttaccagttc aaagtttgag gaatttatga ctaggcatca ggtacatgaa    4740
aaagaagaat tcaaggcttt gaaaacgtta agtatttttct accaagctgg gacttccaaa    4800
gctgggaatc ctattttta ttatgttgca cggaggttca aaactggtca aatcaatggt    4860
gatttgctga tataccatgt cttactgact ttaaagccat attatgcaaa gccatatgaa    4920
attgtagtgg accttaccca taccgggcct agcaatcgct ttaaaacaga ctttctctct    4980
aagtggtttg ttgttttttcc tggctttgct tacgacaacg tctccgcagt ctatatctat    5040
aactgtaact cctgggtcag ggagtacacc aagtatcatg agcggctgct gactggcctc    5100
aaaggtagca aaaggcttgt tttcatagac tgtcctggga aactggctga gcacatagag    5160
```

```
catgaacaac agaaactacc tgctgccacc ttggctttag aagaggacct gaaggtattc    5220
cacaatgctc tcaagctagc tcacaaagac accaaagttt ctattaaagt tggttctact    5280
gctgtccaag taacttcagc agagcgaaca aaagtcctag ggcaatcagt ctttctaaat    5340
gacatttatt atgcttcgga aattgaagaa atctgcctag tagatgagaa ccagttcacc    5400
ttaaccattg caaaccaggg cacgccgctc accttcatgc accaggagtg tgaagccatt    5460
gtccagtcta tcattcatat ccggacccgc tgggaactgt cacagcccga ctctatcccc    5520
caacacacca agattcggcc aaaagatgtc cctgggacac tgctcaatat cgcattactt    5580
aatttaggca gttctgaccc gagtttacgg tcagctgcct ataatcttct gtgtgcctta    5640
acttgtacct ttaatttaaa atcgagggc cagttactag agacatcagg tttatgtatc    5700
cctgccaaca cacccctctt tattgtctct attagtaaga cactggcagc caatgagcca    5760
cacctcacgt tagaattttt ggaagagtgt atttctggat ttagcaaatc tagtattgaa    5820
ttgaaacacc tttgtttgga atacatgact ccatggctgt caaatctagt tcgttttgc     5880 aagcataatg atgatgccaa acgacaaaga gttactgcta ttcttgacaa gctgataaca    5940
atgaccatca atgaaaaaca gatgtaccca tctattcaag caaaaatatg gggaagcctt    6000
gggcagatta cagatctgct tgatgttgta ctagacagtt tcatcaaaac cagtgcaaca    6060
ggtggcttgg gatcaataaa agctgaggtg atggcagata ctgctgtagc tttggcttct    6120
ggaaatgtga aattggtttc aagcaaggtt attggaagga tgtgcaaaat aattgacaag    6180
acatgcttat ctccaactcc tactttagaa caacatctta tgtgggatga tattgctatt    6240
ttagcacgct acatgctgat gctgtccttc aacaattccc ttgatgtggc agctcatctt    6300
ccctacctct tccacgttgt tactttctta gtagccacag gtccgctctc ccttagagct    6360
tccacacatg gactggtcat taatatcatt cactctctgt gtacttgttc acagcttcat    6420
tttagtgaag agaccaagca agttttgaga ctcagtctga cagagttctc attacccaaa    6480
ttttacttgc tgtttggcat tagcaaagtc aagtcagctg ctgtcattgc cttccgttcc    6540
agttaccggg acaggtcatt ctctcctggc tcctatgaga gagagacttt tgctttgaca    6600
tccttggaaa cagtcacaga agctttgttg agatcatgg aggcatgcat gagagatatt    6660
ccaacgtgca gtggctgga ccagtggaca gaactagctc aaagatttgc attccaatat    6720
aatccatccc tgcaaccaag agctcttgtt gtctttgggt gtattagcaa acgagtgtct    6780
catgggcaga taaagcagat aatccgtatt cttagcaagg cacttgagag ttgcttaaaa    6840
ggacctgaca cttacaacag tcaagttctg atagaagcta cagtaatagc actaaccaaa    6900
ttacagccac ttcttaataa ggactcgcct ctgcacaaag ccctcttttg ggtagctgtg    6960
gctgtgctgc agcttgatga ggtcaacttg tattcagcag gtaccgcact tcttgaacaa    7020
aacctgcata ctttagatag tctccgtata ttcaatgaca agagtccaga ggaagtattt    7080
atggcaatcc ggaatcctct ggagtggcac tgcaagcaaa tggatcattt tgttggactc    7140
aatttcaact ctaactttaa ctttgcattg gttggacacc ttttaaaagg gtacaggcat    7200
ccttcacctg ctattgttgc aagaacagtc agaattttac atacactact aactctggtt    7260
aacaaacaca gaaattgtga caatttgaa gtgaatacac agagcgtggc ctacttagca    7320 gcttactta cagtgtctga agaagttcga agtcgctgca gcctaaaaca tagaaagtca    7380
cttcttctta ctgatatttc aatggaaaat gttcctatgg atacatatcc cattcatcat    7440
ggtgacccct cctataggac actaaaggag actcagccat ggtcctctcc caaaggttct    7500
```

```
gaaggatacc ttgcagccac ctatccaact gtcggccaga ccagtccccg agccaggaaa    7560
tccatgagcc tggacatggg gcaaccttct caggccaaca ctaagaagtt gcttggaaca    7620
aggaaaagtt ttgatcactt gatatcagac acaaaggctc ctaaaaggca agaaatggaa    7680
tcagggatca caacacccccc caaaatgagg agagtagcag aaactgatta tgaaatggaa    7740
actcagagga tttcctcatc acaacagcac ccacatttac gtaaagtttc agtgtctgaa    7800
tcaaatgttc tcttggatga agaagtactt actgatccga agatccaggc gctgcttctt    7860
actgttctag ctacactggt aaaatatacc acagatgagt ttgatcaacg aattctttat    7920
gaatacttag cagaggccag tgttgtgttt cccaaagtct ttcctgttgt gcataatttg    7980
ttggactcta agatcaacac cctgttatca ttgtgccaag atccaaattt gttaaatcca    8040
atccatggaa ttgtgcagag tgtggtgtac catgaagaat ccccaccaca ataccaaaca    8100
tcttacctgc aaagttttgg ttttaatggc ttgtggcggt ttgcaggacc gttttcaaag    8160
caaacacaaa ttccagacta tgctgagctt attgttaagt ttcttgatgc cttgattgac    8220
acgtacctgc ctggaattga tgaagaaacc agtgaagaat ccctcctgac tcccacatct    8280
ccttaccctc ctgcactgca gagccagctt agtatcactg ccaaccttaa cctttctaat    8340
tccatgacct cacttgcaac ttcccagcat tccccaggaa tcgacaagga gaacgttgaa    8400
ctctccccta ccactggcca ctgtaacagt ggacgaactc gccacggatc cgcaagccaa    8460
gtgcagaagc aaagaagcgc tggcagtttc aaacgtaata gcattaagaa gatcgtgtga    8520
```

<210> SEQ ID NO 71
<211> LENGTH: 21
<212> TYPE: DNA
<213> ORGANISM: Artificial Sequence
<220> FEATURE:
<223> OTHER INFORMATION: Synthetic

<400> SEQUENCE: 71
gcattttgga actgggtaga a                                              21

<210> SEQ ID NO 72
<211> LENGTH: 20
<212> TYPE: DNA
<213> ORGANISM: Artificial Sequence
<220> FEATURE:
<223> OTHER INFORMATION: Synthetic

<400> SEQUENCE: 72
aaccaccatg gactgaacaa                                                20

<210> SEQ ID NO 73
<211> LENGTH: 19
<212> TYPE: RNA
<213> ORGANISM: Artificial Sequence
<220> FEATURE:
<223> OTHER INFORMATION: Synthetic

<400> SEQUENCE: 73
ccagauccca cagacugau                                                 19

<210> SEQ ID NO 74
<211> LENGTH: 19
<212> TYPE: RNA
<213> ORGANISM: Artificial Sequence
<220> FEATURE:
<223> OTHER INFORMATION: Synthetic

<400> SEQUENCE: 74
aucagucugu gggaucugg                                               19

<210> SEQ ID NO 75
<211> LENGTH: 21
<212> TYPE: DNA
<213> ORGANISM: Artificial Sequence
<220> FEATURE:
<223> OTHER INFORMATION: Synthetic

<400> SEQUENCE: 75
gcctggaaaa gaatgtgcag a                                           21

<210> SEQ ID NO 76
<211> LENGTH: 8444
<212> TYPE: DNA
<213> ORGANISM: Homo sapiens

<400> SEQUENCE: 76
atggccgcgc acaggccggt ggaatgggtc caggccgtgg tcagccgctt cgacgagcag    60
cttccaataa aaacaggaca gcagaacaca cataccaaag tcagtactga gcacaacaag   120
gaatgtctaa tcaatatttc caaatacaag ttttctttgg ttataagcgg cctcactact   180
attttaaaga atgttaacaa tatgagaata tttggagaag ctgctgaaaa aaatttatat   240
ctctctcagt tgattatatt ggatacactg gaaaaatgtc ttgctgggca accaaaggac   300
acaatgagat tagatgaaac gatgctggtc aaacagttgc tgccagaaat ctgccatttt   360
cttcacacct gtcgtgaagg aaaccagcat gcagctgaac ttcggaattc tgcctctggg   420
gttttatttt ctctcagctg caacaacttc aatgcagtct tagtcgcat ttctaccagg   480
ttacaggaat taactgtttg ttcagaagac aatgttgatg ttcatgatat agaattgtta   540
cagtatatca atgtggattg tgcaaaatta aaacgactcc tgaaggaaac agcatttaaa   600
tttaaagccc taagaaggt tgcgcagtta gcagttataa atagcctgga aaagaatgtg   660
cagaaaagct atttgacttg gtggatggtt ttgctgaaag caccaaacgt aaagcagcag   720
tttggccact acaaatcatt ctccttatct tgtgtccaga ataatccag gatatatcca   780
aagacgtggt tgatgaaaac aacatgaata agaagttatt tctggacagt ctacgaaaag   840
ctcttgctgg ccatggagga agtaggcagc tgacagaaag tgctgcaatt gcctgtgtca   900
aactgtgtaa agcaagtact tacatcaatt gggaagataa ctctgtcatt ttcctacttg   960
ttcagtccat ggtggttgat cttaagaacc tgcttttaa tccaagtaag ccattctcaa  1020
gaggcagtca gcctgcagat gtggatctaa tgattgactg ccttgttct tgctttcgta  1080
taagccctca caacaaccaa cactttaaga tctgcctggc tcagaattca ccttctacat  1140
ttcactatgt gctggtaaat tcactccatc gaatcatcac caattccgca ttggattggt  1200
ggcctaagat tgatgctgtg tattgtcact cggttgaact tcgaaatatg tttggtgaaa  1260
cacttcataa agcagtgcaa ggttgtggag cacacccagc aatacgaatg gcaccgagtc  1320
ttacatttaa agaaaaagta acaagcctta aatttaaaga aaacctaca gacctggaga  1380
caagaagcta taagtatctt ctcttgtcca tggtgaaact aattcatgca gatccaaagc  1440
tcttgctttg taatccaaga aaacagggc ccgaaaccca aggcagtaca gcagaattaa  1500
ttacagggct cgtccaactg gtccctcagt cacacatgcc agagattgct caggaagcaa  1560
tggaggctct gctggttctt catcagttag atagcattga tttgtggaat cctgatgctc  1620
ctgtagaaac attttgggag attagctcac aaatgctttt ttacatctgc aagaaattaa  1680

-continued

```
ctagtcatca aatgcttagt agcacagaaa ttctcaagtg gttgcgggaa atattgatct    1740
gcaggaataa atttcttctt aaaaataagc aggcagatag aagttcctgt cactttctcc    1800
ttttttacgg ggtaggatgt gatattcctt ctagtggaaa taccagtcaa atgtccatgg    1860
atcatgaaga attactacgt actcctggag cctctctccg aagggaaaa gggaactcct    1920
ctatggatag tgcagcagga tgcagcggaa ccccccgat ttgccgacaa gcccagacca    1980
aactagaagt ggccctgtac atgtttctgt ggaaccctga cactgaagct gttctggttg    2040
ccatgtcctg tttccgccac ctctgtgagg aagcagatat ccggtgtggg gtggatgaag    2100
tgtcagtgca taacctcttg cccaactata acacattcat ggagtttgcc tctgtcagca    2160
atatgatgtc aacaggaaga gcagcacttc agaaaagagt gatggcactg ctgaggcgca    2220
ttgagcatcc cactgcagga aacactgagg cttgggaaga tacacatgca aaatgggaac    2280
aagcaacaaa gctaatcctt aactatccaa aagccaaaat ggaagatggc caggctgctg    2340
aaagccttca caagaccatt gttaagaggc gaatgtccca tgtgagtgga ggaggatcca    2400
tagatttgtc tgacacagac tccctacagg aatggatcaa catgactggc ttcctttgtg    2460
cccttggggg agtgtgcctc cagcagagaa gcaattctgg cctggcaacc tatagcccac    2520
ccatgggtcc agtcagtgaa cgtaagggtt ctatgatttc agtgatgtct tcagagggaa    2580
acgcagatac acctgtcagc aaatttatgg atcggctgtt gtccttaatg gtgtgtaacc    2640
atgagaaagt gggacttcaa atacggacca atgttaagga tctggtgggt ctagaattga    2700
gtcctgctct gtatccaatg ctatttaaca aattgaagaa taccatcagc aagttttttg    2760
actcccaagg acaggtttta ttgactgata ccaatactca atttgtagaa caaaccatag    2820
ctataatgaa gaacttgcta gataatcata ctgaaggcag ctctgaacat ctagggcaag    2880
ctagcattga aacaatgatg ttaaatctgg tcaggtatgt tcgtgtgctt gggaatatgg    2940
tccatgcaat tcaaataaaa acgaaactgt gtcaattagt tgaagtaatg atggcaagga    3000
gagatgacct ctcattttgc caagagatga aatttaggaa taagatggta gaatacctga    3060
cagactgggt tatgggaaca tcaaaccaag cagcagatga tgatgtaaaa tgtcttacaa    3120
gagatttgga ccaggcaagc atggaagcag tagtttcact tctagctggt ctccctctgc    3180
agcctgaaga aggagatggt gtggaattga tggaagccaa atcacagtta tttcttaaat    3240
acttcacatt atttttgaatg acttttgaatg actgcagtga agttgaagat gaaagtgcgc    3300
aaacaggtgg caggaaacgt ggcatgtctc ggaggctggc atcactgagg cactgtacgg    3360
tccttgcaat gtcaaactta ctcaatgcca acgtagacag tggtctcatg cactccatag    3420
gcttaggtta ccacaaggat ctccagacaa gagctacatt tatggaagtt ctgacaaaaa    3480
tccttcaaca aggcacagaa tttgacacac ttgcagaaac agtattggct gatcggtttg    3540
agagattggt ggaactggtc acaatgatgg gtgatcaagg agaactccct atagcgatgg    3600
ctctggccaa tgtggttcct tgttctcagt gggatgaact agctcgagtt ctggttactc    3660
tgtttgattc tcggcattta ctctaccaac tgctctggaa catgttttct aaagaagtag    3720
aattggcaga ctccatgcag actctcttcc gaggcaacag cttggccagt aaaataatga    3780
cattctgttt caaggtatat ggtgctacct atctacaaaa actcctggat cctttattac    3840
gaattgtgat cacatcctct gattggcaac atgttagctt tgaagtggat cctaccaggt    3900
tagaaccatc agagagcctt gaggaaaacc agcggaacct ccttcagatg actgaaaagt    3960
tcttccatgc catcatcagt tcctcctcag aattccccc tcaacttcga agtgtgtgcc    4020
actgtttata ccaggcaact tgccactccc tactgaataa agctacagta aaagaaaaaa    4080
```

```
aggaaaacaa aaaatcagtg gttagccagc gtttccctca gaacagcatc ggtgcagtag    4140
gaagtgccat gttcctcaga tttatcaatc ctgccattgt ctcaccgtat gaagcaggga    4200
ttttagataa aaagccacca cctagaatcg aaagggggctt gaagttaatg tcaaagatac   4260
ttcagagtat tgccaatcat gttctcttca caaaagaaga acatatgcgg cctttcaatg    4320
attttgtgaa aagcaacttt gatgcagcac gcaggttttt ccttgatata gcatctgatt    4380
gtcctacaag tgatgcagta aatcatagtc tttccttcat aagtgacggc aatgtgcttg    4440
ctttacatcg tctactctgg aacaatcagg agaaaattgg gcagtatctt ccagcaaca    4500 gggatcataa agctgttgga agacgacctt ttgataagat ggcaacactt cttgcatacc    4560
tgggtcctcc agagcacaaa cctgtggcag atacacactg gtccagcctt aaccttacca    4620
gttcaaagtt tgaggaattt atgactaggc atcaggtaca tgaaaaagaa gaattcaagg    4680
ctttgaaaac gttaagtatt ttctaccaag ctgggacttc caaagctggg aatcctatt    4740 tttattatgt tgcacggagg ttcaaaactg gtcaaatcaa tggtgatttg ctgatatacc    4800
atgtcttact gactttaaag ccatattatg caaagccata tgaaattgta gtggaccta    4860 cccataccgg gcctagcaat cgcttttaaaa cagactttct ctctaagtgg tttgttgttt    4920
ttcctggctt tgcttacgac aacgtctccg cagtctatat ctataactgt aactcctggg    4980
tcagggagta caccaagtat catgagcggc tgctgactgg cctcaaaggt agcaaaaggc    5040
ttgttttcat agactgtcct gggaaactgg ctgagcacat agagcatgaa caacagaaac    5100
tacctgctgc caccttggct ttagaagagg acctgaaggt attccacaat gctctcaagc    5160
tagctcacaa agacaccaaa gtttctatta agttggttc tactgctgtc caagtaactt    5220
cagcagagcg aacaaaagtc ctagggcaat cagtctttct aaatgacatt tattatgctt    5280
cggaaattga agaaatctgc ctagtagatg agaaccagtt caccttaacc attgcaaacc    5340
agggcacgcc gctcaccttc atgcaccagg agtgtgaagc cattgtccag tctatcattc    5400
atatccggac ccgctgggaa ctgtcacagc ccgactctat cccccaacac accaagattc    5460
ggccaaaaga tgtccctggg acactgctca atatcgcatt acttaattta ggcagttctg    5520
acccgagttt acggtcagct gcctataatc ttctgtgtgc cttaacttgt acctttaatt    5580
taaaaatcga gggccagtta ctagagacat caggtttatg tatccctgcc aacaacaccc    5640
tctttattgt ctctattagt aagacactgg cagccaatga gccacacctc acgttagaat    5700
ttttggaaga gtgtatttct ggatttagca aatctagtat tgaattgaaa caccttttgtt   5760 tggaatacat gactccatgg ctgtcaaatc tagttcgttt ttgcaagcat aatgatgatg    5820
ccaaacgaca aagagttact gctattcttg acaagctgat aacaatgacc atcaatgaaa    5880
aacagatgta cccatctatt caagcaaaaa tatggggaag ccttgggcag attacagatc    5940
tgcttgatgt tgtactagac agtttcatca aaaccagtgc aacaggtggc ttgggatcaa    6000
taaaagctga ggtgatggca gatactgctg tagctttggc ttctggaaat gtgaaattgg    6060
tttcaagcaa ggttattgga aggatgtgca aaataattga caagacatgc ttatctccaa    6120
ctcctacttt agaacaacat cttatgtggg atgatattgc tattttagca cgctacatgc    6180
tgatgctgtc cttcaacaat tcccttgatg tggcagctca tcttccctac ctcttccacg    6240
ttgttacttt cttagtagcc acaggtccgc tctcccttag agcttccaca catggactgg    6300
tcattaatat cattcactct ctgtgtactt gttcacagct tcattttagt gaagagacca    6360
agcaagtttt gagactcagt ctgacagagt tctcattacc caaattttac ttgctgtttg    6420
```

| | |
|---|---|
| gcattagcaa agtcaagtca gctgctgtca ttgccttccg ttccagttac cgggacaggt | 6480 |
| cattctctcc tggctcctat gagagagaga cttttgcttt gacatccttg gaaacagtca | 6540 |
| cagaagcttt gttggagatc atggaggcat gcatgagaga tattccaacg tgcaagtggc | 6600 |
| tggaccagtg gacagaacta gctcaaagat ttgcattcca atataatcca tccctgcaac | 6660 |
| caagagctct tgttgtcttt gggtgtatta gcaaacgagt gtctcatggg cagataaagc | 6720 |
| agataatccg tattcttagc aaggcacttg agagttgctt aaaaggacct gacacttaca | 6780 |
| acagtcaagt tctgatagaa gctacagtaa tagcactaac caaattacag ccacttctta | 6840 |
| ataaggactc gcctctgcac aaagccctct tttgggtagc tgtggctgtg ctgcagcttg | 6900 |
| atgaggtcaa cttgtattca gcaggtaccg cacttcttga acaaacctg catactttag | 6960 |
| atagtctccg tatattcaat gacaagagtc cagaggaagt atttatggca atccggaatc | 7020 |
| ctctggagtg gcactgcaag caaatggatc attttgttgg actcaatttc aactctaact | 7080 |
| ttaactttgc attggttgga ccctttaa aagggtacag gcatcctca cctgctattg | 7140 |
| ttgcaagaac agtcagaatt ttacatacac tactaactct ggttaacaaa cacagaaatt | 7200 |
| gtgacaaatt tgaagtgaat acacagagcg tggcctactt agcagcttta cttacagtgt | 7260 |
| ctgaagaagt tcgaagtcgc tgcagcctaa aacatagaaa gtcacttctt cttactgata | 7320 |
| tttcaatgga aaatgttcct atggatacat atcccattca tcatggtgac ccttcctata | 7380 |
| ggacactaaa ggagactcag ccatggtcct ctcccaaagg ttctgaagga taccttgcag | 7440 |
| ccacctatcc aactgtcggc cagaccagtc cccgagccag gaaatccatg agcctggaca | 7500 |
| tggggcaacc ttctcaggcc aacactaaga agttgcttgg aacaaggaaa agttttgatc | 7560 |
| acttgatatc agacacaaag gctcctaaaa ggcaagaaat ggaatcaggg atcacaacac | 7620 |
| cccccaaaat gaggagagta gcagaaactg attatgaaat ggaaactcag aggatttcct | 7680 |
| catcacaaca gcacccacat ttacgtaaag tttcagtgtc tgaatcaaat gttctcttgg | 7740 |
| atgaagaagt acttactgat ccgaagatcc aggcgctgct tcttactgtt ctagctacac | 7800 |
| tggtaaaata taccacagat gagtttgatc aacgaattct ttatgaatac ttagcagagg | 7860 |
| ccagtgttgt gtttcccaaa gtcttttcctg ttgtgcataa tttgttggac tctaagatca | 7920 |
| acaccctgtt atcattgtgc caagatccaa atttgttaaa tccaatccat ggaattgtgc | 7980 |
| agagtgtggg gtaccatgaa gaatccccac cacaatacca aacatcttac ctgcaaagtt | 8040 |
| ttggttttaa tggcttgtgg cggtttgcag gaccgttttc aaagcaaaca caaattccag | 8100 |
| actatgctga gcttattgtt aagtttcttg atgccttgat tgcacgtac ctgcctggaa | 8160 |
| ttgatgaaga aaccagtgaa gaatccctcc tgactcccac atctccttac cctcctgcac | 8220 |
| tgcagagcca gcttagtatc actgccaacc ttaacctttc taattccatg acctcacttg | 8280 |
| caacttccca gcattcccca ggaatcgaca aggagaacgt tgaactctcc cctaccactg | 8340 |
| gccactgtaa cagtggacga actcgccacg gatccgcaag ccaagtgcag aagcaaagaa | 8400 |
| gcgctggcag tttcaaacgt aatagcatta agaagatcgt gtga | 8444 |

<210> SEQ ID NO 77
<211> LENGTH: 19
<212> TYPE: RNA
<213> ORGANISM: Artificial Sequence
<220> FEATURE:
<223> OTHER INFORMATION: Synthetic

<400> SEQUENCE: 77

| | |
|---|---|
| ggaaaagaau gugcagaaa | 19 |

<210> SEQ ID NO 78
<211> LENGTH: 19
<212> TYPE: RNA
<213> ORGANISM: Artificial Sequence
<220> FEATURE:
<223> OTHER INFORMATION: Synthetic

<400> SEQUENCE: 78
uuucugcaca uucuuuucc                                                    19

<210> SEQ ID NO 79
<211> LENGTH: 636
<212> TYPE: DNA
<213> ORGANISM: Artificial Sequence
<220> FEATURE:
<223> OTHER INFORMATION: Synthetic

<400> SEQUENCE: 79
atggcttcgg ggcaaggccc aggtcctccc aggcaggagt gcggagagcc tgccctgccc        60
tctgcttctg aggagcaggt agcccaggac acagaggagg ttttccgcag ctacgttttt      120
taccgccatc agcaggaaca ggaggctgaa ggggtggctg cccctgccga cccagagatg      180
gtcaccttac ctctgcaacc tagcagcacc atggggcagg tgggacggca gctcgccatc      240
atcggggacg acatcaaccg acgctatgac tcagagttcc agaccatgtt gcagcacctg      300
cagcccacgg cagagaatgc ctatgagtac ttcaccaaga ttgccaccag cctgtttgag      360
agtggcatca attggggccg tgtggtggct cttctgggct tcggctaccg tctggcccta      420
cacgtctacc agcatggcct gactggcttc ctaggccagg tgacccgctt cgtggtcgac      480
ttcatgctgc atcactgcat tgcccggtgg attgcacaga ggggtggctg ggtggcagcc      540
ctgaacttgg gcaatggtcc catcctgaac gtgctggtgg ttctgggtgt ggttctgttg      600
ggccagtttg tggtacgaag attcttcaaa tcatga                                636

<210> SEQ ID NO 80
<211> LENGTH: 21
<212> TYPE: DNA
<213> ORGANISM: Artificial Sequence
<220> FEATURE:
<223> OTHER INFORMATION: Synthetic

<400> SEQUENCE: 80
cctgtttgag agtggcatca a                                                 21

<210> SEQ ID NO 81
<211> LENGTH: 21
<212> TYPE: DNA
<213> ORGANISM: Artificial Sequence
<220> FEATURE:
<223> OTHER INFORMATION: Synthetic

<400> SEQUENCE: 81
ttgatgccac tctcaaacag g                                                 21

<210> SEQ ID NO 82
<211> LENGTH: 19
<212> TYPE: RNA
<213> ORGANISM: Artificial Sequence
<220> FEATURE:
<223> OTHER INFORMATION: Synthetic

<400> SEQUENCE: 82

```
ggucaccuua ccucugcaa                                               19
```

<210> SEQ ID NO 83
<211> LENGTH: 19
<212> TYPE: RNA
<213> ORGANISM: Artificial Sequence
<220> FEATURE:
<223> OTHER INFORMATION: Synthetic

<400> SEQUENCE: 83

```
uugcagaggu aaggugacc                                               19
```

<210> SEQ ID NO 84
<211> LENGTH: 20
<212> TYPE: DNA
<213> ORGANISM: Artificial Sequence
<220> FEATURE:
<223> OTHER INFORMATION: Synthetic

<400> SEQUENCE: 84

```
tctgcttctg gcaccatggg                                              20
```

<210> SEQ ID NO 85
<211> LENGTH: 501
<212> TYPE: DNA
<213> ORGANISM: Homo sapiens

<400> SEQUENCE: 85

```
atggcttcgg ggcaaggccc aggtcctccc aggcaggagt gcggagagcc tgccctgccc    60
tctgcttctg gcaccatggg gcaggtggga cggcagctcg ccatcatcgg ggacgacatc   120
aaccgacgct atgactcaga gttccagacc atgttgcagc acctgcagcc cacggcagag   180
aatgcctatg agtacttcac caagattgcc accagcctgt ttgagagtgg catcaattgg   240
ggccgtgtgg tggctcttct gggcttcggc taccgtctgg ccctacacgt ctaccagcat   300
ggcctgactg gcttcctagg ccaggtgacc cgcttcgtgg tcgacttcat gctgcatcac   360
tgcattgccc ggtggattgc acagaggggt ggctgggtgg cagccctgaa cttgggcaat   420
ggtcccatcc tgaacgtgct ggtggttctg ggtgtggttc tgttgggcca gtttgtggta   480
cgaagattct tcaaatcatg a                                            501
```

<210> SEQ ID NO 86
<211> LENGTH: 19
<212> TYPE: RNA
<213> ORGANISM: Artificial Sequence
<220> FEATURE:
<223> OTHER INFORMATION: Synthetic

<400> SEQUENCE: 86

```
cccucugcuu cuggcacca                                               19
```

<210> SEQ ID NO 87
<211> LENGTH: 19
<212> TYPE: RNA
<213> ORGANISM: Artificial Sequence
<220> FEATURE:
<223> OTHER INFORMATION: Synthetic

<400> SEQUENCE: 87

```
uggugccaga agcagaggg                                               19
```

ALTERNATIVE SPLICING VARIANTS OF GENES ASSOCIATED WITH PROSTATE CANCER RISK AND SURVIVAL

REFERENCE TO RELATED APPLICATION

This application is a National Phase of International Application No. PCT/US2012/056346, filed Sep. 20, 2012, which claims priority to U.S. Provisional Patent Application No. 61/536,957, filed Sep. 20, 2011, which is incorporated herein by reference.

GOVERNMENT RIGHTS

This invention was made with government support under R01-CA120316, R01-DK056108, and 5U01-CA-116937 awarded by the NIH. The U.S. Government has certain rights in the invention.

FIELD OF THE INVENTION

The present invention relates to novel splicing variants of a number of genes associated with prostate cancer risk and survival, and also the risk assessment, detection, diagnosis, or prognosis of prostate cancer (CaP). More specifically, this invention relates to the detection of certain splicing variants in genes PIK3CD, FGFR3, TSC2, ITGA4, MET, NF1, BAK1, and RASGRP2 to determine the risk, detect, diagnose, or prognosticate prostate cancer, particularly in the African American population. Research for the present invention was supported in part by American Cancer Society grant ACS-IRG-08-091-01.

BACKGROUND OF THE INVENTION

Prostate cancer (PCa) is the most common form of cancer among males. Overwhelming clinical evidence shows that human prostate cancer has the propensity to metastasize to bone, and the disease appears to progress inevitably from androgen dependent to androgen refractory status, leading to increased patient mortality. This prevalent disease is currently the second leading cause of cancer death among men in the U.S.

There are striking population (race) disparities in prostate cancer risk and survival outcome borne out of current health statistics data. This is particularly evident between African Americans (AA) and their Caucasian American (CA) counterparts. Epidemiologic studies have shown that higher mortality and recurrence rates of prostate cancer are still seen in AA men even after adjustment for socioeconomic status, environmental factors and health care access. Thus, it is likely that intrinsic biological differences account for some of the cancer disparities. Identifying these differences has been identified as a high-priority research area by the NIH, NCI and the Center to Reduce Cancer Health Disparities (CRCHD).

There are currently very few diagnostics methods available for the diagnosis and prevention of prostate cancer, particularly which can be used as predictor of risk and survival in African American population. Thus, the identification of genetic differences between AA and their CA counterparts, that are responsible for predisposition of prostate cancer would provide for a better understanding of the mechanisms of cancer causation (including ethnic and individual susceptibility), and ultimately lead to ways of prostate cancer prevention.

SUMMARY OF THE INVENTION

Prostate cancer (PCa) is a disease conferred by multiple gene mutations, numerous alternations in gene expression and aberrant changes in genome composition/architecture. The African American (AA) population exhibits higher incidence and mortality rates compared to Caucasian Americans (CA). The present invention, through systematic mRNA expression profiling, characterizes the global mRNA expression profiles in AA and CA prostate tissue samples. A large number of genes are shown to have differential expression between AA and CA patients. Notably, several genes residing within the 5 oncogenic signaling pathways have been identified as exhibiting differential splicing, which includes but not limited to PIK3CD, FGFR3, TSC2, FGFR2, PDGFRA, ITGA4, MET, EPHA3, NF1, RASGRP2, CTNNB1, TSC2, ATM, CDK4, and RB 1 between AA and CA PCa specimens. Quantitative analysis of the expression profiles of PIK3CD, FGFR3, TSC2, RASGRP2, ITGA4, MET, NF1 and BAK1 in prostate samples confirm differential splicing between the AA and CA patients. With certain splicing variants predominantly exist in AA patients. As a non-limiting example, PIK3CD is expressed predominantly as a long variant in CA patients, whereas the AA patient would have higher portion of a short variant. The alternatively spliced short variant of PIK3CD is found to be a more aggressive form. Increasing the short to long variants ratio in a PCa cell line (MDA PCa 2b) that is representative to the AA PCa PIK3CD expression profile, by knocking down PIK3CD long variant expression increases cell proliferation and cell migration. Selectively knocking down the expression of PIK3CD short variant in the same cell line, decreases the short to long variants ratio, and results in marked decrease of cell proliferation and cell migration. Similarly AA predominant variants of FGFR3, TSC2 and RASGRP2 are also shown to be the more aggressive variant.

It is thus discovered by the inventors that alternative splicing variants for genes in the oncogenic signaling pathways, such as PIK3CD, FGFR3, TSC2, FGFR2, PDGFRA, ITGA4, MET, EPHA3, NF1, RASGRP2, CTNNB1, TSC2, ATM, CDK4, and RB1 are strong predictors of prostate cancer risk and survival, particularly in the AA patient population. It is thus an aim of the present invention to predict the risk and survival of a patient, by detecting the presence or absence of AA predominant variants of the genes in the oncogenic signaling pathways, particularly for PIK3CD, FGFR3, TSC2, FGFR2, PDGFRA, ITGA4, MET, EPHA3, NF1, RASGRP2, CTNNB1, TSC2, ATM, CDK4, and RB1, and more particularly for PIK3CD, FGFR3, TSC2, RASGRP2, ITGA4, MET, NF1 and BAK1. It is also an aspect of the present invention to utilize relative proportions of splicing variants of a certain gene as a predictor for PCa risk and survival in a patient.

Another aspect of the present invention is directed to isolated polynucleotide sequences of novel splicing variants of PIK3CD, FGFR3, TSC2, RASGRP2, ITGA4, MET, NF1 and BAK1. These novel splicing variants are particularly useful for the detection of the presence or absence of splicing variants in these genes that are in oncogenic signaling pathways. Detection of the presence or absence of splicing variants may be by polymerase chain reaction, by oligonucleotide probes hybridization, particularly high throughput DNA micro array analysis, or high throughput DNA sequencing, or any other means known to one skilled in the art. The isolated novel splicing variants sequences are also useful for targeted silencing of certain splicing variants of these genes. Targeted gene silencing may be by siRNA, miRNA, or other complementary RNA constructs.

Additionally, polypeptide products of the novel splicing variants of the present invention may be analyzed for determining the presence or absence of certain splicing variants. Mass spectrometry may be used to identify peptide fragments specific to certain splicing variants. Antibodies specifically recognize specific amino acid sequences of the novel splicing variants may be developed for the detection of the protein products of these splicing variants. The antibodies may be monoclonal antibodies, polyclonal antibodies, Fab, single chain antibody, or other engineered antibody constructs known to one skilled in the art.

DETAILED DESCRIPTION OF THE PREFERRED EMBODIMENT

Alternative splicing dramatically expands the protein coding repertoire of higher eukaryotes. Current estimates suggest that greater than 60% of all human genes have more than one isoform/splice variant. The expression of specific splice variants is regulated in a developmentally and tissue-specific manner (Black DL: Mechanisms of alternative pre-messenger RNA splicing. Annu Rev Biochem 2003, 72:291-336). Alternatively spliced isoforms from the same gene can produce proteins with drastically different properties. For example, the bcl-x gene utilizes different 5' splice sites, resulting in proteins that have antagonistic functions. The short form of bcl-x promotes apoptosis, while the long form inhibits cell death (Boise L H, Gonzalez-Garcia M, Postema C E, Ding L, Lindsten T, Turka L A, Mao X, Nunez G, Thompson CB: bcl-x, a bcl-2-related gene that functions as a dominant regulator of apoptotic cell death. Cell 1993, 74:597-608).

Characterization of Clinical Specimens

Figure 1:
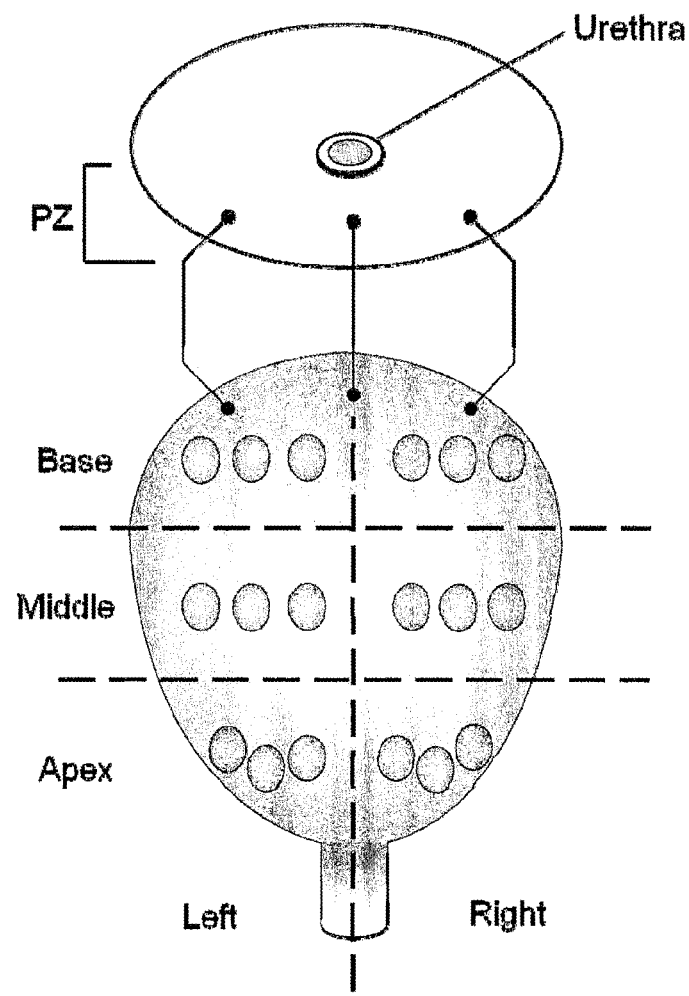
FIG. 1 is a schematic drawing for prostate biopsy core sampling.

Needle biopsy cores were collected by GWU Medical Faculty Associates urologists from right-base, left-base, right-mid, left-mid, right-apex, left-apex, right-transition, and left-transition zones of the prostate gland of individual patients presenting with high serum levels (>7 ng/ml) of prostate specific antigen (PSA). A schematic for 18 core biopsy is shown in FIG. 1. Collected cores were immediately examined by a board certified PCa pathologist. PCa cores were determined to have a pathologic tumor stage of 2, and Gleason scores ranging from 6-9. There was no significant difference between the two racial groups (AA versus CA) with respect to age and tumor grade. Paired normal biopsy cores were also available from the same patients for genomic analysis (normal cores typically 1-2 cm away from cancer cores and deemed cancer free by pathologists). Each core contains sufficient RNA material for Affymetrix Human Exon 1.0 ST GeneChip profiling (i.e. 1 µg total RNA).

Exon Expression Profiling of AA and CA PCa and Normal Specimens

Total RNA was isolated from PCa and paired normal prostate cores. Exon profiling was performed on the Affymetrix Human Exon 1.0 ST GeneChip. The GeneChip represents an optimal platform for both expression profiling and splice variant detection (Kwan T, Benovoy D, Dias C, Gurd S, Provencher C, Beaulieu P, Hudson T J, Sladek R, Majewski J: Genome-wide analysis of transcript isoform variation in humans. Nat Genet 2008, 40:225-231; Network TCGAR: Comprehensive genomic characterization defines human glioblastoma genes and core pathways. Nature 2008, 455: 1061-1068), as exon level annotations are derived from empirically determined, highly curated mRNA sequences and ab-initio computational predictions (see www.affymetrix.com/support/technical/whitepapers.affx). The GeneChip contains approximately 5.4 million 5-1 µm features (probes) grouped into 1.4 million probe sets interrogating over one million exon clusters. A 4-way statistical design (t-test with 10% false discovery rate (FDR) for multiple test correction) was employed to identify differentially expressed exons (corresponding to differentially expressed splice variants) in the following comparisons: AA normal vs. CA normal, AA cancer vs. CA cancer, AA cancer vs. AA normal, and CA cancer vs. CA normal. See FIG. 1A for comparison of AA cancer vs. CA cancer at the exon level.

Figure 2:
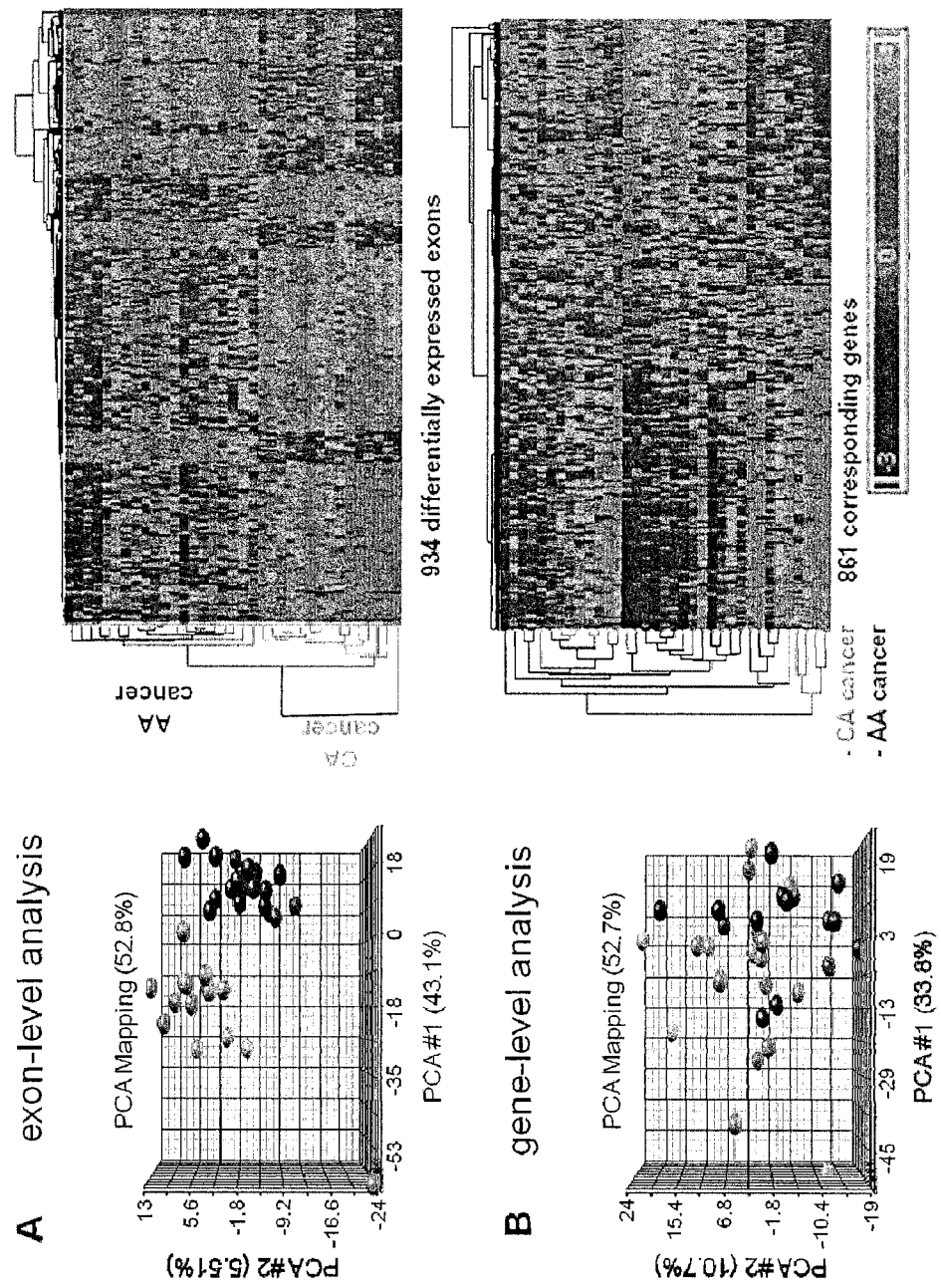
FIG. 2 shows differentially expressed exons between AA and CA populations.

The inventor through exon level analysis has identified 861 genes (e.g. PIK3CD, FGFR3, TSC2, RASGRP2, ITGA4, MET, NF1 and BAK1) exhibiting differential splicing patterns between the AA and CA populations. Differentially expressed exons between AA and CA populations are shown in FIG. 2. FIG. 2(A) shows Principle Components Analysis (PCA) plots and clustering analysis of differentially expressed exons between AA and CA PCa specimens. 20 AA and 15 CA PCa specimens were analyzed for global alternative splicing patterns (i.e. differentially expressed exons) using the Affymetrix human Exon 1.0 ST arrays. These splice variants represent candidate markers mediating PCa disparities. An example of a gene exhibiting population-specific splicing is integrin α4 (ITGA4) which has been postulated to be a metastasis suppressor, since blocking its activity with antisense RNA enhances oral squamous carcinoma cell motility (Zhang Y, Lu H, Dazin P, Kapila Y: Functional differences between integrin alpha4 and integrins alpha5/alphaV in modulating the motility of human oral squamous carcinoma cells in response to the V region and heparin-binding domain of fibronectin. Exp Cell Res 2004, 295:48-58.).

Figure 3:
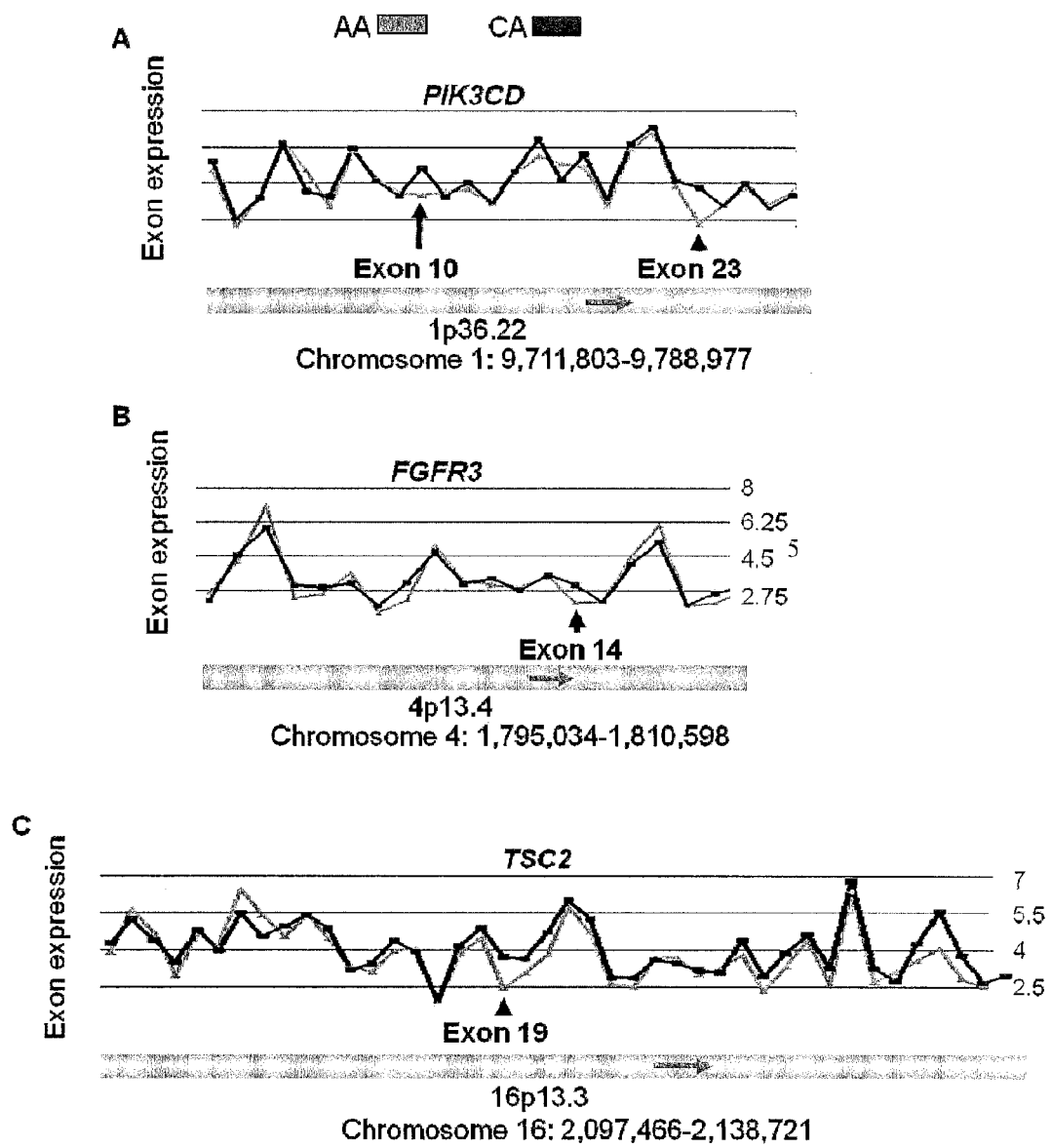
FIG. 3 shows differential splicing events in AA and CA PCa specimens.

FIG. 3 shows relative expression of individual exons of PIK3CD, FGFR3, and TSC2 in AA and CA prostate cancers. FIG. 3(a) shows PIK3CD (phosphoinositide-3-kinase, catalytic, delta polypeptide) variants expression, FIG. 3(b) shows FGFR3 (fibroblast growth factor receptor 3) variants expression, and FIG. 3(c) shows TSC2 (tuberous sclerosis 2). Arrows indicate exons that are missing in the AA variant but present in the CA variant for each gene. Specifically, PIK3CD variants that lack exons 10 and 23, FGFR3 variant lack exon 14, and TSC2 variant lacks exon 19 are more prevalent in AA PCa patients.

Figure 4:
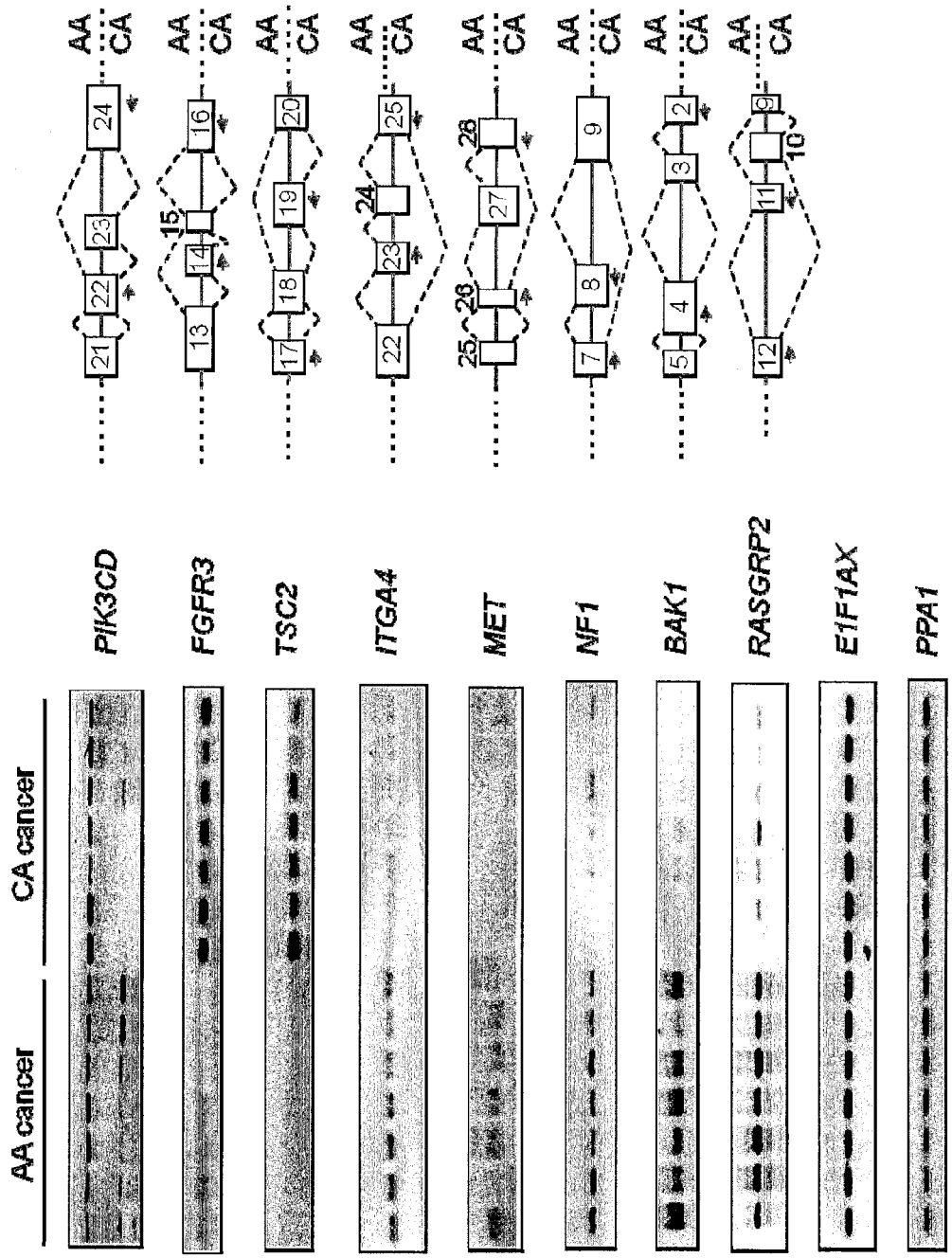
FIG. 4 shows quantitative RT-PCR validation of differentially expressed exons in AA and CA specimens.

FIG. 4 shows quantitative RT-PCR validation of differentially expressed exons in AA and CA specimens. AA and CA patient samples are analyzed using quantitative RT-PCR, using primers listed in Table 1. Preferential expression of a particular exon in either AA or CA PCa specimens for the PIK3CD, FGFR3, TSC2, ITGA4, MET, NF1, BAK1, and RASGRP2 genes is seen. E1F1AX and PPA1 served as internal RT-PCR control genes, which are expressed equally in AA and CA PCa specimens.

TABLE 1

Primers for qRT-PCR validations of splice variants (-L and -S forms)

| | |
|---|---|
| PIK3CD | Primer-f (SEQ ID No. 2): CAAACTGAAGGCCCTGAATGA<br>Primer-r (SEQ ID No. 3): TCTCGGATCATGATGTTGTCG |
| FGFR3 | Primer-f (SEQ ID No. 20): ACAACGTGATGAAGATCGCA<br>Primer-r (SEQ ID No. 21): AGGTCGTGTGTGCAGTTGG |
| TSC2 | Primer-f (SEQ ID No. 29): TTTGACTTCCTGTTGCTGCT<br>Primer-r (SEQ ID No. 30): TGAGCACTTTATAGCGCAG |
| RASGRP2 | Primer-f (SEQ ID No. 38): TCACGGTGTCTCTGGATCAGT<br>Primer-r (SEQ ID No. 39): CCACCATCTTCTCGATGTGCT |
| ITGA4 | Primer-f (SEQ ID No. 53): TCTTGCTGTTGGGAGTATGAA<br>Primer-r (SEQ ID No. 54): TGATACTGAGGTCCTCTTCCG |
| MET | Primer-f (SEQ ID No. 66): TGGTGGAAAGAACCTCTCAA<br>Primer-r (SEQ ID No. 67): ATCTTGGCTCACTGCAACCT |
| NF1 | Primer-f (SEQ ID No. 71): GCATTTTGGAACTGGGTAGAA<br>Primer-r (SEQ ID No. 72): AACCACCATGGACTGAACAA |
| BAK1 | Primer-f (SEQ ID No. 80): CCTGTTTGAGAGTGGCATCAA<br>Primer-r (SEQ ID No. 81): TTGATGCCACTCTCAAACAGG |

Figure 5:
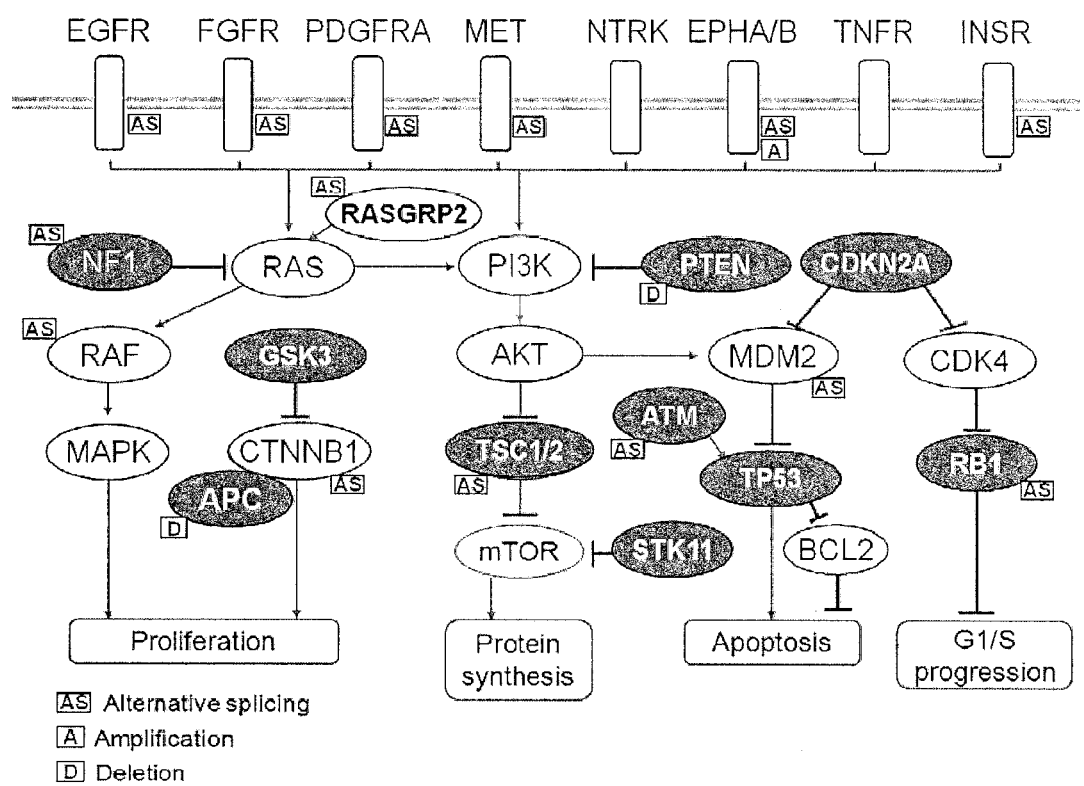
FIG. 5 illustrates alternative splicing events were found in various signaling molecules in the cell survival and proliferation pathways.

Recently, genome sequencing efforts as part of the Cancer Genome Atlas Project has demonstrated that a number of genes (e.g. RAS, PTEN, p53, PI3K, APC, etc.) exhibiting frequent mutational hits in cancers can be found primarily residing in 3-5 major signaling pathways (Network TCGAR: Comprehensive genomic characterization defines human glioblastoma genes and core pathways. Nature 2008, 455: 1061-1068; Parsons D W, Jones S, Zhang X, Lin J C, Leary R J, Angenendt P, Mankoo P, Carter H, Siu IM, Gallia G L, et al: An integrated genomic analysis of human glioblastoma multiforme. Science 2008, 321:1807-1812; Ding L, Getz G, Wheeler D A, Mardis E R, McLellan M D, Cibulskis K, Sougnez C, Greulich H, Muzny D M, Morgan M B, et al: Somatic mutations affect key pathways in lung adenocarcinoma. Nature 2008, 455:1069-1075). Of interest from a cancer disparities perspective is our observation that many of these same genes are prone to population-specific splicing patterns. FIG. 5 indicates genes marked with (AS) define differential alternative splicing events occurring in AA versus CA PCa. (Copy number amplifications (A) and deletions (D) are also indicated). At least 11 out of 26 genes residing in the 5 oncogenic signaling pathways have been identified by the inventors as exhibiting differential splicing between AA and CA PCa specimens. These genes include FGFR2, PDGFRA, MET, EPHA3, NF1, RASGRP2, CTNNB 1, TSC2, ATM, CDK4, and RB 1. The inventors further show that differential mRNA splicing in racial populations plays an important role in cancer health disparities.

Figure 6:
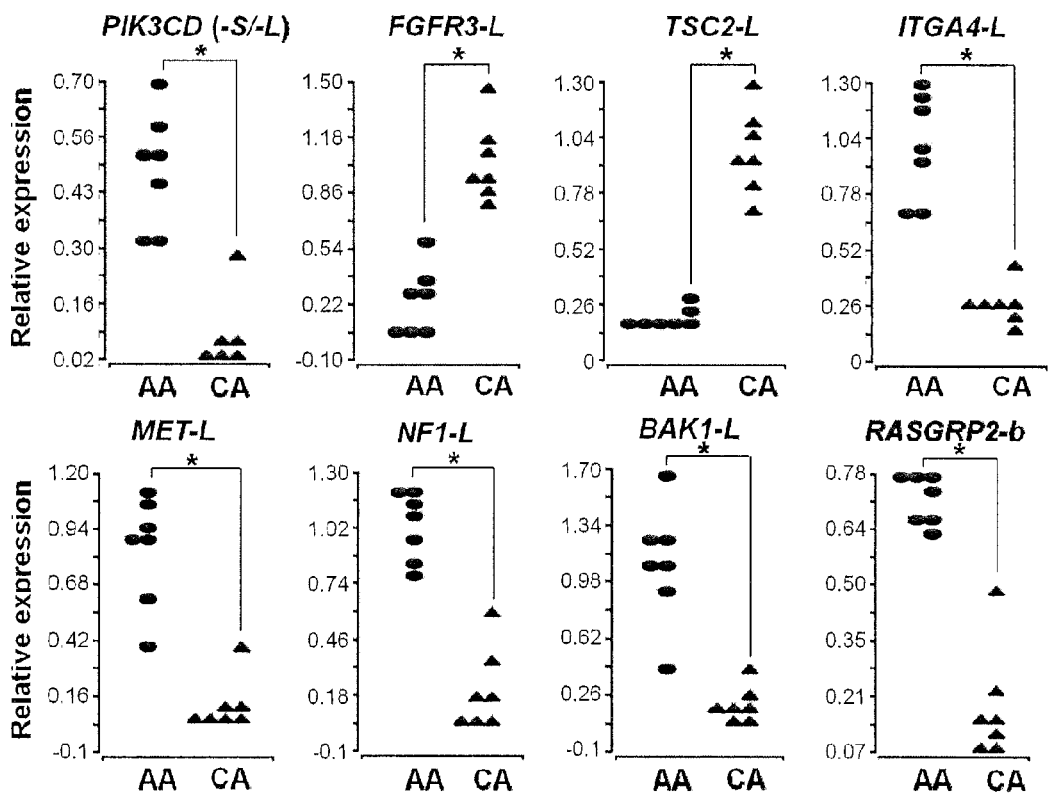
FIG. 6 shows relative expression levels of PIK3CD, FGFR3, TSC2, ITGA4, MET, NF1, BAK1, and RASGRP2 splicing variants.

FIG. 6 shows quantification of differential splicing in PIK3CD, FGFR3, TSC2, ITGA4, MET, NF1, BAK1, and RASGRP2 in AA and CA PCa patients. For each of these genes, one variant is predominant in AA patients. Also, proportions of variants, such as short and long form of PIK3CD are markedly different between AA and CA patients. AA patients have a higher S/L ration than CA patients.

Figure 7:
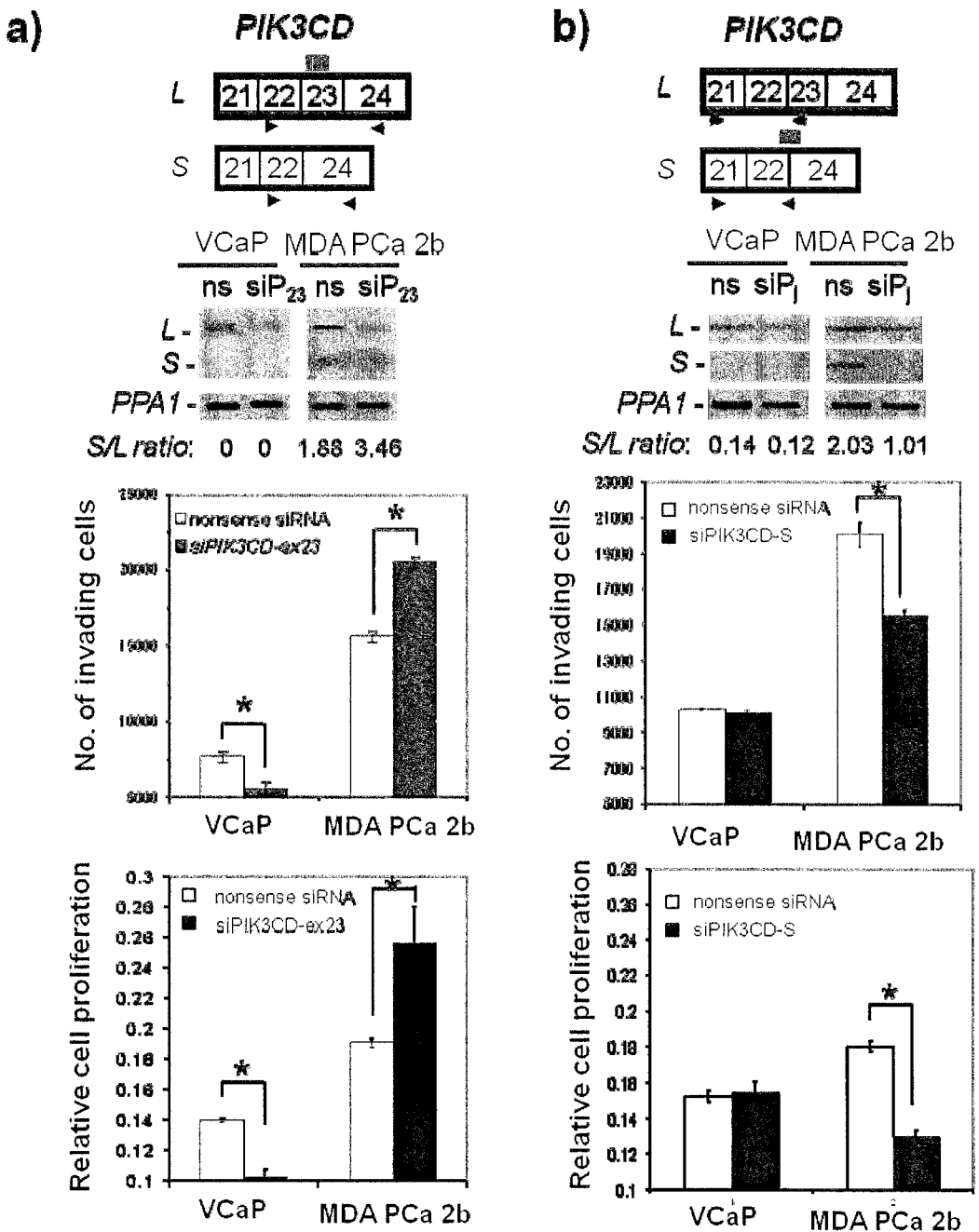
FIG. 7 shows the effect of PIK3CD splicing variants on cell proliferation and invasion.

Functional Consequences of Splice Variants in PCa Cell Lines Derived from AA and CA Patients Inventors demonstrate that the splice variant (short form or S variant) for phosphoinositide-3 kinase delta (PIK3CD) found in AA PCa specimens encodes a more aggressive version of the gene (i.e. leading to greater proliferation and invasion of cancer cells) compared to the variant counterpart (long form or L variant) found in CA PCa specimens (FIG. 7). In the CA PCa cell line VCaP, the L form is the only variant found, while very little to no expression of the S variant is seen (and hence the reason we refer to the L variant as the 'CA isoform') (FIG. 7A). The predominant expression of the L variant and very little to no expression of the S variant in the CA PCa cell line is consistent with the CA patient samples (see PIK3CD in FIG. 4). SiRNA-mediated knockdown of the L variant in VCaP cells leads to a decrease in Matrigel invasion and a decrease in proliferation (FIG. 7A). By comparison, the AA PCa cell line MDA PCa 2b expresses both an L and S variant, and knockdown of the L variant leads to an increase in Matrigel invasion and an increase in proliferation (FIG. 7A). Since VCaP cells express very little to no S variant, targeted siRNA-mediated knockdown of this variant leads to no change in Matrigel invasion and proliferation (FIG. 7B). In contrast, targeted knockdown of the S variant in MDA PCa 2b cells leads to decreased Matrigel invasion and decreased proliferation (since the S variant is found almost exclusively in AA patient samples, it is referred to as the 'AA variant') (FIG. 7B). These data indicate that the balance of S to L isoforms in MDA PCa 2b cells dictates the oncogenic profile of the AA PCa cell line. Namely, knocking down the L variant in MDA PCa 2b cells increases the S/L ratio, leading to a higher proportion of the aggressive S variant and consequently increased invasiveness and proliferation of the cell line. In contrast, knocking down the S variant in MDA PCa 2b cells decreases the S/L ratio, leading to a higher proportion of the less aggressive L variant and consequently decreased invasiveness and proliferation of the cell line. Analogous findings were obtained in MDA PCa 2b cells when the ratio of the 'AA variant' (S or b isoform) was increased over the 'CA variant' (L or an isoform) for the FGFR3, TSC2.

Figure 8:
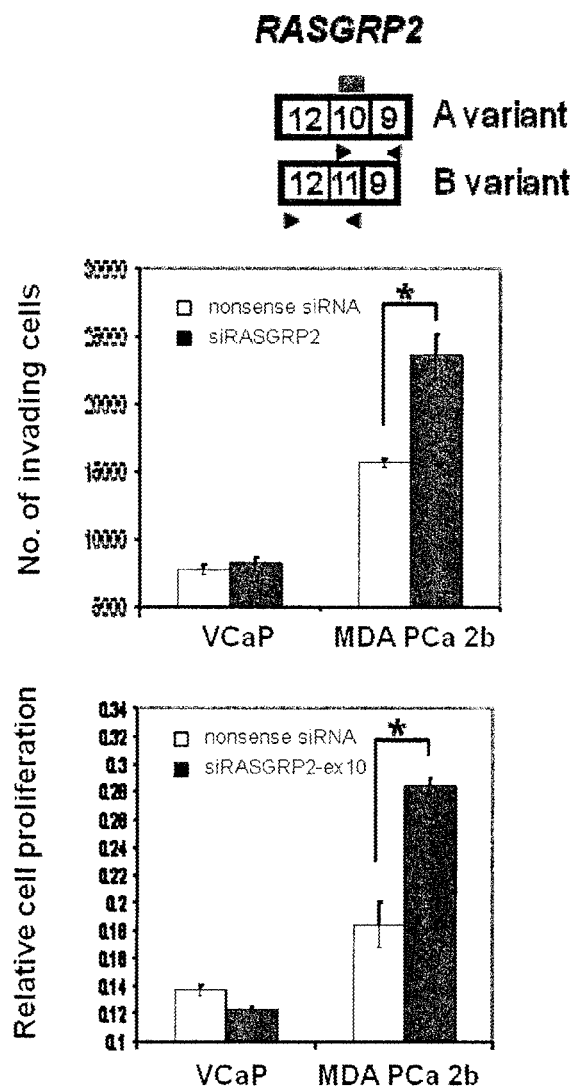
FIG. 8 shows effect of knockdown RASGRP2 splicing variants on cell proliferation and invasion.

For RASGRP2, the long variant (with exon 10) is common to both AA and CA patients, whereas the short variant (without exon 10) is unique to AA. Targeted knockdown of the long splicing variant in VCaP cells reduced Matrigel invasion and an increase in proliferation (FIG. 8). In contrast, target knockdown of the RASGRP2 long variant in MDA PCa 2b Cells has the opposite effect.

Figure 9:
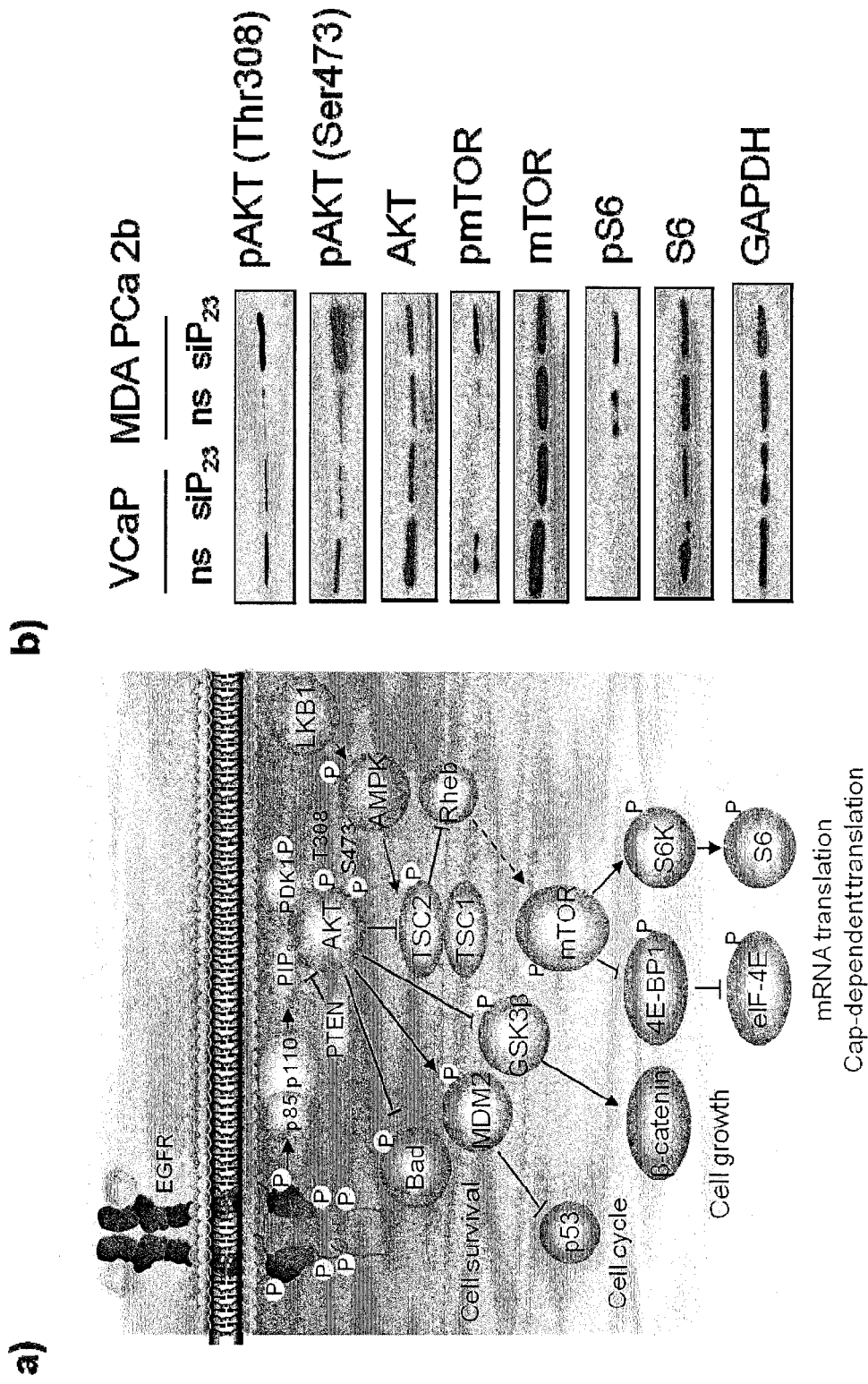
FIG. 9 shows effect of knockdown PIK3CD "long" variant on the AKT pathway.

Activation of AKT is known to promote cell growth and mRNA translation (FIG. 9a). When the expression of PIK3CD "long" variant is knocked down by siRNA targeting of Exon 23 in the VCaP cell line, which only expresses the long variant, there is a decrease of phosphorylation of AKT, compared to nonsense siRNA control, and also decrease of phosphorylation of downstream signaling proteins mTOR and S6 (FIG. 9b). However, in MDA PCa 2b cells, which express the short variant of PIK3CD, knocking down the long variant of PIK3CD markedly increases AKT phosphorylation, both on Thr308 and Ser473, and increases phosphorylation of mTOR and S6 (FIG. 9b). In other words, increasing S/L variants proportion in MDA PCa 2b cells activates the AKT pathways.

Figure 10:
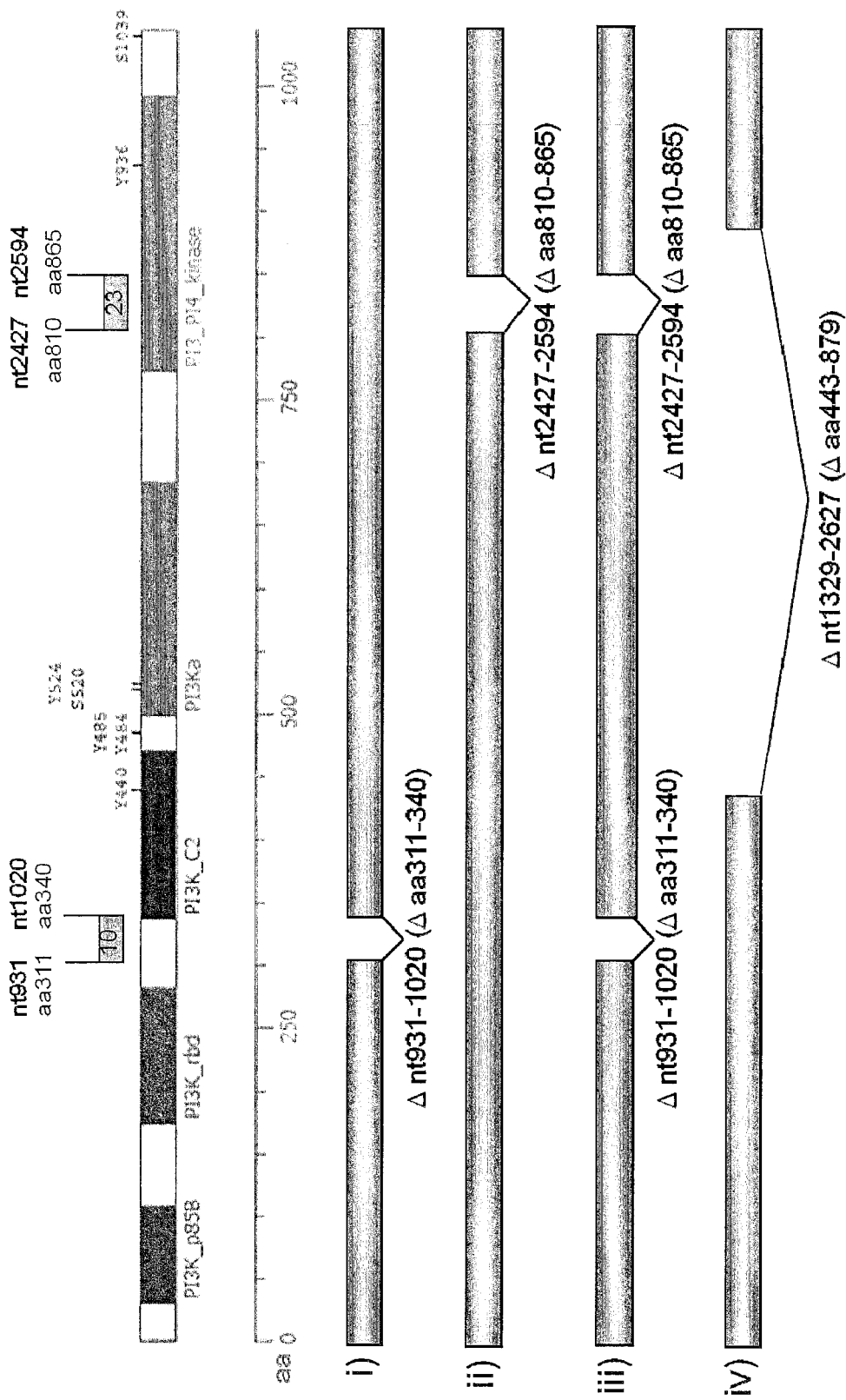
FIG. 10 shows 4 novel PIK3CD variants.

The inventor discovered four novel PIK3CD variants (FIG. 10), where variant 1 lacks exon 10 (SEQ ID No. 7), which can be shown as the deletion of nt2430-2592 compared to full length PIK3CD cDNA sequence (SEQ ID. No. 1), variant 2 lacks exon 23 (SEQ ID No. 11, deletion of nt931-1020), variant 3 lacks both exon 10 and 23 (SEQ ID No. 14, deletion of nt931-1020 and nt2430-2592), and variant 4 contains a deletion from nt1329-2627 (SEQ ID No. 16). The nucleotide sequence of PIK3CD full length cDNA sequence is shown in Table 2. Exon 10 and exon 23 are marked with double underline and wave underline, respectively. cDNA sequence of variants 1-4 (SEQ ID Nos. 7, 11, 14, and 16) are shown in Tables 3-6. Exemplary primers across the junctions of the splicing variants (SEQ ID Nos. 6, 10, and 15) that are useful for detecting the presence of these variants are shown in Table 7. Exemplary siRNAs for selective knockdown of PIK3CD full length (targeting exon 23, SEQ ID Nos. 4 and 5)) and variants (targeting exon junctions (SEQ ID Nos. 8, 9, 12, and 13) and deletion junction (SEQ ID Nos. 17 and 18)) are listed in Table 8.

The inventor also discovered a novel splicing variant of FGFR3 (fibroblast growth factor receptor 3), which lacks exon 14 (SEQ ID No. 19, Table 10). The nucleotide sequence of FGFR3 full length cDNA sequence (SEQ ID No. 19) is shown in Table 9. Exon 14 is marked with double underline. Exemplary primer across the junction of splicing variant (SEQ ID No. 26) that is useful for detecting the presence of this variant is shown in Table 11. Exemplary siRNAs for selective knockdown of FGFR3 full length (targeting exon 14, SEQ ID NOs. 22 and 23)) and variant (targeting exon junction (SEQ ID Nos. 26 and 27) are listed in Table 12.

The inventor also discovered a novel splicing variant of TSC2 (tuberous sclerosis 2), which lacks exon 19 (SEQ ID No. 34, Table 14). The nucleotide sequence of TSC2 full length cDNA sequence (SEQ ID No. 28) is shown in Table 12. Exon 19 is marked with double underline. Exemplary primer across the junction of splicing variant (SEQ ID No. 33) that is useful for detecting the presence of this variant is shown in Table 15. Exemplary siRNAs for selective knockdown of TSC2 full length (targeting exon 19, SEQ ID NOs. 31 and 32)) and variant (targeting exon junction (SEQ ID Nos. 35 and 36) are listed in Table 16.

The inventor also discovered two novel splicing variants of RASGRP2 (RAS guanyl-releasing protein 2), which lacks exon 10 (SEQ ID No. 45, Table 18) or exon 11 (SEQ ID No. 49, Table 19). The nucleotide sequence of RASGRP2 full length cDNA sequence (SEQ ID No. 37) is shown in Table 17. Exon 10 is marked with double underline, and exon 11 is marked with wave underline. Exemplary primers across the junctions of the splicing variants (SEQ ID Nos. 44 and 48) that are useful for detecting the presence of these variants are shown in Table 20. Exemplary siRNAs for selective knockdown RASGRP2 full length (targeting exon 10, SEQ ID NOs. 40 and 41, targeting exon 11, SEQ ID NOs. 42 and 43)) and variants (targeting exon junctions (SEQ ID Nos. 46, 47, 50, and 51)) are listed in Table 21.

The inventor also discovered a novel splicing variant of ITGA4 (integrin α4), which lacks exon 23 (SEQ ID No. 58, Table 23). The nucleotide sequence of ITGA4 full length cDNA sequence (SEQ ID No. 52) is shown in Table 22. Exon 23 is marked with double underline. Exemplary primer across the junction of splicing variant (SEQ ID No. 57) that is useful for detecting the presence of this variant is shown in Table 24. Exemplary siRNAs for selective knockdown of ITGA4 full length (targeting exon 23, SEQ ID NOs. 55 and 56)) and variant (targeting exon junction (SEQ ID Nos. 59 and 60)) are listed in Table 25.

The inventor also discovered a novel splicing variant of MET (MNNG HOS Transforming gene), which include the insertion of non-coding exon 27 (SEQ ID No. 65, Table 27). The nucleotide sequence of MET full length cDNA sequence (SEQ ID No. 62) is shown in Table 26. Exon 27 is marked with double underline. Exemplary primer across junctions of full length variant (SEQ ID No. 61) is shown in Table 28. Exemplary siRNAs for selective knockdown of MET full length (targeting exon junction 26 and 28 (SEQ ID Nos. 63 and 64) and variant (targeting exon 27 (SEQ ID Nos. 68 and 69)) are listed in Table 29.

The inventor also discovered a novel splicing variant of NF1 (Neurofibromin 1), which lacks exon 8 (SEQ ID No. 76, Table 31). The nucleotide sequence of NF1 full length cDNA sequence (SEQ ID No. 70) is shown in Table 30. Exon 8 is marked with double underline. Exemplary primer across the junction of splicing variant (SEQ ID No. 75) that is useful for detecting the presence of this variant is shown in Table 32. Exemplary siRNAs for selective knockdown of NF1 full length (targeting exon 8, SEQ ID NOs. 73 and 74) and variant (targeting exon junction (SEQ ID Nos. 77 and 78)) are listed in Table 33.

The inventor also discovered a novel splicing variant of BAK1 (Bcl-2 homologous antagonist/killer), which lacks exon 2 (SEQ ID No. 85, Table 35). The nucleotide sequence of BAK1 full length cDNA sequence (SEQ ID No. 79) is shown in Table 34. Exon 2 is marked with double underline. Exemplary primer across the junction of splicing variant (SEQ ID No. 84) that is useful for detecting the presence of this variant is shown in Table 36. Exemplary siRNAs for selective knockdown of BAK1 full length (targeting exon 2, SEQ ID NOs. 82 and 83) and variant (targeting exon junction (SEQ ID Nos. 86 and 87) are listed in Table 37.

TABLE 2

PIK3CD (Full length) Nucleotide Sequence (3135 nt, SEQ ID No. 1)

ATGCCCCCTGGGGTGGACTGCCCCATGGAATTCTGGACCAAGGAGGAGAATCAGAGCGTTGTGGTTGACT

TCCTGCTGCCCACAGGGGTCTACCTGAACTTCCCTGTGTCCCGCAATGCCAACCTCAGCACCATCAAGCA

TABLE 2 -continued

PIK3CD (Full length)Nucleotide Sequence (3135 nt, SEQ ID No. 1)

```
GCTGCTGTGGCACCGCGCCCAGTATGAGCCGCTCTTCCACATGCTCAGTGGCCCCGAGGCCTATGTGTTC
ACCTGCATCAACCAGACAGCGGAGCAGCAAGAGCTGGAGGACGAGCAACGGCGTCTGTGTGACGTGCAGC
CCTTCCTGCCCGTCCTGCGCCTGGTGGCCCGTGAGGGCGACCGCGTGAAGAAGCTCATCAACTCACAGAT
CAGCCTCCTCATCGGCAAAGGCCTCCACGAGTTTGACTCCTTGTGCGACCCAGAAGTGAACGACTTTCGC
GCCAAGATGTGCCAATTCTGCGAGGAGGCGGCCGCCCGCCGGCAGCAGCTGGGCTGGGAGGCCTGGCTGC
AGTACAGTTTCCCCCTGCAGCTGGAGCCCTCGGCTCAAACCTGGGGGCCTGGTACCCTGCGGCTCCCGAA
CCGGGCCCTTCTGGTCAACGTTAAGTTTGAGGGCAGCGAGGAGAGCTTCACCTTCCAGGTGTCCACCAAG
GACGTGCCGCTGGCGCTGATGGCCTGTGCCCTGCGGAAGAAGGCCACAGTGTTCCGGCAGCCGCTGGTGG
AGCAGCCGGAAGACTACACGCTGCAGGTGAACGGCAGGCATGAGTACCTGTATGGCAGCTACCCGCTCTG
CCAGTTCCAGTACATCTGCAGCTGCCTGCACAGTGGGTTGACCCCTCACCTGACCATGGTCCATTCCTCC
TCCATCCTCGCCATGCGGGATGAGCAGAGCAACCCTGCCCCCAGGTCCAGAAACCGCGTGCCAAACCAC
CTCCCATTCCTGCGAAGAAGCCTTCCTCTGTGTCCCTGTGGTCCCTGGAGCAGCCGTTCCGCATCGAGCT
CATCCAGGGCAGCAAAGTGAACGCCGACGAGCGGATGAAGCTGGTGGTGCAGGCCGGGCTTTTCCACGGC
AACGAGATGCTGTGCAAGACGGTGTCCAGCTCGGAGGTGAGCGTGTGCTCGGAGCCCGTGTGGAAGCAGC
GGCTGGAGTTCGACATCAACATCTGCGACCTGCCCCGCATGGCCCGTCTCTGCTTTGCGCTGTACGCCGT
GATCGAGAAAGCCAAGAAGGCTCGCTCCACCAAGAAGAAGTCCAAGAAGGCGGACTGCCCCATTGCCTGG
GCCAACCTCATGCTGTTTGACTACAAGGACCAGCTTAAGACCGGGGAACGCTGCCTCTACATGTGGCCCT
CCGTCCCAGATGAGAAGGGCGAGCTGCTGAACCCCACGGGCACTGTGCGCAGTAACCCCAACACGGATAG
CGCCGCTGCCCTGCTCATCTGCCTGCCCGAGGTGGCCCCGCACCCCGTGTACTACCCCGCCCTGGAGAAG
ATCTTGGAGCTGGGGCGACACAGCGAGTGTGTGCATGTCACCGAGGAGGAGCAGCTGCAGCTGCGGGAAA
TCCTGGAGCGGCGGGGTCTGGGGAGCTGTATGAGCACGAGAAGGACCTGGTGTGGAAGCTGCGGCATGA
AGTCCAGGAGCACTTCCCGGAGGCGCTAGCCCGGCTGCTGCTGGTCACCAAGTGGAACAAGCATGAGGAT
GTGGCCCAGATGCTCTACCTGCTGTGCTCCTGGCCGGAGCTGCCCGTCCTGAGCGCCCTGGAGCTGCTAG
ACTTCAGCTTCCCCGATTGCCACGTAGGCTCCTTCGCCATCAAGTCGCTGCGGAAACTGACGGACGATGA
GCTGTTCCAGTACCTGCTGCAGCTGGTGCAGGTGCTCAAGTACGAGTCCTACCTGGACTGCGAGCTGACC
AAATTCCTGCTGGACCGGGCCCTGGCCAACCGCAAGATCGGCCACTTCCTTTTCTGGCACCTCCGCTCCG
AGATGCACGTGCCGTCGGTGGCCCTGCGCTTCGGCCTCATCCTGGAGGCCTACTGCAGGGGCAGCACCCA
CCACATGAAGGTGCTGATGAAGCAGGGGGAAGCACTGAGCAAACTGAAGGCCCTGAATGACTTCGTCAAG
CTGAGCTCTCAGAAGACCCCCAAGCCCCAGACCAAGGAGCTGATGCACTTGTGCATGCGGCAGGAGGCCT
ACCTAGAGGCCCTCTCCCACCTGCAGTCCCCACTCGACCCCAGCACCCTGCTGGCTGAAGTCTGCGTGGA
GCAGTGCACCTTCATGGACTCCAAGATGAAGCCCCTGTGGATCATGTACAGCAACGAGGAGGCAGGCAGC
GGCGGCAGCGTGGGCATCATCTTTAAGAACGGGGATGACCTCCGGCAGGACATGCTGACCCTGCAGATGA
TCCAGCTCATGGACGTCCTGTGGAAGCAGGAGGGGCTGGACCTGAGGATGACCCCCTATGGCTGCCTCCC
CACCGGGGACCGCACAGGCCTCATTGAGGTGGTACTCCGTTCAGACACCATCGCCAACATCCAACTCAAC
AAGAGCAACATGGCAGCCACAGCCGCCTTCAACAAGGATGCCCTGCTCAACTGGCTGAAGTCCAAGAACC
CGGGGGAGGCCCTGGATCGAGCCATTGAGGAGTTCACCCTCTCCTGTGCTGGCTATTGTGTGGCCACATA
TGTGCTGGGCATTGGCGATCGGCACAGCGACAACATCATGATCCGAGAGAGTGGGCAGCTGTTCCACATT
GATTTTGGCCACTTTCTGGGGAATTTCAAGACCAAGTTTGGAATCAACCGCGAGCGTGTCCCATTCATCC
```

TABLE 2 -continued

PIK3CD (Full length) Nucleotide Sequence (3135 nt, SEQ ID No. 1)

TCACCTACGACTTTGTCCATGTGATTCAGCGGGGAAGACTAATAATAGTTGAGAAATTTGAACGGTTCCG

GGGCTACTGTGAAAGGGCCTACACCATCCTGCGGCGCCACGGGCTTCTCTTCCTCCACCTCTTTGCCCTG

ATGCGGGCGGCAGGCCTGCCTGAGCTCAGCTGCTCCAAAGACATCCAGTATCTCAAGGACTCCCTGGCAC

TGGGGAAAACAGAGGAGGAGGCACTGAAGCACTTCCGAGTGAAGTTTAACGAAGCCCTCCGTGAGAGCTG

GAAAACCAAAGTGAACTGGCTGGCCCACAACGTGTCCAAAGACAACAGGCAGTAG (Exon 10 is indicated by double underline, Exon 23 is indicated by wave underline. Primers for qRT-PCR validations of PIK3CD splice variants (-L and -S forms) are underlined)

TABLE 3

PIK3CD variant 1 (lacking exon 10) Nucleotide Sequence (3045 nt, SEQ ID No. 7)

ATGCCCCCTGGGGTGGACTGCCCCATGGAATTCTGGACCAAGGAGGAGAATCAGAGCGTTGTGGTTGACT

TCCTGCTGCCCACAGGGGTCTACCTGAACTTCCCTGTGTCCCGCAATGCCAACCTCAGCACCATCAAGCA

GCTGCTGTGGCACCGCGCCCAGTATGAGCCGCTCTTCCACATGCTCAGTGGCCCCGAGGCCTATGTGTTC

ACCTGCATCAACCAGACAGCGGAGCAGCAAGAGCTGGAGGACGAGCAACGGCGTCTGTGTGACGTGCAGC

CCTTCCTGCCCGTCCTGCGCCTGGTGGCCCGTGAGGGCGACCGCGTGAAGAAGCTCATCAACTCACAGAT

CAGCCTCCTCATCGGCAAAGGCCTCCACGAGTTTGACTCCTTGTGCGACCCAGAAGTGAACGACTTTCGC

GCCAAGATGTGCCAATTCTGCGAGGAGGCGGCCGCCCGCCGGCAGCAGCTGGGCTGGGAGGCCTGGCTGC

AGTACAGTTTCCCCCTGCAGCTGGAGCCCTCGGCTCAAACCTGGGGGCCTGGTACCCTGCGGCTCCCGAA

CCGGGCCCTTCTGGTCAACGTTAAGTTTGAGGGCAGCGAGGAGAGCTTCACCTTCCAGGTGTCCACCAAG

GACGTGCCGCTGGCGCTGATGGCCTGTGCCCTGCGGAAGAAGGCCACAGTGTTCCGGCAGCCGCTGGTGG

AGCAGCCGGAAGACTACACGCTGCAGGTGAACGGCAGGCATGAGTACCTGTATGGCAGCTACCCGCTCTG

CCAGTTCCAGTACATCTGCAGCTGCCTGCACAGTGGGTTGACCCCTCACCTGACCATGGTCCATTCCTCC

TCCATCCTCGCCATGCGGGATGAGCAGAGCAACCCTGCCCCCCAGGTCCAGAAACCGCGTGCCAAACCAC

CTCCCATTCCTGCGAAGAAGCTGGTGGTGCAGGCCGGGCTTTTCCACGGCAACGAGATGCTGTGCAAGACGG

TGTCCAGCTCGAGGTGAGCGTGTGCTCGGAGCCCGTGTGGAAGCAGCGGCTGGAGTTCGACATCAACATCT

GCGACCTGCCCCGCATGGCCCGTCTCTGCTTTGCGCTGTACGCCGTGATCGAGAAAGCCAAGAAGGCTCGCT

CCACCAAGAAGAAGTCCAAGAAGGCGGACTGCCCCATTGCCTGGGCAACCTCATGCTGTTTGACTACAAGG

ACCAGCTTAAGACCGGGGAACGCTGCCTCTACATGTGGCCCTCCGTCCCAGATGAGAAGGGCGAGCTGCTGA

ACCCCACGGGCACTGTGCGCAGTAACCCCAACACGGATAGCGCCGCTGCCCTGCTCATCTGCCTGCCCGAGG

TGGCCCCGCACCCCGTGTACTACCCCGCCCTGGAGAAGATCTTGGAGCTGGGGCGACACAGCGAGTGTGTGC

ATGTCACCGAGGAGGAGCAGCTGCAGCTGCGGGAAATCCTGGAGCGGCGGGGGTCTGGGGAGCTGTATGAGC

ACGAGAAGGACCTGGTGTGGAAGCTGCGGCATGAAGTCCAGGAGCACTTCCCGGAGGCGCTAGCCCGGCTGC

TGCTGGTCACCAAGTGGAACAAGCATGAGGATGTGGCCCAGATGCTCTACCTGCTGTGCTCCTGGCCGGAGC

TGCCCGTCCTGAGCGCCCTGGAGCTGCTAGACTTCAGCTTCCCCGATTGCCACGTAGGCTCCTTCGCCATCA

AGTCGCTGCGGAAACTGACGGACGATGAGCTGTTCCAGTACCTGCTGCAGCTGGTGCAGGTGCTCAAGTACG

AGTCCTACCTGGACTGCGAGCTGACCAAATTCCTGCTGGACCGGGCCCTGGCCAACCGCAAGATCGGCCACT

TCCTTTTCTGGCACCTCCGCTCCGAGATGCACGTGCCGTCGGTGGCCCTGCGCTTCGGCCTCATCCTGGAGG

CCTACTGCAGGGGCAGCACCCACCACATGAAGGTGCTGATGAAGCAGGGGGAAGCACTGAGCAAACTGAAGG

CCCTGAATGACTTCGTCAAGCTGAGCTCTCAGAAGACCCCCAAGCCCCAGACCAAGGAGCTGATGCACTTGT

TABLE 3-continued

PIK3CD variant 1 (lacking exon 10) Nucleotide Sequence (3045 nt, SEQ ID No. 7)

```
GCATGCGGCAGGAGGCCTACCTAGAGGCCCTCTCCCACCTGCAGTCCCCACTCGACCCCAGCACCCTGCTGG
CTGAAGTCTGCGTGGAGCAGTGCACCTTCATGGACTCCAAGATGAAGCCCCTGTGGATCATGTACAGCAACG
AGGAGGCAGGCAGCGGCGGCAGCGTGGGCATCATCTTTAAGAACGGGGATGACCTCCGGCAGGACATGCTGA
CCCTGCAGATGATCCAGCTCATGGACGTCCTGTGGAAGCAGGAGGGGCTGGACCTGAGGATGACCCCCTATG
GCTGCCTCCCCACCGGGGACCGCACAGGCCTCATTGAGGTGGTACTCCGTTCAGACACCATCGCCAACATCC
AACTCAACAAGAGCAACATGGCAGCCACAGCCGCCTTCAACAAGGATGCCCTGCTCAACTGGCTGAAGTCCA
AGAACCCGGGGAGGCCCTGGATCGAGCCATTGAGGAGTTCACCCTCTCCTGTGCTGGCTATTGTGTGGCCA
CATATGTGCTGGGCATTGGCGATCGGCACAGCGACAACATCATGATCCGAGAGAGTGGGCAGCTGTTCCACA
TTGATTTTGGCCACTTTCTGGGGAATTTCAAGACCAAGTTTGGAATCAACCGCGAGCGTGTCCCATTCATCC
TCACCTACGACTTTGTCCATGTGATTCAGCAGGGGAAGACTAATAATAGTGAGAAATTTGAACGGTTCCGGG
GCTACTGTGAAAGGGCCTACACCATCCTGCGGCGCCACGGGCTTCTCTTCCTCCACCTCTTTGCCCTGATGC
GGGCGGCAGGCCTGCCTGAGCTCAGCTGCTCCAAAGACATCCAGTATCTCAAGGACTCCCTGGCACTGGGGA
AAACAGAGGAGGAGGCACTGAAGCACTTCCGAGTGAAGTTTAACGAAGCCCTCCGTGAGAGCTGGAAAACCA
AAGTGAACTGGCTGGCCCACAACGTGTCCAAAGACAACAGGCAGTAG
```

(Double underline indicates bases bordering the splice junction)

TABLE 4

PIK3CD variant 2 (lacking exon 23) Nucleotide Sequence (2967 nt, SEQ ID No. 11)

```
ATGCCCCCTGGGGTGGACTGCCCCATGGAATTCTGGACCAAGGAGGAGAATCAGAGCGTTGTGGTTGACT
TCCTGCTGCCCACAGGGGTCTACCTGAACTTCCCTGTGTCCCGCAATGCCAACCTCAGCACCATCAAGCA
GCTGCTGTGGCACCGCGCCCAGTATGAGCCGCTCTTCCACATGCTCAGTGGCCCCGAGGCCTATGTGTTC
ACCTGCATCAACCAGACAGCGGAGCAGCAAGAGCTGGAGGACGAGCAACGGCGTCTGTGTGACGTGCAGC
CCTTCCTGCCCGTCCTGCGCCTGGTGGCCCGTGAGGGCGACCGCGTGAAGAAGCTCATCAACTCACAGAT
CAGCCTCCTCATCGGCAAAGGCCTCCACGAGTTTGACTCCTTGTGCGACCCAGAAGTGAACGACTTTCGC
GCCAAGATGTGCCAATTCTGCGAGGAGGCGGCCGCCCGCCGGCAGCAGCTGGGCTGGGAGGCCTGGCTGC
AGTACAGTTTCCCCCTGCAGCTGGAGCCCTCGGCTCAAACCTGGGGCCTGGTACCCTGCGGCTCCCGAA
CCGGGCCCTTCTGGTCAACGTTAAGTTTGAGGGCAGCGAGGAGAGCTTCACCTTCCAGGTGTCCACCAAG
GACGTGCCGCTGGCGCTGATGGCCTGTGCCCTGCGGAAGAAGGCCACAGTGTTCCGGCAGCCGCTGGTGG
AGCAGCCGGAAGACTACACGCTGCAGGTGAACGGCAGGCATGAGTACCTGTATGGCAGCTACCCGCTCTG
CCAGTTCCAGTACATCTGCAGCTGCCTGCACAGTGGGTTGACCCCTCACCTGACCATGGTCCATTCCTCC
TCCATCCTCGCCATGCGGGATGAGCAGAGCAACCCTGCCCCCCAGGTCCAGAAACCGCGTGCCAAACCAC
CTCCCATTCCTGCGAAGAAGCCTTCCTCTGTGTCCCTGTGGTCCCTGGAGCAGCCGTTCCGCATCGAGCT
CATCCAGGGCAGCAAAGTGAACGCCGACGAGCGGATGAAGCTGGTGGTGCAGGCCGGCTTTTCCACGGC
AACGAGATGCTGTGCAAGACGGTGTCCAGCTCGGAGGTGAGCGTGTGCTCGGAGCCCGTGTGGAAGCAGC
GGCTGGAGTTCGACATCAACATCTGCGACCTGCCCCGCATGGCCCGTCTCTGCTTTGCGCTGTACGCCGT
GATCGAGAAAGCCAAGAAGGCTCGCTCCACCAAGAAGAAGTCCAAGAAGGCGGACTGCCCCATTGCCTGG
GCCAACCTCATGCTGTTTGACTACAAGGACCAGCTTAAGACCGGGGAACGCTGCCTCTACATGTGGCCCT
CCGTCCCAGATGAGAAGGGCGAGCTGCTGAACCCCACGGGCACTGTGCGCAGTAACCCCAACACGGATAG
```

TABLE 4-continued

PIK3CD variant 2 (lacking exon 23)Nucleotide Sequence
(2967 nt, SEQ ID No. 11)

CGCCGCTGCCCTGCTCATCTGCCTGCCCGAGGTGGCCCCGCACCCCGTGTACTACCCCGCCCTGGAGAAG

ATCTTGGAGCTGGGGCGACACAGCGAGTGTGTGCATGTCACCGAGGAGGAGCAGCTGCAGCTGCGGGAAA

TCCTGGAGCGGCGGGGGTCTGGGGAGCTGTATGAGCACGAGAAGGACCTGGTGTGGAAGCTGCGGCATGA

AGTCCAGGAGCACTTCCCGGAGGCGCTAGCCCGGCTGCTGCTGGTCACCAAGTGGAACAAGCATGAGGAT

GTGGCCCAGATGCTCTACCTGCTGTGCTCCTGGCCGGAGCTGCCCGTCCTGAGCGCCCTGGAGCTGCTAG

ACTTCAGCTTCCCCGATTGCCACGTAGGCTCCTTCGCCATCAAGTCGCTGCGGAAACTGACGGACGATGA

GCTGTTCCAGTACCTGCTGCAGCTGGTGCAGGTGCTCAAGTACGAGTCCTACCTGGACTGCGAGCTGACC

AAATTCCTGCTGGACCGGGCCCTGGCCAACCGCAAGATCGGCCACTTCCTTTTCTGGCACCTCCGCTCCG

AGATGCACGTGCCGTCGGTGGCCCTGCGCTTCGGCCTCATCCTGGAGGCCTACTGCAGGGGCAGCACCCA

CCACATGAAGGTGCTGATGAAGCAGGGGGAAGCACTGAGCAAACTGAAGGCCCTGAATGACTTCGTCAAG

CTGAGCTCTCAGAAGACCCCCAAGCCCCAGACCAAGGAGCTGATGCACTTGTGCATGCGGCAGGAGGCCT

ACCTAGAGGCCCTCTCCCACCTGCAGTCCCCACTCGACCCCAGCACCCTGCTGGCTGAAGTCTGCGTGGA

GCAGTGCACCTTCATGGACTCCAAGATGAAGCCCCTGTGGATCATGTACAGCAACGAGGAGGCAGGCAGC

GGCGGCAGCGTGGGCATCATCTTTAAGAACGGGGATGACCTCCGGCAGGACATGCTGACCCTGCAGATGA

TCCAGCTCATGGACGTCCTGTGGAAGCAGGAGGGGCTGGACCTGAGGGAGGCCCTGGATCGAGCCATTGAGG

AGTTCACCCTCTCCTGTGCTGGCTATTGTGTGGCCACATATGTGCTGGGCATTGGCGATCGGCACAGCGACA

ACATCATGATCCGAGAGAGTGGGCAGCTGTTCCACATTGATTTTGGCCACTTTCTGGGGAATTTCAAGACCA

AGTTTGGAATCAACCGCGAGCGTGTCCCATTCATCCTCACCTACGACTTTGTCCATGTGATTCAGCAGGGGA

AGACTAATAATAGTGAGAAATTTGAACGGTTCCGGGGCTACTGTGAAAGGGCCTACACCATCCTGCGGCGCC

ACGGGCTTCTCTTCCTCCACCTCTTTGCCCTGATGCGGGCGGCAGGCCTGCCTGAGCTCAGCTGCTCCAAAG

ACATCCAGTATCTCAAGGACTCCCTGGCACTGGGGAAAACAGAGGAGGAGGCACTGAAGCACTTCCGAGTGA

AGTTTAACGAAGCCCTCCGTGAGAGCTGGAAAACCAAAGTGAACTGGCTGGCCCACAACGTGTCCAAAGACA

ACAGGCAGTAG (Double underline indicates bases bordering the splice junction)

TABLE 5

PIK3CD variant 3 (lacking exon 10 and exon 23)
Nucleotide Sequence (2877 nt, SEQ ID No. 14):

ATGCCCCCTGGGGTGGACTGCCCCATGGAATTCTGGACCAAGGAGGAGAATCAGAGCGTTGTGGTTGACT

TCCTGCTGCCCACAGGGGTCTACCTGAACTTCCCTGTGTCCCGCAATGCCAACCTCAGCACCATCAAGCA

GCTGCTGTGGCACCGCGCCCAGTATGAGCCGCTCTTCCACATGCTCAGTGGCCCCGAGGCCTATGTGTTC

ACCTGCATCAACCAGACAGCGGAGCAGCAAGAGCTGGAGGACGAGCAACGGCGTCTGTGTGACGTGCAGC

CCTTCCTGCCCGTCCTGCGCCTGGTGGCCCGTGAGGGCGACCGCGTGAAGAAGCTCATCAACTCACAGAT

CAGCCTCCTCATCGGCAAAGGCCTCCACGAGTTTGACTCCTTGTGCGACCCAGAAGTGAACGACTTTCGC

GCCAAGATGTGCCAATTCTGCGAGGAGGCGGCCGCCCGCCGGCAGCAGCTGGGCTGGGAGGCCTGGCTGC

AGTACAGTTTCCCCCTGCAGCTGGAGCCCTCGGCTCAAACCTGGGGGCCTGGTACCCTGCGGCTCCCGAA

CCGGGCCCTTCTGGTCAACGTTAAGTTTGAGGGCAGCGAGGAGAGCTTCACCTTCCAGGTGTCCACCAAG

GACGTGCCGCTGGCGCTGATGGCCTGTGCCCTGCGGAAGAAGGCCACAGTGTTCCGGCAGCCGCTGGTGG

AGCAGCCGGAAGACTACACGCTGCAGGTGAACGGCAGGCATGAGTACCTGTATGGCAGCTACCCGCTCTG

TABLE 5-continued

PIK3CD variant 3 (lacking exon 10 and exon 23)
Nucleotide Sequence (2877 nt, SEQ ID No. 14):

CCAGTTCCAGTACATCTGCAGCTGCCTGCACAGTGGGTTGACCCCTCACCTGACCATGGTCCATTCCTCC

TCCATCCTCGCCATGCGGGATGAGCAGAGCAACCCTGCCCCCCAGGTCCAGAAACCGCGTGCCAAACCAC

CTCCCATTCCTGCGAAGAAGCTGGTGGTGCAGGCCGGGCTTTTCCACGGCAACGAGATGCTGTGCAAGACGG

TGTCCAGCTCGGAGGTGAGCGTGTGCTCGGAGCCCGTGTGGAAGCAGCGGCTGGAGTTCGACATCAACATCT

GCGACCTGCCCCGCATGGCCCGTCTCTGCTTTGCGCTGTACGCCGTGATCGAGAAAGCCAAGAAGGCTCGCT

CCACCAAGAAGAAGTCCAAGAAGGCGGACTGCCCCATTGCCTGGGCCAACCTCATGCTGTTTGACTACAAGG

ACCAGCTTAAGACCGGGGAACGCTGCCTCTACATGTGGCCCTCCGTCCCAGATGAGAAGGGCGAGCTGCTGA

ACCCCACGGGCACTGTGCGCAGTAACCCCAACACGGATAGCGCCGCTGCCCTGCTCATCTGCCTGCCCGAGG

TGGCCCCGCACCCCGTGTACTACCCCGCCCTGGAGAAGATCTTGGAGCTGGGGCGACACAGCGAGTGTGTGC

ATGTCACCGAGGAGGAGCAGCTGCAGCTGCGGGAAATCCTGGAGCGGCGGGGGTCTGGGGAGCTGTATGAGC

ACGAGAAGGACCTGGTGTGGAAGCTGCGGCATGAAGTCCAGGAGCACTTCCCGGAGGCGCTAGCCCGGCTGC

TGCTGGTCACCAAGTGGAACAAGCATGAGGATGTGGCCCAGATGCTCTACCTGCTGTGCTCCTGGCCGGAGC

TGCCCGTCCTGAGCGCCCTGGAGCTGCTAGACTTCAGCTTCCCCGATTGCCACGTAGGCTCCTTCGCCATCA

AGTCGCTGCGGAAACTGACGGACGATGAGCTGTTCCAGTACCTGCTGCAGCTGGTGCAGGTGCTCAAGTACG

AGTCCTACCTGGACTGCGAGCTGACCAAATTCCTGCTGGACCGGGCCCTGGCCAACCGCAAGATCGGCCACT

TCCTTTTCTGGCACCTCCGCTCCGAGATGCACGTGCCGTCGGTGGCCCTGCGCTTCGGCCTCATCCTGGAGG

CCTACTGCAGGGGCAGCACCCACCACATGAAGGTGCTGATGAAGCAGGGGGAAGCACTGAGCAAACTGAAGG

CCCTGAATGACTTCGTCAAGCTGAGCTCTCAGAAGACCCCCAAGCCCCAGACCAAGGAGCTGATGCACTTGT

GCATGCGGCAGGAGGCCTACCTAGAGGCCCTCTCCCACCTGCAGTCCCCACTCGACCCCAGCACCCTGCTGG

CTGAAGTCTGCGTGGAGCAGTGCACCTTCATGGACTCCAAGATGAAGCCCCTGTGGATCATGTACAGCAACG

AGGAGGCAGGCAGCGGCGGCAGCGTGGGCATCATCTTTAAGAACGGGGATGACCTCCGGCAGGACATGCTGA

CCCTGCAGATGATCCAGCTCATGGACGTCCTGTGGAAGCAGGAGGGGCTGGACCTGAGGGAGGCCCTGGATC

GAGCCATTGAGGAGTTCACCCTCTCCTGTGCTGGCTATTGTGTGGCCACATATGTGCTGGGCATTGGCGATC

GGCACAGCGACAACATCATGATCCGAGAGAGTGGGCAGCTGTTCCACATTGATTTTGGCCACTTTCTGGGGA

ATTTCAAGACCAAGTTTGGAATCAACCGCGAGCGTGTCCCATTCATCCTCACCTACGACTTTGTCCATGTGA

TTCAGCAGGGGAAGACTAATAATAGTGAGAAATTTGAACGGTTCCGGGGCTACTGTGAAAGGGCCTACACCA

TCCTGCGGCGCCACGGGCTTCTCTTCCTCCACCTCTTTGCCCTGATGCGGGCGGCAGGCCTGCCTGAGCTCA

GCTGCTCCAAAGACATCCAGTATCTCAAGGACTCCCTGGCACTGGGGAAAACAGAGGAGGAGGCACTGAAGC

ACTTCCGAGTGAAGTTTAACGAAGCCCTCCGTGAGAGCTGGAAAACCAAAGTGAACTGGCTGGCCCACAACG

TGTCCAAAGACAACAGGCAGTAG (Double underline indicates bases bordering the splice junction)

TABLE 6

PIK3CD variant 4 (with large deletion) Nucleotide
Sequence (1836 nt, SEQ ID No. 16):

ATGCCCCCTGGGGTGGACTGCCCCATGGAATTCTGGACCAAGGAGGAGAATCAGAGCGTTGTGGTTGACT

TCCTGCTGCCCACAGGGGTCTACCTGAACTTCCCTGTGTCCCGCAATGCCAACCTCAGCACCATCAAGCA

TABLE 6-continued

PIK3CD variant 4 (with large deletion) Nucleotide
Sequence (1836 nt, SEQ ID No. 16):

GCTGCTGTGGCACCGCGCCCAGTATGAGCCGCTCTTCCACATGCTCAGTGGCCCCGAGGCCTATGTGTTC
ACCTGCATCAACCAGACAGCGGAGCAGCAAGAGCTGGAGGACGAGCAACGGCGTCTGTGTGACGTGCAGC
CCTTCCTGCCCGTCCTGCGCCTGGTGGCCCGTGAGGGCGACCGCGTGAAGAAGCTCATCAACTCACAGAT
CAGCCTCCTCATCGGCAAAGGCCTCCACGAGTTTGACTCCTTGTGCGACCCAGAAGTGAACGACTTTCGC
GCCAAGATGTGCCAATTCTGCGAGGAGGCGGCCGCCCGCCGGCAGCAGCTGGGCTGGGAGGCCTGGCTGC
AGTACAGTTTCCCCCTGCAGCTGGAGCCCTCGGCTCAAACCTGGGGGCCTGGTACCCTGCGGCTCCCGAA
CCGGGCCCTTCTGGTCAACGTTAAGTTTGAGGGCAGCGAGGAGAGCTTCACCTTCCAGGTGTCCACCAAG
GACGTGCCGCTGGCGCTGATGGCCTGTCCCTGCGGAAGAAGGCCACAGTGTTCCGGCAGCCGCTGGTGG
AGCAGCCGGAAGACTACACGCTGCAGGTGAACGGCAGGCATGAGTACCTGTATGGCAGCTACCCGCTCTG
CCAGTTCCAGTACATCTGCAGCTGCCTGCACAGTGGGTTGACCCCTCACCTGACCATGGTCCATTCCTCC
TCCATCCTCGCCATGCGGGATGAGCAGAGCAACCCTGCCCCCCAGGTCCAGAAACCGCGTGCCAAACCAC
CTCCCATTCCTGCGAAGAAGCCTTCCTCTGTGTCCCTGTGGTCCCTGGAGCAGCCGTTCCGCATCGAGCT
CATCCAGGGCAGCAAAGTGAACGCCGACGAGCGGATGAAGCTGGTGGTGCAGGCCGGGCTTTTCCACGGC
AACGAGATGCTGTGCAAGACGGTGTCCAGCTCGGAGGTGAGCGTGTGCTCGGAGCCCGTGTGGAAGCAGC
GGCTGGAGTTCGACATCAACATCTGCGACCTGCCCCGCATGGCCCGTCTCTGCTTTGCGCTGTACGCCGT
GATCGAGAAGCCAAGAAGGCTCGCTCCACCAAGAAGAAGTCCAAGAAGGCGGACTGCCCCATTGCCTGG
GCCAACCTCATGCTGTTTGACTACAAGGACCAGCTTAAGACCGGGGAACGCTGCCTCTACATGTGGCCCCTC
TCCTGTGCTGGCTATTGTGTGGCCACATATGTGCTGGGCATTGGCGATCGGCACAGCGACAACATCATGATC
CGAGAGAGTGGGCAGCTGTTCCACATTGATTTTGGCCACTTTCTGGGGAATTTCAAGACCAAGTTTGGAATC
AACCGCGAGCGTGTCCCATTCATCCTCACCTACGACTTTGTCCATGTGATTCAGCAGGGGAAGACTAATAAT
AGTGAGAAATTTGAACGGTTCCGGGGCTACTGTGAAAGGGCCTACACCATCCTGCGGCGCCACGGGCTTCTC
TTCCTCCACCTCTTTGCCCTGATGCGGGCGGCAGGCCTGCCTGAGCTCAGCTGCTCCAAAGACATCCAGTAT
CTCAAGGACTCCCTGGCACTGGGGAAAACAGAGGAGGAGGCACTGAAGCACTTCCGAGTGAAGTTTAACGAA
GCCCTCCGTGAGAGCTGGAAAACCAAAGTGAACTGGCTGGCCCACAACGTGTCCAAAGACAACAGGCAGTAG (Double underline indicates bases bordering the deletion junction)

| TABLE 7 | |
|---|---|
| Primers for detecting PIK3CD variants | |
| Primer across the junction between PIK3CD exon 9 and 11 (SEQ ID No. 6) | TGCGAAGAAGCTGGTGGTGC |
| Primer sequences across the junct. between PIK3CD exon 22 and 24 (SEQ ID No. 10) | TGGACCTGAGGGAGGCCCT |
| Primer sequences across the deleted region (nt1329-2627) of PIK3CD (SEQ ID No. 15): | ACATGTGGCCCCTCTCCTG |

(Double underline indicates bases bordering the splice junction)

| TABLE 8 |
|---|
| siRNA for selectively knockdown PIK3CD full length and variants expression |
| siRNA targeting PIK3CD exon 23 (siPIK3CD-ex23) |
| Sense (SEQ ID No. 4): 5' CCAACAUCCAACUCAACAAdTdT 3' |
| Antisense (SEQ ID No. 5): 3' dTdTGGUUGUAGGUUGAGUU-GUU (5'-P)5' |
| siRNA targeting junction spanning between exon 9 and exon 11 |
| Sense (SEQ ID No. 8) 5' CUGCGAAGAAGCUGGUGGUdTdT 3' |
| Antisense (SEQ ID No. 9) 3' dTdTGACGCUUCUUCGACCAC-CA (5'-P)5' |

TABLE 8-continued siRNA for selectively knockdown PIK3CD full length and variants expression siRNA targeting junction spanning between PIK3CD exon22 and exon 24 (siPIK3CD-S)

Sense (SEQ ID No. 12) 5' UGAGGGAGGCCCUGGAUCGAdTdT 3'

Antisense (SEQ ID No. 13) 3' dTdTACUCCCUCCGGGACCU-AGCU (5'-P)5' siRNA targeting junction spanning the deleted sequences of PIK3CD variant 4

Sense (SEQ ID No. 17) 5' CCUCUCCUGUGCUGGCUAUdTdT 3'

Antisense (SEQ ID No. 18) 3' dTdTGGAGAGGACACGACCG-AUA (5'-P)5'

(Double underline indicates bases bordering the splice junction)

TABLE 9

FGFR3 (Full length) Nucleotide Sequence (2421 nt, SEQ ID No. 19)

ATGGGCGCCCCTGCCTGCGCCCTCGCGCTCTGCGTGGCCGTGGCCATCGT
GGCCGGCGCCTCCTCGGAGTCCTTGGGGACGGAGCAGCGCGTCGTGGGGC
GAGCGGCAGAAGTCCCGGGCCCAGAGCCCGGCCAGCAGGAGCAGTTGGTC
TTCGGCAGCGGGGATGCTGTGGAGCTGAGCTGTCCCCCGCCCGGGGGTGG
TCCCATGGGGCCCACTGTCTGGGTCAAGGATGGCACAGGGCTGGTGCCCT
CGGAGCGTGTCCTGGTGGGGCCCCAGCGGCTGCAGGTGCTGAATGCCTCC
CACGAGGACTCCGGGGCCTACAGCTGCCGGCAGCGGCTCACGCAGCGCGT
ACTGTGCCACTTCAGTGTGCGGGTGACAGACGCTCCATCCTCGGGAGATG
ACGAAGACGGGGAGGACGAGGCTGAGGACACAGGTGTGGACACAGGGGCC
CCTTACTGGACACGGCCCGAGCGGATGGACAAGAAGCTGCTGGCCGTGCC
GGCCGCCAACACCGTCCGCTTCCGCTGCCCAGCCGCTGGCAACCCCACTC
CCTCCATCTCCTGGCTGAAGAACGGCAGGGAGTTCCGCGGCGAGCACCGC
ATTGGAGGCATCAAGCTGCGGCATCAGCAGTGGAGCCTGGTCATGGAAAG
CGTGGTGCCCTCGGACCGCGGCAACTACACCTGCGTCGTGGAGAACAAGT
TTGGCAGCATCCGGCAGACGTACACGCTGGACGTGCTGGAGCGCTCCCCG
CACCGGCCCATCCTGCAGGCGGGGCTGCCGGCCAACCAGACGGCGGTGCT
GGGCAGCGACGTGGAGTTCCACTGCAAGGTGTACAGTGACGCACAGCCCC
ACATCCAGTGGCTCAAGCACGTGGAGGTGAATGGCAGCAAGGTGGGCCCG
GACGGCACACCCTACGTTACCGTGCTCAAGACGGCGGGCGCTAACACCAC
CGACAAGGAGCTAGAGGTTCTCTCCTTGCACAACGTCACCTTTGAGGACG
CCGGGGAGTACACCTGCCTGGCGGGCAATTCTATTGGGTTTTCTCATCAC
TCTGCGTGGCTGGTGGTGCTGCCAGCCGAGGAGGAGCTGGTGGAGGCTGA
CGAGGCGGGCAGTGTGTATGCAGGCATCCTCAGCTACGGGGTGGGCTTCT
TCCTGTTCATCCTGGTGGTGGCGGCTGTGACGCTCTGCCGCCTGCGCAGC
CCCCCCAAGAAAGGCCTGGGCTCCCCCACCGTGCACAAGATCTCCCGCTT

TABLE 9-continued

FGFR3 (Full length) Nucleotide Sequence (2421 nt, SEQ ID No. 19)

CCCGCTCAAGCGACAGGTGTCCCTGGAGTCCAACGCGTCCATGAGCTCCA
ACACACCACTGGTGCGCATCGCAAGGCTGTCCTCAGGGGAGGGCCCCACG
CTGGCCAATGTCTCCGAGCTCGAGCTGCCTGCCGACCCCAAATGGGAGCT
GTCTCGGGCCCGGCTGACCCTGGGCAAGCCCCTTGGGGAGGGCTGCTTCG
GCCAGGTGGTCATGGCGGAGGCCATCGGCATTGACAAGGACCGGGCCGCC
AAGCCTGTCACCGTAGCCGTGAAGATGCTGAAAGACGATGCCACTGACAA
GGACCTGTCGGACCTGGTGTCTGAGATGGAGATGATGAAGATGATCGGGA
AACACAAAAACATCATCAACCTGCTGGGCGCCTGCACGCAGGGCGGGCCC
CTGTACGTGCTGGTGGAGTACGCGGCCAAGGGTAACCTGCGGGAGTTTCT
GCGGGCGCGGCGGCCCCCGGGCCTGGACTACTCCTTCGACACCTGCAAGC
CGCCCGAGGAGCAGCTCACCTTCAAGGACCTGGTGTCCTGTGCCTACCAG
GTGGCCCGGGGCATGGAGTACTTGGCCTCCCAGAAGTGCATCCACAGGGA
CCTGGCTGCCCGCAATGTGCTGGTGACCGAGGACAACGTGATGAAGATCG
CAGACTTCGGGCTGGCCCGGGACGTGCACAACCTCGACTACTACAAGAAG
ACGACCAACGGCCGGCTGCCCGTGAAGTGGATGGCGCCTGAGGCCTTGTT
TGACCGAGTCTACACTCACCAGAGTGACGTCTGGTCCTTTGGGGTCCTGC
TCTGGGAGATCTTCACGCTGGGGGGCTCCCCGTACCCCGGCATCCCTGTG
GAGGAGCTCTTCAAGCTGCTGAAGGAGGGCCACCGCATGGACAAGCCCGC
CAACTGCACACACGACCTGTACATGATCATGCGGGAGTGCTGGCATGCCG
CGCCCTCCCAGAGGCCCACCTTCAAGCAGCTGGTGGAGGACCTGGACCGT
GTCCTTACCGTGACGTCCACCGACGAGTACCTGGACCTGTCGGCGCCTTT
CGAGCAGTACTCCCCGGGTGGCCAGGACACCCCCAGCTCCAGCTCCTCAG
GGGACGACTCCGTGTTTGCCCACGACCTGCTGCCCCCGGCCCCACCCAGC
AGTGGGGGCTCGCGGACGTGA (Exon 14 is indicated by double underline. Primers useful for detection of exon 14 splicing variants are underlined.)

TABLE 10

FGFR3 variant 1 (lacking exon 14) Nucleotide Sequence (2298 nt, SEQ ID No. 25):

ATGGGCGCCCCTGCCTGCGCCCTCGCGCTCTGCGTGGCCGTGGCCATCGT
GGCCGGCGCCTCCTCGGAGTCCTTGGGGACGGAGCAGCGCGTCGTGGGGC
GAGCGGCAGAAGTCCCGGGCCCAGAGCCCGGCCAGCAGGAGCAGTTGGTC
TTCGGCAGCGGGGATGCTGTGGAGCTGAGCTGTCCCCCGCCCGGGGGTGG
TCCCATGGGGCCCACTGTCTGGGTCAAGGATGGCACAGGGCTGGTGCCCT
CGGAGCGTGTCCTGGTGGGGCCCCAGCGGCTGCAGGTGCTGAATGCCTCC
CACGAGGACTCCGGGGCCTACAGCTGCCGGCAGCGGCTCACGCAGCGCGT
ACTGTGCCACTTCAGTGTGCGGGTGACAGACGCTCCATCCTCGGGAGATG
ACGAAGACGGGGAGGACGAGGCTGAGGACACAGGTGTGGACACAGGGGCC
CCTTACTGGACACGGCCCGAGCGGATGGACAAGAAGCTGCTGGCCGTGCC

TABLE 10-continued

FGFR3 variant 1 (lacking exon 14) Nucleotide Sequence (2298 nt, SEQ ID No. 25):

GGCCGCCAACACCGTCCGCTTCCGCTGCCCAGCCGCTGGCAACCCCACTC

CCTCCATCTCCTGGCTGAAGAACGGCAGGGAGTTCCGCGGCGAGCACCGC

ATTGGAGGCATCAAGCTGCGGCATCAGCAGTGGAGCCTGGTCATGGAAAG

CGTGGTGCCCTCGGACCGCGGCAACTACACCTGCGTCGTGGAGAACAAGT

TTGGCAGCATCCGGCAGACGTACACGCTGGACGTGCTGGAGCGCTCCCCG

CACCGGCCCATCCTGCAGGCGGGGCTGCCGGCCAACCAGACGGCGGTGCT

GGGCAGCGACGTGGAGTTCCACTGCAAGGTGTACAGTGACGCACAGCCCC

ACATCCAGTGGCTCAAGCACGTGGAGGTGAATGGCAGCAAGGTGGGCCCG

GACGGCACACCCTACGTTACCGTGCTCAAGACGGCGGGCGCTAACACCAC

CGACAAGGAGCTAGAGGTTCTCTCCTTGCACAACGTCACCTTTGAGGACG

CCGGGGAGTACACCTGCCTGGCGGGCAATTCTATTGGGTTTTCTCATCAC

TCTGCGTGGCTGGTGGTGCTGCCAGCCGAGGAGGAGCTGGTGGAGGCTGA

CGAGGCGGGCAGTGTGTATGCAGGCATCCTCAGCTACGGGGTGGGCTTCT

TCCTGTTCATCCTGGTGGTGGCGGCTGTGACGCTCTGCCGCCTGCGCAGC

CCCCCCAAGAAAGGCCTGGGCTCCCCCACCGTGCACAAGATCTCCCGCTT

CCCGCTCAAGCGACAGGTGTCCCTGGAGTCCAACGCGTCCATGAGCTCCA

ACACACCACTGGTGCGCATCGCAAGGCTGTCCTCAGGGGAGGGCCCCACG

CTGGCCAATGTCTCCGAGCTCGAGCTGCCTGCCGACCCCAAATGGGAGCT

GTCTCGGGCCCGGCTGACCCTGGGCAAGCCCCTTGGGGAGGGCTGCTTCG

GCCAGGTGGTCATGGCGGAGGCCATCGGCATTGACAAGGACCGGGCCGCC

AAGCCTGTCACCGTAGCCGTGAAGATGCTGAAAGACGATGCCACTGACAA

GGACCTGTCGGACCTGGTGTCTGAGATGGAGATGATGAAGATGATCGGGA

AACACAAAAACATCATCAACCTGCTGGGCGCCTGCACGCAGGGCGGGCCC

CTGTACGTGCTGGTGGAGTACGCGGCCAAGGGTAACCTGCGGGAGTTTCT

GCGGGCGCGGCGGCCCCCGGGCCTGGACTACTCCTTCGACACCTGCAAGC

CGCCCGAGGAGCAGCTCACCTTCAAGGACCTGGTGTCCTGTGCCTACCAG

GTGGCCCGGGGCATGGAGTAC<u>TTGGCCTCCCAGAAG</u><u>GGCCGGCT</u>GCCCGT

GAAGTGGATGGCGCCTGAGGCCTTGTTTGACCGAGTCTACACTCACCAGA

GTGACGTCTGGTCCTTTGGGGTCCTGCTCTGGGAGATCTTCACGCTGGGG

GGCTCCCCGTACCCCGGCATCCCTGTGGAGGAGCTCTTCAAGCTGCTGAA

GGAGGGCCACCGCATGGACAAGCCCGCCAACTGCACACACGACCTGTACA

TGATCATGCGGGAGTGCTGGCATGCCGCGCCCTCCCAGAGGCCCACCTTC

AAGCAGCTGGTGGAGGACCTGGACCGTGTCCTTACCGTGACGTCCACCGA

CGAGTACCTGGACCTGTCGGCGCCTTTCGAGCAGTACTCCCCGGGTGGCC

AGGACACCCCCAGCTCCAGCTCCTCAGGGGACGACTCCGTGTTTGCCCAC

GACCTGCTGCCCCCGGCCCCACCCAGCAGTGGGGGCTCGCGGACGTGA (Double underline indicates bases bordering the splice junction)

TABLE 11

Primer across the junction between FGFR3 exon 13 and 15

| Primer across the junction between FGFR3 exon 13 and 15 (SEQ ID No. 24) | TTGGCCTCCCAGAA<u>G</u><u>G</u>GCCGGCT |
|---|---|

(Double underline indicates bases bordering the splice junction)

TABLE 12 siRNA for selectively knockdown FGFR3 full length and variants expression siRNA targeting FGFR3 exon 14:

Sense (SEQ ID No. 22) 5' CUCGACUACUACAAGAAGAdTdT 3'

Antisense (SEQ ID No. 23) 3' dTdTGAGCUGAUGAUGUUCU-UCU (5'-P)5' siRNA targeting splice junction between FGFR3 exon 13 and 15

Sense (SEQ ID No. 26) 5' <u>CCUCCCAGAAG</u><u>GGCCGGCU</u> dTdT 3'

Antisense (SEQ ID No. 27) 3' dTdTGGAGGGUCUU<u>CC</u>CGGC-CGA (5'-P)5'

(Double underline indicates bases bordering the splice junction)

TABLE 13

TSC2 (full length) Nucleotide Sequence (5424 nt, SEQ ID No. 28)

ATGGCCAAACCAACAAGCAAAGATTCAGGCTTGAAGGAGAAGTTTAAGATTCTGTTGGGACTGGGAACACCG

AGGCCAAATCCCAGGTCTGCAGAGGGTAAACAGACGGAGTTTATCATCACCGCGGAAATACTGAGAGAACTG

AGCATGGAATGTGGCCTCAACAATCGCATCCGGATGATAGGGCAGATTTGTGAAGTCGCAAAAACCAAGAAA

TTTGAAGAGCACGCAGTGGAAGCACTCTGGAAGGCGGTCGCGGATCTGTTGCAGCCGGAGCGGCCGCTGGAG

GCCCGGCACGCGGTGCTGGCTCTGCTGAAGGCCATCGTGCAGGGCAGGGCGAGCGTTTGGGGGTCCTCAGA

GCCCTCTTCTTTAAGGTCATCAAGGATTACCCTTCCAACGAAGACCTTCACGAAAGGCTGGAGGTTTTCAAG

GCCCTCACAGACAATGGGAGACACATCACCTACTTGGAGGAAGAGCTGGCTGACTTTGTCCTGCAGTGGATG

TABLE 13-continued

TSC2 (full length)Nucleotide Sequence (5424 nt, SEQ ID No. 28)

GATGTTGGCTTGTCCTCGGAATTCCTTCTGGTGCTGGTGAACTTGGTCAAATTCAATAGCTGTTACCTCGAC

GAGTACATCGCAAGGATGGTTCAGATGATCTGTCTGCTGTGCGTCCGGACCGCGTCCTCTGTGGACATAGAG

GTCTCCCTGCAGGTGCTGGACGCCGTGGTCTGCTACAACTGCCTGCCGGCTGAGAGCCTCCCGCTGTTCATC

GTTACCCTCTGTCGCACCATCAACGTCAAGGAGCTCTGCGAGCCTTGCTGGAAGCTGATGCGGAACCTCCTT

GGCACCCACCTGGGCCACAGCGCCATCTACAACATGTGCCACCTCATGGAGGACAGAGCCTACATGGAGGAC

GCGCCCCTGCTGAGAGGAGCCGTGTTTTTTGTGGGCATGGCTCTCTGGGGAGCCCACCGGCTCTATTCTCTC

AGGAACTCGCCGACATCTGTGTTGCCATCATTTTACCAGGCCATGGCATGTCCGAACGAGGTGGTGTCCTAT

GAGATCGTCCTGTCCATCACCAGGCTCATCAAGAAGTATAGGAAGGAGCTCCAGGTGGTGGCGTGGGACATT

CTGCTGAACATCATCGAACGGCTCCTTCAGCAGCTCCAGACCTTGGACAGCCCGGAGCTCAGGACCATCGTC

CATGACCTGTTGACCACGTGGAGGAGCTGTGTGACCAGAACGAGTTCCACGGGTCTCAGGAGAGATACTTT

GAACTGGTGGAGAGATGTGCGGACCAGAGGCCTGAGTCCTCCCTCCTGAACCTGATCTCCTATAGAGCGCAG

TCCATCCACCCGGCCAAGGACGGCTGGATTCAGAACCTGCAGGCGCTGATGGAGAGATTCTTCAGGAGCGAG

TCCCGAGGCGCCGTGCGCATCAAGGTGCTGGACGTGCTGTCCTTTGTGCTGCTCATCAACAGGCAGTTCTAT

GAGGAGGAGCTGATTAACTCAGTGGTCATCTCGCAGCTCTCCCACATCCCCGAGGATAAAGACCACCAGGTC

CGAAAGCTGGCCACCCAGTTGCTGGTGGACCTGGCAGAGGGCTGCCACACACACCACTTCAACAGCCTGCTG

GACATCATCGAGAAGGTGATGGCCCGCTCCCTCTCCCCACCCCCGGAGCTGGAAGAAAGGGATGTGGCCGCA

TACTCGGCCTCCTTGGAGGATGTGAAGACAGCCGTCCTGGGGCTTCTGGTCATCCTTCAGACCAAGCTGTAC

ACCCTGCCTGCAAGCCACGCCACGCGTGTGTATGAGATGCTGGTCAGCCACATTCAGCTCCACTACAAGCAC

AGCTACACCCTGCCAATCGCGAGCAGCATCCGGCTGCAGGCCTTTGACTTCCTGTTGCTGCTGCGGGCCGAC

TCACTGCACCGCCTGGGCCTGCCCAACAAGGATGGAGTCGTGCGGTTCAGCCCCTACTGCGTCTGCGACTAC

ATGGAGCCAGAGAGAGGCTCTGAGAAGAAGACCAGCGGCCCCCTTTCTCCTCCCACAGGGCCTCCTGGCCCG

GCGCCTGCAGGCCCCGCCGTGCGGCTGGGGTCCGTGCCCTACTCCCTGCTCTTCCGCGTCCTGCTGCAGTGC

TTGAAGCAGGAGTCTGACTGGAAGGTGCTGAAGCTGGTTCTGGGCAGGCTGCCTGAGTCCCTGCGCTATAAA

GTGCTCATCTTTACTTCCCCTTGCAGTGTGGACCAGCTGTGCTCTGCTCTCTGCTCCATGCTTTCAGGCCCA

AAGCACACTGGAGCGGCTCCGAGGCGCCCCAGAAGGCTTCTCCAGAACTGACTTGCACCTGGCCGTGGTTCCA

GTGCTGACAGCATTAATCTCTTACCATAACTACCTGGACAAAACCAAACAGCGCGAGATGGTCTACTGCCTG

GAGCAGGGCCTCATCCACCGCTGTGCCAGCCAGTGCGTCGTGGCCTTGTCCATCTGCAGCGTGGAGATGCCT

GACATCATCATCAAGGCGCTGCCTGTTCTGGTGGTGAAGCTCACGCACATCTCAGCCACAGCCAGCATGGCC

GTCCCACTGCTGGAGTTCCTGTCCACTCTGGCCAGGCTGCCGCACCTCTACAGGAACTTTGCCGCGGAGCAG

TATGCCAGTGTGTTCGCCATCTCCCTGCCGTACACCAACCCCTCCAAGTTTAATCAGTACATCGTGTGTCTG

GCCCATCACGTCATAGCCATGTGGTTCATCAGGTGCCGCCTGCCCTTCCGGAAGGATTTTGTCCCTTTCATC

ACTAAGGGCCTGCGGTCCAATGTCCTCTTGTCTTTTGATGACACCCCGAGAAGGACAGCTTCAGGGCCCGG

AGTACTAGTCTCAACGAGAGACCCAAGAGTCTGAGGATAGCCAGACCCCCCAAACAAGGCTTGAATAACTCT

CCACCCGTGAAAGAATTCAAGGAGAGCTCTGCAGCCGAGGCCTTCCGGTGCCGCAGCATCAGTGTGTCTGAA

CATGTGGTCCGCAGCAGGATACAGACGTCCCTCACCAGTGCCAGCTTGGGGTCTGCAGATGAGAACTCCGTG

GCCCAGGCTGACGATAGCCTGAAAAACCTCCACCTGGAGCTCACGGAAACCTGTCTGGACATGATGGCTCGA

TACGTCTTCTCCAACTTCACGGCTGTCCCGAAGAGGTCTCCTGTGGGCGAGTTCCTCCTAGCGGGTGGCAGG

ACCAAAAACCTGGCTGGTTGGGAACAAGCTTGTCACTGTGACGACAAGCGTGGGAACCGGGACCCGGTCGTTA

CTAGGCCTGGACTCGGGGGAGCTGCAGTCCGGCCCGGAGTCGAGCTCCAGCCCCGGGGTGCATGTGAGACAG

TABLE 13-continued

TSC2 (full length)Nucleotide Sequence (5424 nt, SEQ ID No. 28)

ACCAAGGAGGCGCCGGCCAAGCTGGAGTCCCAGGCTGGGCAGCAGGTGTCCCGTGGGGCCCGGGATCGGGTC

CGTTCCATGTCGGGGGGCCATGGTCTTCGAGTTGGCGCCCTGGACGTGCCGGCCTCCCAGTTCCTGGGCAGT

GCCACTTCTCCAGGACCACGGACTGCACCAGCCGCGAAACCTGAGAAGGCCTCAGCTGGCACCCGGGTTCCT

GTGCAGGAGAAGACGAACCTGGCGGCCTATGTGCCCCTGCTGACCCAGGGCTGGGCGGAGATCCTGGTCCGG

AGGCCCACAGGGAACACCAGCTGGCTGATGAGCCTGGAGAACCCGCTCAGCCCTTTCTCCTCGGACATCAAC

AACATGCCCCTGCAGGAGCTGTCTAACGCCCTCATGGCGGCTGAGCGCTTCAAGGAGCACCGGGACACAGCC

CTGTACAAGTCACTGTCGGTGCCGGCAGCCAGCACGGCCAAACCCCCTCCTCTGCCTCGCTCCAACACAGTG

GCCTCTTTCTCCTCCCTGTACCAGTCCAGCTGCCAAGGACAGCTGCACAGGAGCGTTTCCTGGGCAGACTCC

GCCGTGGTCATGGAGGAGGGAAGTCCGGGCGAGGTTCCTGTGCTGGTGGAGCCCCAGGGTTGGAGGACGTT

GAGGCAGCGCTAGGCATGGACAGGCGCACGGATGCCTACAGCAGGTCGTCCTCAGTCTCCAGCCAGGAGGAG

AAGTCGCTCCACGCGGAGGAGCTGGTTGGCAGGGGCATCCCCATCGAGCGAGTCGTCTCCTCGGAGGGTGGC

CGGCCCTCTGTGGACCTCTCCTTCCAGCCCTCGCAGCCCCTGAGCAAGTCCAGCTCCTCTCCCGAGCTGCAG

ACTCTGCAGGACATCCTCGGGGACCCTGGGGACAAGGCCGACGTGGGCCGGCTGAGCCCTGAGGTTAAGGCC

CGGTCACAGTCAGGGACCCTGGACGGGGAAAGTGCTGCCTGGTCGGCCTCGGGCGAAGACAGTCGGGGCCAG

CCCGAGGGTCCCTTGCCTTCCAGCTCCCCCCGCTCGCCCAGTGGCCTCCGGCCCCGAGGTTACACCATCTCC

GACTCGGCCCCATCACGCAGGGGCAAGAGAGTAGAGAGGGACGCCTTAAAGAGCAGAGCCACAGCCTCCAAT

GCAGAGAAAGTGCCAGGCATCAACCCCAGTTTCGTGTTCCTGCAGCTCTACCATTCCCCCTTCTTTGGCGAC

GAGTCAAACAAGCCAATCCTGCTGCCCAATGAGTCACAGTCCTTTGAGCGGTCGGTGCAGCTCCTCGACCAG

ATCCCATCATACGACACCCACAAGATCGCCGTCCTGTATGTTGGAGAAGGCCAGAGCAACAGCGAGCTCGCC

ATCCTGTCCAATGAGCATGGCTCCTACAGGTACACGGAGTTCCTGACGGGCCTGGGCCGGCTCATCGAGCTG

AAGGACTGCCAGCCGGACAAGGTGTACCTGGGAGGCCTGGACGTGTGTGGTGAGGACGGCCAGTTCACCTAC

TGCTGGCACGATGACATCATGCAAGCCGTCTTCCACATCGCCACCCTGATGCCCACCAAGGACGTGGACAAG

CACCGCTGCGACAAGAAGCGCCACCTGGGCAACGACTTTGTGTCCATTGTCTACAATGACTCCGGTGAGGAC

TTCAAGCTTGGCACCATCAAGGGCCAGTTCAACTTTGTCCACGTGATCGTCACCCCGCTGGACTACGAGTGC

AACCTGGTGTCCCTGCAGTGCAGGAAAGACATGGAGGGCCTTGTGGACACCAGCGTGGCCAAGATCGTGTCT

GACCGCAACCTGCCCTTCGTGGCCCGCCAGATGGCCCTGCACGCAAATATGGCCTCACAGGTGCATCATAGC

CGCTCCAACCCCACCGATATCTACCCCTCCAAGTGGATTGCCCGGCTCCGCCACATCAAGCGGCTCCGCCAG

CGGATCTGCGAGGAAGCCGCCTACTCCAACCCCAGCCTACCTCTGGTGCACCCTCCGTCCCATAGCAAAGCC

CCTGCACAGACTCCAGCCGAGCCCACACCTGGCTATGAGGTGGGCCAGCGGAAGCGCCTCATCTCCTCGGTG

GAGGACTTCACCGAGTTTGTGTGA (Exon 19 is indicated by double underline. Primers useful for detection of exon 19 splicing variants are underlined.)

TABLE 14

TSC2 variant 1 (lacking exon 19) Nucleotide Sequence
(5301 nt, SEQ ID No. 34)

ATGGCCAAACCAACAAGCAAAGATTCAGGCTTGAAGGAGAAGTTTAAGATTCTGTTGGGACTGGGAACACCG

AGGCCAAATCCCAGGTCTGCAGAGGGTAAACAGACGGAGTTTATCATCACCGCGGAAATACTGAGAGAACTG

AGCATGGAATGTGGCCTCAACAATCGCATCCGGATGATAGGGCAGATTTGTGAAGTCGCAAAAACCAAGAAA

TTTGAAGAGCACGCAGTGGAAGCACTCTGGAAGGCGGTCGCGGATCTGTTGCAGCCGGAGCGGCCGCTGGAG

TABLE 14-continued

TSC2 variant 1 (lacking exon 19) Nucleotide Sequence
(5301 nt, SEQ ID No. 34)

```
GCCCGGCACGCGGTGCTGGCTCTGCTGAAGGCCATCGTGCAGGGCAGGGCGAGCGTTTGGGGGTCCTCAGA
GCCCTCTTCTTTAAGGTCATCAAGGATTACCCTTCCAACGAAGACCTTCACGAAAGGCTGGAGGTTTTCAAG
GCCCTCACAGACAATGGGAGACACATCACCTACTTGGAGGAAGAGCTGGCTGACTTTGTCCTGCAGTGGATG
GATGTTGGCTTGTCCTCGGAATTCCTTCTGGTGCTGGTGAACTTGGTCAAATTCAATAGCTGTTACCTCGAC
GAGTACATCGCAAGGATGGTTCAGATGATCTGTCTGCTGTGCGTCCGGACCGCGTCCTCTGTGGACATAGAG
GTCTCCCTGCAGGTGCTGGACGCCGTGGTCTGCTACAACTGCCTGCCGGCTGAGAGCCTCCCGCTGTTCATC
GTTACCCTCTGTCGCACCATCAACGTCAAGGAGCTCTGCGAGCCTTGCTGGAAGCTGATGCGGAACCTCCTT
GGCACCCACCTGGGCCACAGCGCCATCTACAACATGTGCCACCTCATGGAGGACAGAGCCTACATGGAGGAC
GCGCCCCTGCTGAGAGGAGCCGTGTTTTTTGTGGGCATGGCTCTCTGGGGAGCCCACCGGCTCTATTCTCTC
AGGAACTCGCCGACATCTGTGTTGCCATCATTTTACCAGGCCATGGCATGTCCGAACGAGGTGGTGTCCTAT
GAGATCGTCCTGTCCATCACCAGGCTCATCAAGAAGTATAGGAAGGAGCTCCAGGTGGTGGCGTGGGACATT
CTGCTGAACATCATCGAACGGCTCCTTCAGCAGCTCCAGACCTTGGACAGCCCGGAGCTCAGGACCATCGTC
CATGACCTGTTGACCACGGTGGAGGAGCTGTGTGACCAGAACGAGTTCCACGGGTCTCAGGAGAGATACTTT
GAACTGGTGGAGAGATGTGCGGACCAGAGGCCTGAGTCCTCCCTCCTGAACCTGATCTCCTATAGAGCGCAG
TCCATCCACCCGGCCAAGGACGGCTGGATTCAGAACCTGCAGGCGCTGATGGAGAGATTCTTCAGGAGCGAG
TCCCGAGGCGCCGTGCGCATCAAGGTGCTGGACGTGCTGTCCTTTGTGCTGCTCATCAACAGGCAGTTCTAT
GAGGAGGAGCTGATTAACTCAGTGGTCATCTCGCAGCTCTCCCACATCCCCGAGGATAAAGACCACCAGGTC
CGAAAGCTGGCCACCCAGTTGCTGGTGGACCTGGCAGAGGGCTGCCACACACACCACTTCAACAGCCTGCTG
GACATCATCGAGAAGGTGATGGCCCGCTCCCTCTCCCCACCCCCGGAGCTGGAAGAAAGGGATGTGGCCGCA
TACTCGGCCTCCTTGGAGGATGTGAAGACAGCCGTCCTGGGGCTTCTGGTCATCCTTCAGACCAAGCTGTAC
ACCCTGCCTGCAAGCCACGCCACGCGTGTGTATGAGATGCTGGTCAGCCACATTCAGCTCCACTACAAGCAC
AGCTACACCCTGCCAATCGCGAGCAGCATCCGGCTGCAGGCCTTTGACTTCCTGTTGCTGCTGCGGGCCGAC
TCACTGCACCGCCTGGGCCTGCCCAACAAGGATGGAGTCGTGCGGTTCAGCCCCTACTGCGTCTGCGACTAC
ATGGAGCCAGAGAGAGGCTCTGAGAAGAAGACCAGCGGCCCCCTTTCTCCTCCCACAGGGCCTCCTGGCCCG
GCGCCTGCAGGCCCCGCCGTGCGGCTGGGGTCCGTGCCCTACTCCCTGCTCTTCCGCGTCCTGCTGCAGTGC
TTGAAGCAGCTTTCAGGCCCAAAGACACTGGAGCGGCTCCGAGGCGCCCCAGAAGGCTTCTCCAGAACTGAC
TTGCACCTGGCCGTGGTTCCAGTGCTGACAGCATTAATCTCTTACCATAACTACCTGGACAAAACCCAAACAG
CGCGAGATGGTCTACTGCCTGGAGCAGGGCCTCATCCACCGCTGTGCCAGCCAGTGCGTCGTGGCCTTGTCC
ATCTGCAGCGTGGAGATGCCTGACATCATCATCAAGGCGCTGCCTGTTCTGGTGGTGAAGCTCACGCACATC
TCAGCCACAGCCAGCATGGCCGTCCCACTGCTGGAGTTCCTGTCCACTCTGGCCAGGCTGCCGCACCTCTAC
AGGAACTTTGCCGCGGAGCAGTATGCCAGTGTGTTCGCCATCTCCCTGCCGTACACCAACCCCTCCAAGTTT
AATCAGTACATCGTGTGTCTGGCCCATCACGTCATAGCCATGTGGTTCATCAGGTGCCGCCTGCCCTTCCGG
AAGGATTTTGTCCCTTTCATCACTAAGGGCCTGCGGTCCAATGTCCTCTTGTCTTTTGATGACACCCCCGAG
AAGGACAGCTTCAGGGCCCGGAGTACTAGTCTCAACGAGAGACCCAAGAGTCTGAGGATAGCCAGACCCCCC
AAACAAGGCTTGAATAACTCTCCACCCGTGAAAGAATTCAAGGAGAGCTCTGCAGCCGAGGCCTTCCGGTGC
CGCAGCATCAGTGTGTCTGAACATGTGGTCCGCAGCAGGATACAGACGTCCCTCACCAGTGCCAGCTTGGGG
TCTGCAGATGAGAACTCCGTGGCCCAGGCTGACGATAGCCTGAAAAACCTCCACCTGGAGCTCACGGAAACC
TGTCTGGACATGATGGCTCGATACGTCTTCTCCAACTTCACGGCTGTCCCGAAGAGGTCTCCTGTGGGCGAG
TTCCTCCTAGCGGGTGGCAGGACCAAAACCTGGCTGGTTGGGAACAAGCTTGTCACTGTGACGACAAGCGTG
```

TABLE 14-continued

TSC2 variant 1 (lacking exon 19) Nucleotide Sequence
(5301 nt, SEQ ID No. 34)

```
GGAACCGGGACCCGGTCGTTACTAGGCCTGGACTCGGGGGAGCTGCAGTCCGGCCCGGAGTCGAGCTCCAGC
CCCGGGGTGCATGTGAGACAGACCAAGGAGGCGCCGGCCAAGCTGGAGTCCCAGGCTGGGCAGCAGGTGTCC
CGTGGGGCCCGGGATCGGGTCCGTTCCATGTCGGGGGGCCATGGTCTTCGAGTTGGCGCCCTGGACGTGCCG
GCCTCCCAGTTCCTGGGCAGTGCCACTTCTCCAGGACCACGGACTGCACCAGCCGCGAAACCTGAGAAGGCC
TCAGCTGGCACCCGGGTTCCTGTGCAGGAGAAGACGAACCTGGCGGCCTATGTGCCCCTGCTGACCCAGGGC
TGGGCGGAGATCCTGGTCCGGAGGCCCACAGGGAACACCAGCTGGCTGATGAGCCTGGAGAACCCGCTCAGC
CCTTTCTCCTCGGACATCAACAACATGCCCCTGCAGGAGCTGTCTAACGCCCTCATGGCGGCTGAGCGCTTC
AAGGAGCACCGGGACACAGCCCTGTACAAGTCACTGTCGGTGCCGGCAGCCAGCACGGCCAAACCCCCTCCT
CTGCCTCGCTCCAACACAGTGGCCTCTTTCTCCTCCCTGTACCAGTCCAGCTGCCAAGGACAGCTGCACAGG
AGCGTTTCCTGGGCAGACTCCGCCGTGGTCATGGAGGAGGGAAGTCCGGGCGAGGTTCCTGTGCTGGTGGAG
CCCCCAGGGTTGGAGGACGTTGAGGCAGCGCTAGGCATGGACAGGCGCACGGATGCCTACAGCAGGTCGTCC
TCAGTCTCCAGCCAGGAGGAGAAGTCGCTCCACGCGGAGGAGCTGGTTGGCAGGGGCATCCCCATCGAGCGA
GTCGTCTCCTCGGAGGGTGGCCGGCCCTCTGTGGACCTCTCCTTCCAGCCCTCGCAGCCCCTGAGCAAGTCC
AGCTCCTCTCCCGAGCTGCAGACTCTGCAGGACATCCTCGGGGACCCTGGGGACAAGGCCGACGTGGGCCGG
CTGAGCCCTGAGGTTAAGGCCCGGTCACAGTCAGGGACCCTGGACGGGGAAAGTGCTGCCTGGTCGGCCTCG
GGCGAAGACAGTCGGGGCCAGCCCGAGGGTCCCTTGCCTTCCAGCTCCCCCGCTCGCCCAGTGGCCTCCGG
CCCCGAGGTTACACCATCTCCGACTCGGCCCCATCACGCAGGGGCAAGAGAGTAGAGAGGGACGCCTTAAAG
AGCAGAGCCACAGCCTCCAATGCAGAGAAAGTGCCAGGCATCAACCCCAGTTTCGTGTTCCTGCAGCTCTAC
CATTCCCCCTTCTTTGGCGACGAGTCAAACAAGCCAATCCTGCTGCCCAATGAGTCACAGTCCTTTGAGCGG
TCGGTGCAGCTCCTCGACCAGATCCCATCATACGACACCCACAAGATCGCCGTCCTGTATGTTGGAGAAGGC
CAGAGCAACAGCGAGCTCGCCATCCTGTCCAATGAGCATGGCTCCTACAGGTACACGGAGTTCCTGACGGGC
CTGGGCCGGCTCATCGAGCTGAAGGACTGCCAGCCGGACAAGGTGTACCTGGGAGGCCTGGACGTGTGTGGT
GAGGACGGCCAGTTCACCTACTGCTGGCACGATGACATCATGCAAGCCGTCTTCCACATCGCCACCCTGATG
CCCACCAAGGACGTGGACAAGCACCGCTGCGACAAGAAGCGCCACCTGGGCAACGACTTTGTGTCCATTGTC
TACAATGACTCCGGTGAGGACTTCAAGCTTGGCACCATCAAGGGCCAGTTCAACTTTGTCCACGTGATCGTC
ACCCCGCTGGACTACGAGTGCAACCTGGTGTCCCTGCAGTGCAGGAAAGACATGGAGGGCCTTGTGGACACC
AGCGTGGCCAAGATCGTGTCTGACCGCAACCTGCCCTTCGTGGCCCGCCAGATGGCCCTGCACGCAAATATG
GCCTCACAGGTGCATCATAGCCGCTCCAACCCCACCGATATCTACCCCTCCAAGTGGATTGCCCGGCTCCGC
CACATCAAGCGGCTCCGCCAGCGGATCTGCGAGGAAGCCGCCTACTCCAACCCCAGCCTACCTCTGGTGCAC
CCTCCGTCCCATAGCAAAGCCCCTGCACAGACTCCAGCCGAGCCCACACCTGGCTATGAGGTGGGCCAGCGG
AAGCGCCTCATCTCCTCGGTGGAGGACTTCACCGAGTTTGTGTGA
```

(Double underline indicates bases bordering the splice junction)

TABLE 15

Primer across the junction between TSC2 exon 18 and 20

Table 23. Primer sequences across the junction between TSC2 exon 18 and 20 (SEQ ID No. 33)    CTTGAAGCA<u><u>GC</u></u>TTTCAGGCC (Double underline indicates bases bordering the splice junction)

TABLE 16 siRNA for selectively knockdown TSC2 full length and variant expression siRNA targeting TSC2 exon 19

Sense (SEQ ID No. 31) 5' CUGCGCUAUAAAGUGCUCAdTdT 3'

TABLE 16-continued siRNA for selectively knockdown TSC2 full length and variant expression Antisense (SEQ ID No. 32) 3' dTdTGACGCGAUAUUUCACGAGU (5'-P)5' siRNA targeting the junction between TSC2 exon 18 and exon 20

Sense (SEQ ID No. 35) 5' GAAGCA<u>GC</u>UUUCAGGCCCAdTdT 3'

Antisense (SEQ ID No. 36) 3' dTdTCUUCGU<u>CG</u>AAAGUCCGGGU (5'-P)5'

(Double underline indicates bases bordering the splice junction)

TABLE 17

RASGRP2 (full length) Nucleotide Sequence (1830 nt, SEQ ID No. 37)

ATGGCAGGCACCCTGGACCTGGACAAGGGCTGCACGGTGGAGGAGCTGCTCCGCGGGTGCATCGAAGCCTTC

GATGACTCCGGGAAGGTGCGGGACCCGCAGCTGGTGCGCATGTTCCTCATGATGCACCCCTGGTACATCCCC

TCCTCTCAGCTGGCGGCCAAGCTGCTCCACATCTACCAACAATCCCGGAAGGACAACTCCAATTCCCTGCAG

GTGAAAACGTGCCACCTGGTCAGGTACTGGATCTCCGCCTTCCCAGCGGAGTTTGACTTGAACCCGGAGTTG

GCTGAGCAGATCAAGGAGCTGAAGGCTCTGCTAGACCAAGAAGGGAACCGACGGCACAGCAGCCTAATCGAC

ATAGACAGCGTCCCTACCTACAAGTGGAAGCGGCAGGTGACTCAGCGGAACCCTGTGGGACAGAAAAAGCGC

AAGATGTCCCTGTTGTTTGACCACCTGGAGCCCATGGAGCTGGCGGAGCATCTCACCTACTTGGAGTATCGC

TCCTTCTGCAAGATCCTGTTTCAGGACTATCACAGTTTCGTGACTCATGGCTGCACTGTGGACAACCCCGTC

CTGGAGCGGTTCATCTCCCTCTTCAACAGCGTCTCACAGTGGGTGCAGCTCATGATCCTCAGCAAACCCACA

GCCCCGCAGCGGGCCCTGGTCATCACACACTTTGTCCACGTGGCGGAGAAGCTGCTACAGCTGCAGAACTTC

AACACGCTGATGGCAGTGGTCGGGGGCCTGAGCCACAGCTCCATCTCCCGCCTCAAGGAGACCCACAGCCAC

GTTAGCCCTGAGACCATCAAGCTCTGGGAGGGTCTCACGGAACTAGTGACGGCGACAGGCAACTATGGCAAC

TACCGGCGTCGGCTGGCAGCCTGTGTGGGCTTCCGCTTCCCGATCCTGGGTGTGCACCTCAAGGACCTGGTG

GCCCTGCAGCTGGCACTGCCTGACTGGCTGGACCCAGCCCGGACCCGGCTCAACGGGGCCAAGATGAAGCAG

CTCTTTAGCATCCTGGAGGAGCTGGCCATGGTGACCAGCCTGCGGCCACCAGTACAGGCCAACCCCGACCTG

CTGAGCCTGC<u>TCACGGTGTCTCTGGATCAGT</u>ATCAGACGGAGGATGAGCTGTACCAGCTGTCCCTGCAGCGG

GAGCCGCGCTCCAAGTCCTCGC<u>CAACCAGCCCCACGAGTTGCACCCCACCACCCCGGCCCCGGTACTGGAG

GAGTGGACCTCGGCTGCCAAACCCAAGCTGGATCAGGCCCTCGTGGTGGAGCACATCGAGAAGATGGTGGAG</u>

TCTGTGTTCCGGAACTTTGACGTCGATGGGGATGGCCACATCTCACAGGAAGAATTCCAGATCATCCGTGGG

AACTTCCCTTACCTCAGCGCCTTTGGGGACCTCGACCAGAACCAGGATGGCTGCATCAGCAGGGAGGAGATG

GTTTCCTATTTCCTGCGCTCCAGCTCTGTGTTGGGGGGGCGCATGGGCTTCGTACACAACTTCCAGGAGAGC

AACTCCTTGCGCCCCGTCGCCTGCCGCCACTGCAAAGCCCTGATCCTGGGCATCTACAAGCAGGGCCTCAAA

TGCCGAGCCTGTGGAGTGAACTGCCACAAGCAGTGCAAGGATCGCCTGTCAGTTGAGTGTCGGCGCAGGGCC

TABLE 17-continued

RASGRP2 (full length) Nucleotide Sequence (1830 nt, SEQ ID No. 37)

CAGAGTGTGAGCCTGGAGGGGTCTGCACCCTCACCCTCACCCATGCACAGCCACCATCACCGCGCCTTCAGC

TTCTCTCTGCCCCGCCCTGGCAGGCGAGGCTCCAGGCCTCCAGAGATCCGTGAGGAGGAGGTACAGACGGTG

GAGGATGGGGTGTTTGACATCCACTTGTAA (Exon 10 is indicated by double underline. Exon 11 is indicated by wave underline.)

TABLE 18

RASGRP2 variant 1 (lacking exon 10) Nucleotide Sequence (1707 nt, SEQ ID No. 45)

ATGGCAGGCACCCTGGACCTGGACAAGGGCTGCACGGTGGAGGAGCTGCT

CCGCGGGTGCATCGAAGCCTTCGATGACTCCGGGAAGGTGCGGGACCCGC

AGCTGGTGCGCATGTTCCTCATGATGCACCCCTGGTACATCCCCTCCTCT

CAGCTGGCGGCCAAGCTGCTCCACATCTACCAACAATCCCGGAAGGACAA

CTCCAATTCCCTGCAGGTGAAAACGTGCCACCTGGTCAGGTACTGGATCT

CCGCCTTCCCAGCGGAGTTTGACTTGAACCCGGAGTTGGCTGAGCAGATC

AAGGAGCTGAAGGCTCTGCTAGACCAAGAAGGGAACCGACGGCACAGCAG

CCTAATCGACATAGACAGCGTCCCTACCTACAAGTGGAAGCGGCAGGTGA

CTCAGCGGAACCCTGTGGGACAGAAAAAGCGCAAGATGTCCCTGTTGTTT

GACCACCTGGAGCCCATGGAGCTGGCGGAGCATCTCACCTACTTGGAGTA

TCGCTCCTTCTGCAAGATCCTGTTTCAGGACTATCACAGTTTCGTGACTC

ATGGCTGCACTGTGGACAACCCCGTCCTGGAGCGGTTCATCTCCCTCTTC

AACAGCGTCTCACAGTGGGTGCAGCTCATGATCCTCAGCAAACCCACAGC

CCCGCAGCGGGCCCTGGTCATCACACACTTTGTCCACGTGGCGGAGAAGC

TGCTACAGCTGCAGAACTTCAACACGCTGATGGCAGTGGTCGGGGGCCTG

AGCCACAGCTCCATCTCCCGCCTCAAGGAGACCCACAGCCACGTTAGCCC

TGAGACCATCAAGCTCTGGGAGGGTCTCACGGAACTAGTGACGGCGACAG

GCAACTATGGCAACTACCGGCGTCGGCTGGCAGCCTGTGTGGGCTTCCGC

TTCCCGATCCTGGGTGTGCACCTCAAGGACCTGGTGGCCCTGCAGCTGGC

ACTGCCTGACTGGCTGGACCCAGCCCGGACCCGGCTCAACGGGGCCAAGA

TGAAGCAGCTCTTTAGCATCCTGGAGGAGCTGGCCATGGTGACCAGCCTG

CGGCCACCAGTACAGGCCAACCCCGACCTGCTGAGCCTGCTCACGGTGTC

TCTGGATCAGTATCAGACGGAGGATGAGCTGTACCAGCTGTCCCTGCAGC

GGGAGCCGCGCTCCAAGTCCTCGTCTGTGTTCCGGAACTTTGACGTCGAT

GGGGATGGCCACATCTCACAGGAAGAATTCCAGATCATCCGTGGGAACTT

CCCTTACCTCAGCGCCTTTGGGGACCTCGACCAGAACCAGGATGGCTGCA

TCAGCAGGGAGGAGATGGTTTCCTATTTCCTGCGCGCTCCAGCTCTGTGTTG

GGGGGGCGCATGGGCTTCGTACACAACTTCCAGGAGAGCAACTCCTTGCG

CCCCGTCGCCTGCCGCCACTGCAAAGCCCTGATCCTGGGCATCTACAAGC

AGGGCCTCAAATGCCGAGCCTGTGGAGTGAACTGCCACAAGCAGTGCAAG

GATCGCCTGTCAGTTGAGTGTCGGCGCAGGGCCCAGAGTGTGAGCCTGGA

GGGGTCTGCACCCTCACCCTCACCCATGCACAGCCACCATCACCGCGCCT

TCAGCTTCTCTCTGCCCCGCCCTGGCAGGCGAGGCTCCAGGCCTCCAGAG

ATCCGTGAGGAGGAGGTACAGACGGTGGAGGATGGGGTGTTTGACATCCA

CTTGTAA (Double underline indicates bases bordering the splice junction)

TABLE 19

RASGRP2 variant 2 (lacking exon 11) Nucleotide Sequence (1714 nt, SEQ ID No. 49)

ATGGCAGGCACCCTGGACCTGGACAAGGGCTGCACGGTGGAGGAGCTGCT

CCGCGGGTGCATCGAAGCCTTCGATGACTCCGGGAAGGTGCGGGACCCGC

AGCTGGTGCGCATGTTCCTCATGATGCACCCCTGGTACATCCCCTCCTCT

CAGCTGGCGGCCAAGCTGCTCCACATCTACCAACAATCCCGGAAGGACAA

CTCCAATTCCCTGCAGGTGAAAACGTGCCACCTGGTCAGGTACTGGATCT

CCGCCTTCCCAGCGGAGTTTGACTTGAACCCGGAGTTGGCTGAGCAGATC

AAGGAGCTGAAGGCTCTGCTAGACCAAGAAGGGAACCGACGGCACAGCAG

CCTAATCGACATAGACAGCGTCCCTACCTACAAGTGGAAGCGGCAGGTGA

CTCAGCGGAACCCTGTGGGACAGAAAAAGCGCAAGATGTCCCTGTTGTTT

GACCACCTGGAGCCCATGGAGCTGGCGGAGCATCTCACCTACTTGGAGTA

TCGCTCCTTCTGCAAGATCCTGTTTCAGGACTATCACAGTTTCGTGACTC

ATGGCTGCACTGTGGACAACCCCGTCCTGGAGCGGTTCATCTCCCTCTTC

AACAGCGTCTCACAGTGGGTGCAGCTCATGATCCTCAGCAAACCCACAGC

CCCGCAGCGGGCCCTGGTCATCACACACTTTGTCCACGTGGCGGAGAAGC

TGCTACAGCTGCAGAACTTCAACACGCTGATGGCAGTGGTCGGGGGCCTG

AGCCACAGCTCCATCTCCCGCCTCAAGGAGACCCACAGCCACGTTAGCCC

TGAGACCATCAAGCTCTGGGAGGGTCTCACGGAACTAGTGACGGCGACAG

GCAACTATGGCAACTACCGGCGTCGGCTGGCAGCCTGTGTGGGCTTCCGC

TTCCCGATCCTGGGTGTGCACCTCAAGGACCTGGTGGCCCTGCAGCTGGC

ACTGCCTGACTGGCTGGACCCAGCCCGGACCCGGCTCAACGGGGCCAAGA

TGAAGCAGCTCTTTAGCATCCTGGAGGAGCTGGCCATGGTGACCAGCCTG

CGGCCACCAGTACAGGCCAACCCCGACCTGCTGAGCCTGCTCACGGTGTC

TCTGGATCAGTATCAGACGGAGGATGAGCTGTACCAGCTGTCCCTGCAGC

TABLE 19-continued

RASGRP2 variant 2 (lacking exon 11) Nucleotide Sequence (1714 nt, SEQ ID No. 49)

GGGAGCCGCGCTCCAAGTCCTCGCCAACCAGCCCCACGAGTTGCACCCCA

CCACCCCGGCCCCCGGTACTGGAGGAGTGGACCTCGGCTGCCAAACCCAA

GCTGGATCAGGCCCTCGTGGTGGAGCACATCGAGAA<u>GATGGTGGAGGGAT</u>

<u>GGCTGC</u>ATCAGCAGGGAGGAGATGGTTTCCTATTTCCTGCGCTCCAGCTC

TGTGTTGGGGGGCGCATGGGCTTCGTACACAACTTCCAGGAGAGCAACT

CCTTGCGCCCCGTCGCCTGCCGCCACTGCAAAGCCCTGATCCTGGGCATC

TACAAGCAGGGCCTCAAATGCCGAGCCTGTGGAGTGAACTGCCACAAGCA

GTGCAAGGATCGCCTGTCAGTTGAGTGTCGGCGCAGGGCCCAGAGTGTGA

GCCTGGAGGGGTCTGCACCCTCACCCTCACCCATGCACAGCCACCATCAC

CGCGCCTTCAGCTTCTCTCTGCCCCGCCCTGGCAGGCGAGGCTCCAGGCC

TCCAGAGATCCGTGAGGAGGAGGTACAGACGGTGGAGGATGGGGTGTTTG

ACATCCACTTGTAA (Double underline indicates bases bordering the splice junction)

TABLE 20

Primer across the junction between RASGRP2 variants

| Primer across junction between RASGRP2 exon 9 and exon 11 (SEQ ID No. 44) | CAAGTCCTCG<u>GT</u>CTGTGTTCC |
| --- | --- |
| Primer across junction between RASGRP2 exon 10 and exon 12 (SEQ ID No. 48) | <u>GATGGTGGAGGGATGGCTGC</u> |

(Double underline indicates bases bordering the splice junction)

TABLE 21 siRNA for selectively knockdown RASGRP2 full length and variants expression siRNA targeting RASGRP2 exon 10

Sense (SEQ ID No. 40): 5' GUGGAGCACAUCGAGAAGAdTdT 3'

Antisense (SEQ ID No. 41): 3' dTdTCACCUCGUGUAGCUC-UUCU (5'-P)5' siRNA targeting RASGRP2 exon 11

Sense (SEQ ID No. 42): 5' CCACAUCUCACAGGAAGAAdTdT 3'

Antisense (SEQ ID No. 43): 3' dTdGGUGUAGAGUGUCCU-UCUU (5'-P)5 siRNA targeting junction between RASGRP2 exon 9 and 11:

Sense (SEQ ID No. 46): 5' CCUC<u>GU</u>CUGUGUUCCGGAAdTdT 3'

TABLE 21-continued siRNA for selectively knockdown RASGRP2 full length and variants expression

Antisense (SEQ ID No. 47): 3' dTdTGGAGC<u>CA</u>GACACAAGG-CCUU (5'-P)5' siRNA targeting junction between RASGRP2 exon 10 and 12

Sense (SEQ ID No. 50): 5' GGUGGA<u>GG</u>GAUGGCUGCAUdTdT 3'

Antisense (SEQ ID No. 51): 3' dTdTCCACCU<u>CC</u>CUACCGA-CGUA (5'-P)5'

(Double underline indicates bases bordering the splice junction)

TABLE 22

ITGA4 (full length) Nucleotide Sequence (3099 nt, SEQ ID No. 52)

ATGGCTTGGGAAGCGAGGCGCGAACCCGGCCCCCGAAGGGCCGCCGTCCG

GGAGACGGTGATGCTGTTGCTGTGCCTGGGGGTCCCGACCGGCCGCCCCT

ACAACGTGGACACTGAGAGCGCGCTGCTTTACCAGGGCCCCCACAACACG

CTGTTCGGCTACTCGGTCGTGCTGCACAGCCACGGGGCGAACCGATGGCT

CCTAGTGGGTGCGCCCACTGCCAACTGGCTCGCCAACGCTTCAGTGATCA

ATCCCGGGGCGATTTACAGATGCAGGATCGGAAAGAATCCCGGCCAGACG

TGCGAACAGCTCCAGCTGGGTAGCCCTAATGGAGAACCTTGTGGAAAGAC

TTGTTTGGAAGAGAGAGACAATCAGTGGTTGGGGGTCACACTTTCCAGAC

AGCCAGGAGAAAATGGATCCATCGTGACTTGTGGGCATAGATGGAAAAAT

ATATTTTACATAAAGAATGAAAATAAGCTCCCCACTGGTGGTTGCTATGG

AGTGCCCCCTGATTTACGAACAGAACTGAGTAAAAGAATAGCTCCGTGTT

ATCAAGATTATGTGAAAAAATTTGGAGAAAATTTTGCATCATGTCAAGCT

GGAATATCCAGTTTTTACACAAAGGATTTAATTGTGATGGGGCCCCAGG

ATCATCTTACTGGACTGGCTCTCTTTTTGTCTACAATATAACTACAAATA

AATACAAGGCTTTTTTAGACAAACAAAATCAAGTAAAATTTGGAAGTTAT

TTAGGATATTCAGTCGGAGCTGGTCATTTTCGGAGCCAGCATACTACCGA

AGTAGTCGGAGGAGCTCCTCAACATGAGCAGATTGGTAAGGCATATATAT

TCAGCATTGATGAAAAAGAACTAAATATCTTACATGAAATGAAAGGTAAA

AAGCTTGGATCGTACTTTGGAGCTTCTGTCTGTGCTGTGGACCTCAATGC

AGATGGCTTCTCAGATCTGCTCGTGGGAGCACCCATGCAGAGCACCATCA

GAGAGGAAGGAAGAGTGTTTGTGTACATCAACTCTGGCTCGGGAGCAGTA

ATGAATGCAATGGAAACAAACCTCGTTGGAAGTGACAAATATGCTGCAAG

ATTTGGGGAATCTATAGTTAATCTTGGCGACATTGACAATGATGGCTTTG

AAGATGTTGCTATCGGAGCTCCACAAGAAGATGACTTGCAAGGTGCTATT

TATATTTACAATGGCCGTGCAGATGGGATCTCGTCAACCTTCTCACAGAG

AATTGAAGGACTTCAGATCAGCAAATCGTTAAGTATGTTTGGACAGTCTA

TATCAGGACAAATTGATGCAGATAATAATGGCTATGTAGATGTAGCAGTT

GGTGCTTTTCGGTCTGATTCTGCTGTCTTGCTAAGGACAAGACCTGTAGT

TABLE 22-continued

ITGA4 (full length) Nucleotide Sequence
(3099 nt, SEQ ID No. 52)

AATTGTTGACGCTTCTTTAAGCCACCCTGAGTCAGTAAATAGAACGAAAT

TTGACTGTGTTGAAAATGGATGGCCTTCTGTGTGCATAGATCTAACACTT

TGTTTCTCATATAAGGGCAAGGAAGTTCCAGGTTACATTGTTTTGTTTTA

TAACATGAGTTTGGATGTGAACAGAAAGGCAGAGTCTCCACCAAGATTCT

ATTTCTCTTCTAATGGAACTTCTGACGTGATTACAGGAAGCATACAGGTG

TCCAGCAGAGAAGCTAACTGTAGAACACATCAAGCATTTATGCGGAAAGA

TGTGCGGGACATCCTCACCCCAATTCAGATTGAAGCTGCTTACCACCTTG

GTCCTCATGTCATCAGTAAACGAAGTACAGAGGAATTCCCACCACTTCAG

CCAATTCTTCAGCAGAAGAAAGAAAAAGACATAATGAAAAAACAATAAA

CTTTGCAAGGTTTTGTGCCCATGAAAATTGTTCTGCTGATTTACAGGTTT

CTGCAAAGATTGGGTTTTTGAAGCCCCATGAAAATAAAACATATCTTGCT

GTTGGGAGTATGAAGACATTGATGTTGAATGTGTCCTTGTTTAATGCTGG

AGATGATGCATATGAAACGACTCTACATGTCAAACTACCCGTGGGTCTTT

ATTTCATTAAGATTTTAGAGCTGGAAGAGAAGCAAATAAACTGTGAAGTC

ACAGATAACTCTGGCGTGGTACAACTTGACTGCAGTATTGGCTATATATA

TGTAGATCATCTCTCAAGGATAGATATTAGCTTTCTCCTGGATGTGAGCT

CACTCAGCAGAGCGGAAGAGGACCTCAGTATCACAGTGCATGCTACCTGT

GAAAATGAAGAGGAAATGGACAATCTAAAGCACAGCAGAGTGACTGTAGC

AATACCTTTAAAATATGAGGTTAAGCTGACTGTTCATGGGTTTGTAAACC

CAACTTCATTTGTGTATGGATCAAATGATGAAAATGAGCCTGAAACGTGC

ATGGTGGAGAAAATGAACTTAACTTTCCATGTTATCAACACTGGCAATAG

TATGGCTCCCAATGTTAGTGTGGAAATAATGGTACCAAATTCTTTTAGCC

CCCAAACTGATAAGCTGTTCAACATTTTGGATGTCCAGACTACTACTGGA

GAATGCCACTTTGAAAATTATCAAAGAGTGTGTGCATTAGAGCAGCAAAA

GAGTGCAATGCAGACCTTGAAAGGCATAGTCCGGTTCTTGTCCAAGACTG

ATAAGAGGCTATTGTACTGCATAAAAGCTGATCCACATTGTTTAAATTTC

TTGTGTAATTTTGGGAAAATGGAAAGTGGAAAAGAAGCCAGTGTTCATAT

CCAACTGGAAGGCCGGCCATCCATTTTAGAAATGGATGAGACTTCAGCAC

TCAAGTTTGAAATAAGAGCAACAGGTTTTCCAGAGCCAAATCCAAGAGTA

ATTGAACTAAACAAGGATGAGAATGTTGCGCATGTTCTACTGGAAGGACT

ACATCATCAAAGACCCAAACGTTATTTCACCATAGTGATTATTTCAAGTA

GCTTGCTACTTGGACTTATTGTACTTCTATTGATCTCATATGTTATGTGG

AAGGCTGGCTTCTTAAAAGACAATACAAATCTATCCTACAAGAAGAAAA

CAGAAGAGACAGTTGGAGTTATATCAACAGTAAAAGCAATGATGATTAA (Exon 23 is indicated by double underline.)

TABLE 23

ITGA4 variant (lacking exon 23) Nucleotide
Sequence (2948 nt, SEQ ID No. 58)

ATGGCTTGGGAAGCGAGGCGCGAACCCGGCCCCCGAAGGGCCGCCGTCCG

GGAGACGGTGATGCTGTTGCTGTGCCTGGGGGTCCCGACCGGCCGCCCCT

ACAACGTGGACACTGAGAGCGCGCTGCTTTACCAGGGCCCCCACAACACG

CTGTTCGGCTACTCGGTCGTGCTGCACAGCCACGGGGCGAACCGATGGCT

CCTAGTGGGTGCGCCCACTGCCAACTGGCTCGCCAACGCTTCAGTGATCA

ATCCCGGGGCGATTTACAGATGCAGGATCGGAAAGAATCCCGGCCAGACG

TGCGAACAGCTCCAGCTGGGTAGCCCTAATGGAGAACCTTGTGGAAAGAC

TTGTTTGGAAGAGAGAGACAATCAGTGGTTGGGGGTCACACTTTCCAGAC

AGCCAGGAGAAAATGGATCCATCGTGACTTGTGGGCATAGATGGAAAAAT

ATATTTTACATAAAGAATGAAAATAAGCTCCCCACTGGTGGTTGCTATGG

AGTGCCCCCTGATTTACGAACAGAACTGAGTAAAAGAATAGCTCCGTGTT

ATCAAGATTATGTGAAAAAATTTGGAGAAAATTTTGCATCATGTCAAGCT

GGAATATCCAGTTTTTACACAAAGGATTTAATTGTGATGGGGCCCCAGG

ATCATCTTACTGGACTGGCTCTCTTTTTGTCTACAATATAACTACAAATA

AATACAAGGCTTTTTTAGACAAACAAAATCAAGTAAAATTTGGAAGTTAT

TTAGGATATTCAGTCGGAGCTGGTCATTTTCGGAGCCAGCATACTACCGA

AGTAGTCGGAGGAGCTCCTCAACATGAGCAGATTGGTAAGGCATATATAT

TCAGCATTGATGAAAAAGAACTAAATATCTTACATGAAATGAAAGGTAAA

AAGCTTGGATCGTACTTTGGAGCTTCTGTCTGTGCTGTGGACCTCAATGC

AGATGGCTTCTCAGATCTGCTCGTGGGAGCACCCATGCAGAGCACCATCA

GAGAGGAAGGAAGAGTGTTTGTACATCAACTCTGGCTCGGGAGCAGTA

ATGAATGCAATGGAAACAAACCTCGTTGGAAGTGACAAATATGCTGCAAG

ATTTGGGGAATCTATAGTTAATCTTGCGACATTGACAATGATGGCTTTG

AAGATGTTGCTATCGGAGCTCCACAAGAAGATGACTTGCAAGGTGCTATT

TATATTTACAATGGCCGTGCAGATGGGATCTCGTCAACCTTCTCACAGAG

AATTGAAGGACTTCAGATCAGCAAATCGTTAAGTATGTTTGGACAGTCTA

TATCAGGACAAATTGATGCAGATAATAATGGCTATGTAGATGTAGCAGTT

GGTGCTTTTCGGTCTGATTCTGCTGTCTTGCTAAGGACAAGACCTGTAGT

AATTGTTGACGCTTCTTTAAGCCACCCTGAGTCAGTAAATAGAACGAAAT

TTGACTGTGTTGAAAATGGATGGCCTTCTGTGTGCATAGATCTAACACTT

TGTTTCTCATATAAGGGCAAGGAAGTTCCAGGTTACATTGTTTTGTTTTA

TAACATGAGTTTGGATGTGAACAGAAAGGCAGAGTCTCCACCAAGATTCT

ATTTCTCTTCTAATGGAACTTCTGACGTGATTACAGGAAGCATACAGGTG

TCCAGCAGAGAAGCTAACTGTAGAACACATCAAGCATTTATGCGGAAAGA

TGTGCGGGACATCCTCACCCCAATTCAGATTGAAGCTGCTTACCACCTTG

GTCCTCATGTCATCAGTAAACGAAGTACAGAGGAATTCCCACCACTTCAG

CCAATTCTTCAGCAGAAGAAAGAAAAAGACATAATGAAAAAACAATAAA

CTTTGCAAGGTTTTGTGCCCATGAAAATTGTTCTGCTGATTTACAGGTTT

CTGCAAAGATTGGGTTTTTGAAGAAGAGAAGCAAATAAACTGTGAAGTCA

TABLE 23-continued

ITGA4 variant (lacking exon 23) Nucleotide Sequence (2948 nt, SEQ ID No. 58)

CAGATAACTCTGGCGTGGTACAACTTGACTGCAGTATTGGCTATATATAT

GTAGATCATCTCTCAAGGATAGATATTAGCTTTCTCCTGGATGTGAGCTC

ACTCAGCAGAGCGGAAGAGGACCTCAGTATCACAGTGCATGCTACCTGTG

AAAATGAAGAGGAAATGGACAATCTAAAGCACAGCAGAGTGACTGTAGCA

ATACCTTTAAAATATGAGGTTAAGCTGACTGTTCATGGGTTTGTAAACCC

AACTTCATTTGTGTATGGATCAAATGATGAAAATGAGCCTGAAACGTGCA

TGGTGGAGAAAATGAACTTAACTTTCCATGTTATCAACACTGGCAATAGT

ATGGCTCCCAATGTTAGTGTGGAAATAATGGTACCAAATTCTTTTAGCCC

CCAAACTGATAAGCTGTTCAACATTTTGGATGTCCAGACTACTACTGGAG

AATGCCACTTTGAAAATTATCAAAGAGTGTGTGCATTAGAGCAGCAAAAG

AGTGCAATGCAGACCTTGAAAGGCATAGTCCGGTTCTTGTCCAAGACTGA

TAAGAGGCTATTGTACTGCATAAAAGCTGATCCACATTGTTTAAATTTCT

TGTGTAATTTTGGGAAAATGGAAAGTGGAAAAGAAGCCAGTGTTCATATC

CAACTGGAAGGCCGGCCATCCATTTTAGAAATGGATGAGACTTCAGCACT

CAAGTTTGAAATAAGAGCAACAGGTTTTCCAGAGCCAAATCCAAGAGTAA

TTGAACTAAACAAGGATGAGAATGTTGCGCATGTTCTACTGGAAGGACTA

CATCATCAAAGACCCAAACGTTATTTCACCATAGTGATTATTTCAAGTAG

CTTGCTACTTGGACTTATTGTACTTCTATTGATCTCATATGTTATGTGGA

TABLE 23-continued

ITGA4 variant (lacking exon 23) Nucleotide Sequence (2948 nt, SEQ ID No. 58)

AGGCTGGCTTCTTTAAAAGACAATACAAATCTATCCTACAAGAAGAAAAC

AGAAGAGACAGTTGGAGTTATATCAACAGTAAAAGCAATGATGATTAA (Double underline indicates bases bordering the splice junction)

TABLE 24

Primer across the junction between ITGA4 exon 22 and 24

| Primer across the junction between ITGA4 exon 22 and 24 (SEQ ID No. 57) | GGGTTTTTGAAGAAGAGAAGC |
|---|---|

(Double underline indicates bases bordering the splice junction)

TABLE 25 siRNA for selectively knockdown ITGA4 full length and variants expression siRNA targeting ITGA4 exon 23

Sense (SEQ ID No. 55) 5' GGGAGUAUGAAGACAUUGA dTdT 3'

Antisense (SEQ ID No. 56) 3' dTdTCCCUCAUACUUCUGUA-ACU (5'-P)5' siRNA targeting splice junction between ITGA4 exon 22 and exon 24

Sense (SEQ ID No. 59) 5' GAAGAAGAGAAGCAAAUAA dTdT 3'

Antisense (SEQ ID No. 60) 3' dTdTCUUCUUCUCUUCGUUU-AUU (5'-P)5'

(Double underline indicates bases bordering the splice junction)

TABLE 26

MET (Full length) Nucleotide Sequence (4226 nt, SEQ ID No. 62)

ATGAAGGCCCCCGCTGTGCTTGCACCTGGCATCCTCGTGCTCCTGTTTACCTTGGTGCAGAGGAGCAATGGG

AGTGTAAAGAGGCACTAGCAAAGTCCGAGATGAATGTGAATATGAAGTATCAGCTTCCCAACTTCACCGCGG

AAACACCCATCCAGAATGTCATTCTACATGAGCATCACATTTTCCTTGGTGCCACTAACTACATTTATGTTT

TAAATGAGGAAGACCTTCAGAAGGTTGCTGAGTACAAGACTGGGCCTGTGCTGGAACACCCAGATTGTTTCC

CATGTCAGGACTGCAGCAGCAAAGCCAATTTATCAGGAGGTGTTTGGAAAGATAACATCAACATGGCTCTAG

TTGTCGACACCTACTATGATGATCAACTCATTAGCTGTGGCAGCGTCAACAGAGGGACCTGCCAGCGACATG

TCTTTCCCCACAATCATACTGCTGACATACAGTCGGAGGTTCACTGCATATTCTCCCCACAGATAGAAGAGC

CCAGCCAGTGTCCTGACTGTGTGGTGAGCGCCCTGGGAGCCAAAGTCCTTTCATCTGTAAAGGACCGGTTCA

TCAACTTCTTTGTAGGCAATACCATAAATTCTTCTTATTTCCCAGATCATCCATTGCATTCGATATCAGTGA

GAAGGCTAAAGGAAACGAAAGATGGTTTTATGTTTTGACGGACCAGTCCTACATTGATGTTTTACCTGAGT

TCAGAGATTCTTACCCCATTAAGTATGTCCATGCCTTTGAAAGCAACAATTTTATTTACTTCTTGACGGTCC

AAAGGGAAACTCTAGATGCTCAGACTTTTCACACAAGAATAATCAGGTTCTGTTCCATAAACTCTGGATTGC

ATTCCTACATGGAAATGCCTCTGGAGTGTATTCTCACAGAAAAGAGAAAAAAGAGATCCACAAAGAAGGAAG

TABLE 26-continued

MET (Full length)Nucleotide Sequence (4226 nt, SEQ ID No. 62)

TGTTTAATATACTTCAGGCTGCGTATGTCAGCAAGCCTGGGGCCCAGCTTGCTAGACAAATAGGAGCCAGCC

TGAATGATGACATTCTTTTCGGGGTGTTCGCACAAAGCAAGCCAGATTCTGCCGAACCAATGGATCGATCTG

CCATGTGTGCATTCCCTATCAAATATGTCAACGACTTCTTCAACAAGATCGTCAACAAAAACAATGTGAGAT

GTCTCCAGCATTTTTACGGACCCAATCATGAGCACTGCTTTAATAGGACACTTCTGAGAAATTCATCAGGCT

GTGAAGCGCGCCGTGATGAATATCGAACAGAGTTTACCACAGCTTTGCAGCGCGTTGACTTATTCATGGGTC

AATTCAGCGAAGTCCTCTTAACATCTATATCCACCTTCATTAAAGGAGACCTCACCATAGCTAATCTTGGGA

CATCAGAGGGTCGCTTCATGCAGGTTGTGGTTTCTCGATCAGGACCATCAACCCCTCATGTGAATTTTCTCC

TGGACTCCCATCCAGTGTCTCCAGAAGTGATTGTGGAGCATACATTAAACCAAATGGCTACACACTGGTTA

TCACTGGGAAGAAGATCACGAAGATCCCATTGAATGGCTTGGGCTGCAGACATTTCCAGTCCTGCAGTCAAT

GCCTCTCTGCCCCACCCTTTGTTCAGTGTGGCTGGTGCCACGACAAATGTGTGCGATCGGAGGAATGCCTGA

GCGGGACATGGACTCAACAGATCTGTCTGCCTGCAATCTACAAGGTTTTCCCAAATAGTGCACCCCTTGAAG

GAGGGACAAGGCTGACCATATGTGGCTGGGACTTTGGATTTCGGAGGAATAATAAATTTGATTTAAAGAAAA

CTAGAGTTCTCCTTGGAAATGAGAGCTGCACCTTGACTTTAAGTGAGAGCACGATGAATACATTGAAATGCA

CAGTTGGTCCTGCCATGAATAAGCATTTCAATATGTCCATAATTATTTCAAATGGCCACGGGACAACACAAT

ACAGTACATTCTCCTATGTGGATCCTGTAATAACAAGTATTTCGCCGAAATACGGTCCTATGGCTGGTGGCA

CTTTACTTACTTTAACTGGAAATTACCTAAACAGTGGGAATTCTAGACACATTTCAATTGGTGGAAAAACAT

GTACTTTAAAAAGTGTGTCAAACAGTATTCTTGAATGTTATACCCCAGCCCAAACCATTTCAACTGAGTTTG

CTGTTAAATTGAAAATTGACTTAGCCAACCGAGAGACAAGCATCTTCAGTTACCGTGAAGATCCCATTGTCT

ATGAAATTCATCCAACCAAATCTTTTATTAGTACTTGGTGGAAAGAACCTCTCAACATTGTCAGTTTTCTAT

TTTGCTTTGCCAGTGGTGGGAGCACAATAACAGGTGTTGGGAAAAACCTGAATTCAGTTAGTGTCCCGAGAA

TGGTCATAAATGTGCATGAAGCAGGAAGGAACTTTACAGTGGCATGTCAACATCGCTCTAATTCAGAGATAA

TCTGTTGTACCACTCCTTCCCTGCAACAGCTGAATCTGCAACTCCCCCTGAAAACCAAAGCCTTTTTCATGT

TAGATGGGATCCTTTCCAAATACTTTGATCTCATTTATGTACATAATCCTGTGTTTAAGCCTTTTGAAAAGC

CAGTGATGATCTCAATGGGCAATGAAAATGTACTGGAAATTAAGGGAAATGATATTGACCCTGAAGCAGTTA

AAGGTGAAGTGTTAAAAGTTGGAAATAAGAGCTGTGAGAATATACACTTACATTCTGAAGCCGTTTTATGCA

CGGTCCCCAATGACCTGCTGAAATTGAACAGCGAGCTAAATATAGAGTGGAAGCAAGCAATTTCTTCAACCG

TCCTTGGAAAAGTAATAGTTCAACCAGATCAGAATTTCACAGGATTGATTGCTGGTGTTGTCTCAATATCAA

CAGCACTGTTATTACTACTTGGGTTTTTCCTGTGGCTGAAAAAGAGAAAGCAAATTAAAGATCTGGGCAGTG

AATTAGTTCGCTACGATGCAAGAGTACACACTCCTCATTTGGATAGGCTTGTAAGTGCCCGAAGTGTAAGCC

CAACTACAGAAATGGTTTCAAATGAATCTGTAGACTACCGAGCTACTTTTCCAGAAGATCAGTTTCCTAATT

CATCTCAGAACGGTTCATGCCGACAAGTGCAGTATCCTCTGACAGACATGTCCCCCATCCTAACTAGTGGGG

ACTCTGATATATCCAGTCCATTACTGCAAAATACTGTCCACATTGACCTCAGTGCTCTAAATCCAGAGCTGG

TCCAGGCAGTGCAGCATGTAGTGATTGGGCCCAGTAGCCTGATTGTGCATTTCAATGAAGTCATAGGAAGAG

GGCATTTTGGTTGTGTATATCATGGGACTTTGTTGGACAATGATGGCAAGAAAATTCACTGTGCTGTGAAAT

CCTTGAACAGAATCACTGACATAGGAGAAGTTTCCCAATTTCTGACCGAGGGAATCATCATGAAAGATTTTA

GTCATCCCAATGTCCTCTCGCTCCTGGGAATCTGCCTGCGAAGTGAAGGGTCTCCGCTGGTGGTCCTACCAT

ACATGAAACATGGAGATCTTCGAAATTTCATTCGAAATGAGACTCATAATCCAACTGTAAAAGATCTTATTG

GCTTTGGTCTTCAAGTAGCCAAAGGCATGAAATATCTTGCAAGCAAAAAGTTTGTCCACAGAGACTTGGCTG

CAAGAAACTGTATGCTGGATGAAAAATTCACAGTCAAGGTTGCTGATTTTGGTCTTGCCAGAGACATGTATG

TABLE 26-continued

MET (Full length)Nucleotide Sequence (4226 nt, SEQ ID No. 62)

ATAAAGAATACTATAGTGTACACAACAAAACAGGTGCAAAGCTGCCAGTGAAGTGGATGGCTTTGGAAAGTC

TGCAAACTCAAAAGTTTACCACCAAGTCAGATGTGTGGTCCTTTGGCGTGCTCCTCTGGGAGCTGATGACAA

GAGGAGCCCCACCTTATCCTGACGTAAACACCTTTGATATAACTGTTTACTTGTTGCAAGGGAGAAGACTCC

TACAACCCGAATACTGCCCAGACCCCTTATATGAAGTAATGCTAAAATGCTGGCACCCTAAAGCCGAAATGC

GCCCATCCTTTTCTGAACTGGTGTCCCGGATATCAGCGATCTTCTCTACTTTCATTGGGGAGCACTATGTCC

ATGTGAACGCTACTTATGTGAACGTAAAATGTGTCGCTCCGTATCCTTCTCTGTTGTCATCAGAAGATAACG

CTGATGATGAGGTGGACACACGACCAGCCTCCTTCTGGGAGACATCATAG (Double underline indicates bases bordering the splice junction between exon 26 and 28)

TABLE 27

MET variant (with non-coding exon 27) Nucleotide
Sequence (4651 nt, SEQ ID No. 65)

ATGAAGGCCCCCGCTGTGCTTGCACCTGGCATCCTCGTGCTCCTGTTTACCTTGGTGCAGAGGAGCAATGGG

AGTGTAAAGAGGCACTAGCAAAGTCCGAGATGAATGTGAATATGAAGTATCAGCTTCCCAACTTCACCGCGG

AAACACCCATCCAGAATGTCATTCTACATGAGCATCACATTTTCCTTGGTGCCACTAACTACATTTATGTTT

TAAATGAGGAAGACCTTCAGAAGGTTGCTGAGTACAAGACTGGGCCTGTGCTGGAACACCCAGATTGTTTCC

CATGTCAGGACTGCAGCAGCAAAGCCAATTTATCAGGAGGTGTTTGGAAAGATAACATCAACATGGCTCTAG

TTGTCGACACCTACTATGATGATCAACTCATTAGCTGTGGCAGCGTCAACAGAGGGACCTGCCAGCGACATG

TCTTTCCCCACAATCATACTGCTGACATACAGTCGGAGGTTCACTGCATATTCTCCCCACAGATAGAAGAGC

CCAGCCAGTGTCCTGACTGTGTGGTGAGCGCCCTGGGAGCCAAAGTCCTTTCATCTGTAAAGGACCGGTTCA

TCAACTTCTTTGTAGGCAATACCATAAATTCTTCTTATTTCCCAGATCATCCATTGCATTCGATATCAGTGA

GAAGGCTAAAGGAAACGAAAGATGGTTTTATGTTTTTGACGGACCAGTCCTACATTGATGTTTTACCTGAGT

TCAGAGATTCTTACCCCATTAAGTATGTCCATGCCTTTGAAAGCAACAATTTTATTTACTTCTTGACGGTCC

AAAGGGAAACTCTAGATGCTCAGACTTTTCACACAAGAATAATCAGGTTCTGTTCCATAAACTCTGGATTGC

ATTCCTACATGGAAATGCCTCTGGAGTGTATTCTCACAGAAAAGAGAAAAAAGAGATCCACAAAGAAGGAAG

TGTTTAATATACTTCAGGCTGCGTATGTCAGCAAGCCTGGGGCCCAGCTTGCTAGACAAATAGGAGCCAGCC

TGAATGATGACATTCTTTTCGGGGTGTTCGCACAAAGCAAGCCAGATTCTGCCGAACCAATGGATCGATCTG

CCATGTGTGCATTCCCTATCAAATATGTCAACGACTTCTTCAACAAGATCGTCAACAAAAACAATGTGAGAT

GTCTCCAGCATTTTTACGGACCCAATCATGAGCACTGCTTTAATAGGACACTTCTGAGAAATTCATCAGGCT

GTGAAGCGCGCCGTGATGAATATCGAACAGAGTTTACCACAGCTTTGCAGCGCGTTGACTTATTCATGGGTC

AATTCAGCGAAGTCCTCTTAACATCTATATCCACCTTCATTAAAGGAGACCTCACCATAGCTAATCTTGGGA

CATCAGAGGGTCGCTTCATGCAGGTTGTGGTTTCTCGATCAGGACCATCAACCCCTCATGTGAATTTTCTCC

TGGACTCCCATCCAGTGTCTCCAGAAGTGATTGTGGAGCATACATTAAACCAAAATGGCTACACACTGGTTA

TCACTGGGAAGAAGATCACGAAGATCCCATTGAATGGCTTGGGCTGCAGACATTTCCAGTCCTGCAGTCAAT

GCCTCTCTGCCCCACCCTTTGTTCAGTGTGGCTGGTGCCACGACAAATGTGTGCGATCGGAGGAATGCCTGA

GCGGGACATGGACTCAACAGATCTGTCTGCCTGCAATCTACAAGGTTTTCCCAAATAGTGCACCCCTTGAAG

GAGGGACAAGGCTGACCATATGTGGCTGGGACTTTGGATTTCGGAGGAATAATAAATTTGATTTAAAGAAAA

CTAGAGTTCTCCTTGGAAATGAGAGCTGCACCTTGACTTTAAGTGAGAGCACGATGAATACATTGAAATGCA

CAGTTGGTCCTGCCATGAATAAGCATTTCAATATGTCCATAATTATTTCAAATGGCCACGGGACAACACAAT

ACAGTACATTCTCCTATGTGGATCCTGTAATAACAAGTATTTCGCCGAAATACGGTCCTATGGCTGGTGGCA

TABLE 27-continued

MET variant (with non-coding exon 27) Nucleotide Sequence (4651 nt, SEQ ID No. 65)

CTTTACTTACTTTAACTGGAAATTACCTAAACAGTGGGAATTCTAGACACATTTCAATTGGTGGAAAAACAT

GTACTTTAAAAAGTGTGTCAAACAGTATTCTTGAATGTTATACCCCAGCCCAAACCATTTCAACTGAGTTTG

CTGTTAAATTGAAAATTGACTTAGCCAACCGAGAGACAAGCATCTTCAGTTACCGTGAAGATCCCATTGTCT

ATGAAATTCATCCAACCAAATCTTTTATTAGTACTTGGTGGAAAGAACCTCTCAACATTGTCAGTTTTCTAT

TTTGCTTTGCCAGTGGTGGGAGCACAATAACAGGTGTTGGGAAAAACCTGAATTCAGTTAGTGTCCCGAGAA

TGGTCATAAATGTGCATGAAGCAGGAAGGAACTTTACAGTGGCATGTCAACATCGCTCTAATTCAGAGATAA

TCTGTTGTACCACTCCTTCCCTGCAACAGCTGAATCTGCAACTCCCCCTGAAAACCAAAGCCTTTTTCATGT

TAGATGGGATCCTTTCCAAATACTTTGATCTCATTTATGTACATAATCCTGTGTTTAAGCCTTTTGAAAAGC

CAGTGATGATCTCAATGGGCAATGAAAATGTACTGGAAATTAAG<u>gtgggagcagtggcaattcagggag</u>

<u>attattttagtatcatggttcaatattttttcatacttcattttcttatgtatgagaggaaagc</u>

<u>aaaggcataagagaatatttgttgtgtcagcaatctaactctttatcaatacgttaagttgatca</u>

<u>cattaaaacttctacctctcagccaggcacggtagctcatacctgtaatcccagcactttgggag</u>

<u>gccaaggcgggtgaatcacttgagatcaggagttcaagaccagcctggccaaaatggtgaaaccc</u>

<u>catctccactaaaaatacaaaaattagctgggcatggtggtgggtgcctgtaatcccagctactc</u>

<u>aggaggctgagggacggaggtgacctgagtcctgaaggcgg</u>aggttgcagtgagccaagatggca

<u>ccactgcact</u>GGAAATGATATTGACCCTGAAGCAGTTAAAGGTGAAGTGTTAAAAGTTGGAAATAAGAGC

TGTGAGAATATACACTTACATTCTGAAGCCGTTTTATGCACGGTCCCCAATGACCTGCTGAAATTGAACAGC

GAGCTAAATATAGAGTGGAAGCAAGCAATTTCTTCAACCGTCCTTGGAAAAGTAATAGTTCAACCAGATCAG

AATTTCACAGGATTGATTGCTGGTGTTGTCTCAATATCAACAGCACTGTTATTACTACTTGGGTTTTTCCTG

TGGCTGAAAAAGAGAAAGCAAATTAAAGATCTGGGCAGTGAATTAGTTCGCTACGATGCAAGAGTACACACT

CCTCATTTGGATAGGCTTGTAAGTGCCCGAAGTGTAAGCCCAACTACAGAAATGGTTTCAAATGAATCTGTA

GACTACCGAGCTACTTTTCCAGAAGATCAGTTTCCTAATTCATCTCAGAACGGTTCATGCCGACAAGTGCAG

TATCCTCTGACAGACATGTCCCCCATCCTAACTAGTGGGGACTCTGATATATCCAGTCCATTACTGCAAAAT

ACTGTCCACATTGACCTCAGTGCTCTAAATCCAGAGCTGGTCCAGGCAGTGCAGCATGTAGTGATTGGGCCC

AGTAGCCTGATTGTGCATTTCAATGAAGTCATAGGAAGAGGGCATTTTGGTTGTGTATATCATGGGACTTTG

TTGGACAATGATGGCAAGAAAATTCACTGTGCTGTGAAATCCTTGAACAGAATCACTGACATAGGAGAAGTT

TCCCAATTTCTGACCGAGGGAATCATCATGAAAGATTTTAGTCATCCCAATGTCCTCTCGCTCCTGGGAATC

TGCCTGCGAAGTGAAGGGTCTCCGCTGGTGGTCCTACCATACATGAAACATGGAGATCTTCGAAATTTCATT

CGAAATGAGACTCATAATCCAACTGTAAAAGATCTTATTGGCTTTGGTCTTCAAGTAGCCAAAGGCATGAAA

TATCTTGCAAGCAAAAAGTTTGTCCACAGAGACTTGGCTGCAAGAAACTGTATGCTGGATGAAAAATTCACA

GTCAAGGTTGCTGATTTTGGTCTTGCCAGAGACATGTATGATAAAGAATACTATAGTGTACACAACAAAACA

GGTGCAAAGCTGCCAGTGAAGTGGATGGCTTTGGAAAGTCTGCAAACTCAAAAGTTTACCACCAAGTCAGAT

GTGTGGTCCTTTGGCGTGCTCCTCTGGGAGCTGATGACAAGAGGAGCCCCACCTTATCCTGACGTAAACACC

TTTGATATAACTGTTTACTTGTTGCAAGGGAGAAGACTCCTACAACCCGAATACTGCCCAGACCCCTTATAT

GAAGTAATGCTAAAATGCTGGCACCCTAAAGCCGAAATGCGCCCATCCTTTTCTGAACTGGTGTCCCGGATA

TABLE 27-continued

MET variant (with non-coding exon 27) Nucleotide Sequence (4651 nt, SEQ ID No. 65)

TCAGCGATCTTCTCTACTTTCATTGGGGAGCACTATGTCCATGTGAACGCTACTTATGTGAACGTAAAATGT

GTCGCTCCGTATCCTTCTCTGTTGTCATCAGAAGATAACGCTGATGATGAGGTGGACACACGACCAGCCTCC

TTCTGGGAGACATCATAG (Exon 27 is indicated as double underline.)

TABLE 28

Primer across the junction between MET exon 26 and 28

Primer across the junction between MET exon 26 and 28 (SEQ ID No. 61): CTGGAAATTAAGGGAAATG

(Double underline indicates bases bordering the splice junction)

TABLE 29 siRNA for selectively knockdown MET full length and variants expression siRNA targeting splice junction between MET exon 26 and exon 28

Sense (SEQ ID No. 63) 5' GUACUGGAAAUUAAGGGAAdTdT 3'

TABLE 29-continued siRNA for selectively knockdown MET full length and variants expression

Antisense (SEQ ID No. 64) 3' dTdTCAUGACCUUUAAUUCC-CUU (5'-P)5' siRNA targeting non-coding MET exon 27

Sense (SEQ ID No. 68) 5' CAGCAAUCUAACUCUUUAUdTdT 3'

Antisense (SEQ ID No. 69) 3' dTdTGUCGUUAGAUUGAGAA-AUA (5'-P)5'

(Double underline indicates bases bordering the splice junction)

TABLE 30

NF1 (full length) Nucleotide Sequence (8520 nt, SEQ ID No. 70)

ATGGCCGCGCACAGGCCGGTGGAATGGGTCCAGGCCGTGGTCAGCCGCTTCGACGAGCAGCTTCCAATAA

AAACAGGACAGCAGAACACACATACCAAAGTCAGTACTGAGCACAACAAGGAATGTCTAATCAATATTTC

CAAATACAAGTTTTCTTTGGTTATAAGCGGCCTCACTACTATTTTAAAGAATGTTAACAATATGAGAATA

TTTGGAGAAGCTGCTGAAAAAAATTTATATCTCTCTCAGTTGATTATATTGGATACACTGGAAAAATGTC

TTGCTGGGCAACCAAAGGACACAATGAGATTAGATGAAACGATGCTGGTCAAACAGTTGCTGCCAGAAAT

CTGCCATTTTCTTCACACCTGTCGTGAAGGAAACCAGCATGCAGCTGAACTTCGGAATTCTGCCTCTGGG

GTTTTATTTTCTCTCAGCTGCAACAACTTCAATGCAGTCTTTAGTCGCATTTCTACCAGGTTACAGGAAT

TAACTGTTTGTTCAGAAGACAATGTTGATGTTCATGATATAGAATTGTTACAGTATATCAATGTGGATTG

TGCAAAATTAAAACGACTCCTGAAGGAAACAGCATTTAAATTTAAAGCCCTAAAGAAGGTTGCGCAGTTA

GCAGTTATAAATAGCCTGGAAAAGGCATTTTGGAACTGGGTAGAAAATTATCCAGATGAATTTACAAAAC

TGTACCAGATCCCACAGACTGATATGGCTGAATGTGCAGAAAAGCTATTTGACTTGGTGGATGGTTTTGC

TGAAAGCACCAAACGTAAAGCAGCAGTTTGGCCACTACAAATCATTCTCCTTATCTTGTGTCCAGAAATA

ATCCAGGATATATCCAAAGACGTGGTTGATGAAAACAACATGAATAAGAAGTTATTTCTGGACAGTCTAC

GAAAAGCTCTTGCTGGCCATGGAGGAAGTAGGCAGCTGACAGAAAGTGCTGCAATTGCCTGTGTCAAACT

GTGTAAAGCAAGTACTTACATCAATTGGGAAGATAACTCTGTCATTTTCCTACTTGTTCAGTCCATGGTG

TABLE 30-continued

NF1 (full length)Nucleotide Sequence (8520 nt, SEQ ID No. 70)

GTTGATCTTAAGAACCTGCTTTTTAATCCAAGTAAGCCATTCTCAAGAGGCAGTCAGCCTGCAGATGTGG

ATCTAATGATTGACTGCCTTGTTTCTTGCTTTCGTATAAGCCCTCACAACAACCAACACTTTAAGATCTG

CCTGGCTCAGAATTCACCTTCTACATTTCACTATGTGCTGGTAAATTCACTCCATCGAATCATCACCAAT

TCCGCATTGGATTGGTGGCCTAAGATTGATGCTGTGTATTGTCACTCGGTTGAACTTCGAAATATGTTTG

GTGAAACACTTCATAAAGCAGTGCAAGGTTGTGGAGCACACCCAGCAATACGAATGGCACCGAGTCTTAC

ATTTAAAGAAAAAGTAACAAGCCTTAAATTTAAAGAAAAACCTACAGACCTGGAGACAAGAAGCTATAAG

TATCTTCTCTTGTCCATGGTGAAACTAATTCATGCAGATCCAAAGCTCTTGCTTTGTAATCCAAGAAAAC

AGGGGCCCGAAACCCAAGGCAGTACAGCAGAATTAATTACAGGGCTCGTCCAACTGGTCCCTCAGTCACA

CATGCCAGAGATTGCTCAGGAAGCAATGGAGGCTCTGCTGGTTCTTCATCAGTTAGATAGCATTGATTTG

TGGAATCCTGATGCTCCTGTAGAAACATTTTGGGAGATTAGCTCACAAATGCTTTTTTACATCTGCAAGA

AATTAACTAGTCATCAAATGCTTAGTAGCACAGAAATTCTCAAGTGGTTGCGGGAAATATTGATCTGCAG

GAATAAATTTCTTCTTAAAAATAAGCAGGCAGATAGAAGTTCCTGTCACTTTCTCCTTTTTTACGGGGTA

GGATGTGATATTCCTTCAGTGGAAATACCAGTCAAATGTCCATGGATCATGAAGAATTACTACGTACTC

CTGGAGCCTCTCTCCGGAAGGGAAAAGGGAACTCCTCTATGGATAGTGCAGCAGGATGCAGCGGAACCCC

CCCGATTTGCCGACAAGCCCAGACCAAACTAGAAGTGGCCCTGTACATGTTTCTGTGGAACCCTGACACT

GAAGCTGTTCTGGTTGCCATGTCCTGTTTCCGCCACCTCTGTGAGGAAGCAGATATCCGGTGTGGGGTGG

ATGAAGTGTCAGTGCATAACCTCTTGCCCAACTATAACACATTCATGGAGTTTGCCTCTGTCAGCAATAT

GATGTCAACAGGAAGAGCAGCACTTCAGAAAAGAGTGATGGCACTGCTGAGGCGCATTGAGCATCCCACT

GCAGGAAACACTGAGGCTTGGAAGATACACATGCAAAATGGGAACAAGCAACAAAGCTAATCCTTAACT

ATCCAAAAGCCAAAATGGAAGATGGCCAGGCTGCTGAAAGCCTTCACAAGACCATTGTTAAGAGGCGAAT

GTCCCATGTGAGTGGAGGAGGATCCATAGATTTGTCTGACACAGACTCCCTACAGGAATGGATCAACATG

ACTGGCTTCCTTTGTGCCCTTGGGGGAGTGTGCCTCCAGCAGAGAAGCAATTCTGGCCTGGCAACCTATA

GCCCACCCATGGGTCCAGTCAGTGAACGTAAGGGTTCTATGATTTCAGTGATGTCTTCAGAGGGAAACGC

AGATACACCTGTCAGCAAATTTATGGATCGGCTGTTGTCCTTAATGGTGTGTAACCATGAGAAAGTGGGA

CTTCAAATACGGACCAATGTTAAGGATCTGGTGGGTCTAGAATTGAGTCCTGCTCTGTATCCAATGCTAT

TTAACAAATTGAAGAATACCATCAGCAAGTTTTTTGACTCCCAAGGACAGGTTTTATTGACTGATACCAA

TACTCAATTTGTAGAACAAACCATAGCTATAATGAAGAACTTGCTAGATAATCATACTGAAGGCAGCTCT

GAACATCTAGGGCAAGCTAGCATTGAAACAATGATGTTAAATCTGGTCAGGTATGTTCGTGTGCTTGGGA

ATATGGTCCATGCAATTCAAATAAAAACGAAACTGTGTCAATTAGTTGAAGTAATGATGGCAAGGAGAGA

TGACCTCTCATTTTGCCAAGAGATGAAATTTAGGAATAAGATGGTAGAATACCTGACAGACTGGGTTATG

GGAACATCAAACCAAGCAGCAGATGATGATGTAAAATGTCTTACAAGAGATTTGGACCAGGCAAGCATGG

AAGCAGTAGTTTCACTTCTAGCTGGTCTCCCTCTGCAGCCTGAAGAAGGAGATGGTGTGGAATTGATGGA

AGCCAAATCACAGTTATTTCTTAAATACTTCACATTATTTATGAACCTTTTGAATGACTGCAGTGAAGTT

GAAGATGAAAGTGCGCAAACAGGTGGCAGGAAACGTGGCATGTCTCGGAGGCTGGCATCACTGAGGCACT

GTACGGTCCTTGCAATGTCAAACTTACTCAATGCCAACGTAGACAGTGGTCTCATGCACTCCATAGGCTT

AGGTTACCACAAGGATCTCCAGACAAGAGCTACATTTATGGAAGTTCTGACAAAAATCCTTCAACAAGGC

ACAGAATTTGACACACTTGCAGAAACAGTATTGGCTGATCGGTTTGAGAGATTGGTGGAACTGGTCACAA

TGATGGGTGATCAAGGAGAACTCCCTATAGCGATGGCTCTGGCCAATGTGGTTCCTTGTTCTCAGTGGGA

TGAACTAGCTCGAGTTCTGGTTACTCTGTTTGATTCTCGGCATTTACTCTACCAACTGCTCTGGAACATG

TABLE 30-continued

NF1 (full length)Nucleotide Sequence (8520 nt, SEQ ID No. 70)

```
TTTTCTAAAGAAGTAGAATTGGCAGACTCCATGCAGACTCTCTTCCGAGGCAACAGCTTGGCCAGTAAAA
TAATGACATTCTGTTTCAAGGTATATGGTGCTACCTATCTACAAAAACTCCTGGATCCTTTATTACGAAT
TGTGATCACATCCTCTGATTGGCAACATGTTAGCTTTGAAGTGGATCCTACCAGGTTAGAACCATCAGAG
AGCCTTGAGGAAAACCAGCGGAACCTCCTTCAGATGACTGAAAAGTTCTTCCATGCCATCATCAGTTCCT
CCTCAGAATTCCCCCCTCAACTTCGAAGTGTGTGCCACTGTTTATACCAGGCAACTTGCCACTCCCTACT
GAATAAAGCTACAGTAAAAGAAAAAAAGGAAAACAAAAAATCAGTGGTTAGCCAGCGTTTCCCTCAGAAC
AGCATCGGTGCAGTAGGAAGTGCCATGTTCCTCAGATTTATCAATCCTGCCATTGTCTCACCGTATGAAG
CAGGGATTTTAGATAAAAAGCCACCACCTAGAATCGAAAGGGGCTTGAAGTTAATGTCAAAGATACTTCA
GAGTATTGCCAATCATGTTCTCTTCACAAAAGAAGAACATATGCGGCCTTTCAATGATTTTGTGAAAAGC
AACTTTGATGCAGCACGCAGGTTTTTCCTTGATATAGCATCTGATTGTCCTACAAGTGATGCAGTAAATC
ATAGTCTTTCCTTCATAAGTGACGGCAATGTGCTTGCTTTACATCGTCTACTCTGGAACAATCAGGAGAA
AATTGGGCAGTATCTTTCCAGCAACAGGGATCATAAAGCTGTTGGAAGACGACCTTTTGATAAGATGGCA
ACACTTCTTGCATACCTGGGTCCTCCAGAGCACAAACCTGTGGCAGATACACACTGGTCCAGCCTTAACC
TTACCAGTTCAAAGTTTGAGGAATTTATGACTAGGCATCAGGTACATGAAAAGAAGAATTCAAGGCTTT
GAAAACGTTAAGTATTTTCTACCAAGCTGGGACTTCCAAAGCTGGGAATCCTATTTTTTATTATGTTGCA
CGGAGGTTCAAAACTGGTCAAATCAATGGTGATTTGCTGATATACCATGTCTTACTGACTTTAAAGCCAT
ATTATGCAAAGCCATATGAAATTGTAGTGGACCTTACCCATACCGGGCCTAGCAATCGCTTTAAAACAGA
CTTTCTCTCTAAGTGGTTTGTTGTTTTTCCTGGCTTTGCTTACGACAACGTCTCCGCAGTCTATATCTAT
AACTGTAACTCCTGGGTCAGGGAGTACACCAAGTATCATGAGCGGCTGCTGACTGGCCTCAAAGGTAGCA
AAAGGCTTGTTTTCATAGACTGTCCTGGGAAACTGGCTGAGCACATAGAGCATGAACAACAGAAACTACC
TGCTGCCACCTTGGCTTTAGAAGAGGACCTGAAGGTATTCCACAATGCTCTCAAGCTAGCTCACAAAGAC
ACCAAAGTTTCTATTAAAGTTGGTTCTACTGCTGTCCAAGTAACTTCAGCAGAGCGAACAAAAGTCCTAG
GGCAATCAGTCTTTCTAAATGACATTTATTATGCTTCGGAAATTGAAGAAATCTGCCTAGTAGATGAGAA
CCAGTTCACCTTAACCATTGCAAACCAGGGCACGCCGCTCACCTTCATGCACCAGGAGTGTGAAGCCATT
GTCCAGTCTATCATTCATATCCGGACCCGCTGGGAACTGTCACAGCCCGACTCTATCCCCCAACACACCA
AGATTCGGCCAAAAGATGTCCCTGGGACACTGCTCAATATCGCATTACTTAATTTAGGCAGTTCTGACCC
GAGTTTACGGTCAGCTGCCTATAATCTTCTGTGTGCCTTAACTTGTACCTTTAATTTAAAAATCGAGGGC
CAGTTACTAGAGACATCAGGTTTATGTATCCCTGCCAACAACACCCTCTTTATTGTCTCTATTAGTAAGA
CACTGGCAGCCAATGAGCCACACCTCACGTTAGAATTTTTGGAAGAGTGTATTTCTGGATTTAGCAAATC
TAGTATTGAATTGAAACACCTTTGTTTGGAATACATGACTCCATGGCTGTCAAATCTAGTTCGTTTTTGC
AAGCATAATGATGATGCCAAACGACAAAGAGTTACTGCTATTCTTGACAAGCTGATAACAATGACCATCA
ATGAAAAACAGATGTACCCATCTATTCAAGCAAAAATATGGGGAAGCCTTGGGCAGATTACAGATCTGCT
TGATGTTGTACTAGACAGTTTCATCAAAACCAGTGCAACAGGTGGCTTGGGATCAATAAAAGCTGAGGTG
ATGGCAGATACTGCTGTAGCTTTGGCTTCTGGAAATGTGAAATTGGTTTCAAGCAAGGTTATTGGAAGGA
TGTGCAAAATAATTGACAAGACATGCTTATCTCCAACTCCTACTTTAGAACAACATCTTATGTGGGATGA
TATTGCTATTTTAGCACGCTACATGCTGATGCTGTCCTTCAACAATTCCCTTGATGTGGCAGCTCATCTT
CCCTACCTCTTCCACGTTGTTACTTTCTTAGTAGCCACAGGTCCGCTCTCCCTTAGAGCTTCCACACATG
GACTGGTCATTAATATCATTCACTCTCTGTGTACTTGTTCACAGCTTCATTTTAGTGAAGAGACCAAGCA
AGTTTTGAGACTCAGTCTGACAGAGTTCTCATTACCCAAATTTTACTTGCTGTTTGGCATTAGCAAAGTC
```

TABLE 30-continued

NF1 (full length)Nucleotide Sequence (8520 nt, SEQ ID No. 70)

AAGTCAGCTGCTGTCATTGCCTTCCGTTCCAGTTACCGGGACAGGTCATTCTCTCCTGGCTCCTATGAGA

GAGAGACTTTTGCTTTGACATCCTTGGAAACAGTCACAGAAGCTTTGTTGGAGATCATGGAGGCATGCAT

GAGAGATATTCCAACGTGCAAGTGGCTGGACCAGTGGACAGAACTAGCTCAAAGATTTGCATTCCAATAT

AATCCATCCCTGCAACCAAGAGCTCTTGTTGTCTTTGGGTGTATTAGCAAACGAGTGTCTCATGGGCAGA

TAAAGCAGATAATCCGTATTCTTAGCAAGGCACTTGAGAGTTGCTTAAAAGGACCTGACACTTACAACAG

TCAAGTTCTGATAGAAGCTACAGTAATAGCACTAACCAAATTACAGCCACTTCTTAATAAGGACTCGCCT

CTGCACAAAGCCCTCTTTTGGGTAGCTGTGGCTGTGCTGCAGCTTGATGAGGTCAACTTGTATTCAGCAG

GTACCGCACTTCTTGAACAAAACCTGCATACTTTAGATAGTCTCCGTATATTCAATGACAAGAGTCCAGA

GGAAGTATTTATGGCAATCCGGAATCCTCTGGAGTGGCACTGCAAGCAAATGGATCATTTTGTTGGACTC

AATTTCAACTCTAACTTTAACTTTGCATTGGTTGGACACCTTTTAAAAGGGTACAGGCATCCTTCACCTG

CTATTGTTGCAAGAACAGTCAGAATTTTACATACACTACTAACTCTGGTTAACAAACACAGAAATTGTGA

CAAATTTGAAGTGAATACACAGAGCGTGGCCTACTTAGCAGCTTTACTTACAGTGTCTGAAGAAGTTCGA

AGTCGCTGCAGCCTAAAACATAGAAAGTCACTTCTTCTTACTGATATTTCAATGGAAAATGTTCCTATGG

ATACATATCCCATTCATCATGGTGACCCTTCCTATAGGACACTAAAGGAGACTCAGCCATGGTCCTCTCC

CAAAGGTTCTGAAGGATACCTTGCAGCCACCTATCCAACTGTCGGCCAGACCAGTCCCCGAGCCAGGAAA

TCCATGAGCCTGGACATGGGGCAACCTTCTCAGGCCAACACTAAGAAGTTGCTTGGAACAAGGAAAAGTT

TTGATCACTTGATATCAGACACAAAGGCTCCTAAAAGGCAAGAAATGGAATCAGGGATCACAACACCCCC

CAAAATGAGGAGAGTAGCAGAAACTGATTATGAAATGGAAACTCAGAGGATTTCCTCATCACAACAGCAC

CCACATTTACGTAAAGTTTCAGTGTCTGAATCAAATGTTCTCTTGGATGAAGAAGTACTTACTGATCCGA

AGATCCAGGCGCTGCTTCTTACTGTTCTAGCTACACTGGTAAAATATACCACAGATGAGTTTGATCAACG

AATTCTTTATGAATACTTAGCAGAGGCCAGTGTTGTGTTTCCCAAAGTCTTTCCTGTTGTGCATAATTTG

TTGGACTCTAAGATCAACACCCTGTTATCATTGTGCCAAGATCCAAATTTGTTAAATCCAATCCATGGAA

TTGTGCAGAGTGTGGTGTACCATGAAGAATCCCCACCACAATACCAAACATCTTACCTGCAAAGTTTTGG

TTTTAATGGCTTGTGGCGGTTTGCAGGACCGTTTTCAAAGCAAACACAAATTCCAGACTATGCTGAGCTT

ATTGTTAAGTTTCTTGATGCCTTGATTGACACGTACCTGCCTGGAATTGATGAAGAAACCAGTGAAGAAT

CCCTCCTGACTCCCACATCTCCTTACCCTCCTGCACTGCAGAGCCAGCTTAGTATCACTGCCAACCTTAA

CCTTTCTAATTCCATGACCTCACTTGCAACTTCCCAGCATTCCCCAGGAATCGACAAGGAGAACGTTGAA

CTCTCCCCTACCACTGGCCACTGTAACAGTGGACGAACTCGCCACGGATCCGCAAGCCAAGTGCAGAAGC

AAAGAAGCGCTGGCAGTTTCAAACGTAATAGCATTAAGAAGATCGTGTGA (Exon 8 is indicated as double underline.)

TABLE 31

NF1 variant (lacking exon 8) Nucleotide Sequence
(8444 nt, SEQ ID No. 76)

ATGGCCGCGCACAGGCCGGTGGAATGGGTCCAGGCCGTGGTCAGCCGCTTCGACGAGCAGCTTCCAATAA

AAACAGGACAGCAGAACACACATACCAAAGTCAGTACTGAGCACAACAAGGAATGTCTAATCAATATTTC

CAAATACAAGTTTTCTTTGGTTATAAGCGGCCTCACTACTATTTTAAAGAATGTTAACAATATGAGAATA

TTTGGAGAAGCTGCTGAAAAAAATTTATATCTCTCTCAGTTGATTATATTGGATACACTGGAAAATGTC

TTGCTGGGCAACCAAAGGACACAATGAGATTAGATGAAACGATGCTGGTCAAACAGTTGCTGCCAGAAAT

TABLE 31-continued

NF1 variant (lacking exon 8) Nucleotide Sequence
(8444 nt, SEQ ID No. 76)

CTGCCATTTTCTTCACACCTGTCGTGAAGGAAACCAGCATGCAGCTGAACTTCGGAATTCTGCCTCTGGG

GTTTTATTTTCTCTCAGCTGCAACAACTTCAATGCAGTCTTTAGTCGCATTTCTACCAGGTTACAGGAAT

TAACTGTTTGTTCAGAAGACAATGTTGATGTTCATGATATAGAATTGTTACAGTATATCAATGTGGATTG

TGCAAAATTAAAACGACTCCTGAAGGAAACAGCATTTAAATTTAAAGCCCTAAAGAAGGTTGCGCAGTTA

GCAGTTATAAATAGCCTGGAAAAGAATGTGCAGAAAAGCTATTTGACTTGGTGGATGGTTTTGCTGAAAG

CACCAAACGTAAAGCAGCAGTTTGGCCACTACAAATCATTCTCCTTATCTTGTGTCCAGAAATAATCCAG

GATATATCCAAAGACGTGGTTGATGAAAACAACATGAATAAGAAGTTATTTCTGGACAGTCTACGAAAAG

CTCTTGCTGGCCATGGAGGAAGTAGGCAGCTGACAGAAAGTGCTGCAATTGCCTGTGTCAAACTGTGTAA

AGCAAGTACTTACATCAATTGGGAAGATAACTCTGTCATTTTCCTACTTGTTCAGTCCATGGTGGTTGAT

CTTAAGAACCTGCTTTTTAATCCAAGTAAGCCATTCTCAAGAGGCAGTCAGCCTGCAGATGTGGATCTAA

TGATTGACTGCCTTGTTTCTTGCTTTCGTATAAGCCCTCACAACAACCAACACTTTAAGATCTGCCTGGC

TCAGAATTCACCTTCTACATTTCACTATGTGCTGGTAAATTCACTCCATCGAATCATCACCAATTCCGCA

TTGGATTGGTGGCCTAAGATTGATGCTGTGTATTGTCACTCGGTTGAACTTCGAAATATGTTTGGTGAAA

CACTTCATAAAGCAGTGCAAGGTTGTGGAGCACACCCAGCAATACGAATGGCACCGAGTCTTACATTTAA

AGAAAAAGTAACAAGCCTTAAATTTAAAGAAAAACCTACAGACCTGGAGACAAGAAGCTATAAGTATCTT

CTCTTGTCCATGGTGAAACTAATTCATGCAGATCCAAAGCTCTTGCTTTGTAATCCAAGAAAACAGGGGC

CCGAAACCCAAGGCAGTACAGCAGAATTAATTACAGGGCTCGTCCAACTGGTCCCTCAGTCACACATGCC

AGAGATTGCTCAGGAAGCAATGGAGGCTCTGCTGGTTCTTCATCAGTTAGATAGCATTGATTTGTGGAAT

CCTGATGCTCCTGTAGAAACATTTTGGGAGATTAGCTCACAAATGCTTTTTTACATCTGCAAGAAATTAA

CTAGTCATCAAATGCTTAGTAGCACAGAAATTCTCAAGTGGTTGCGGGAAATATTGATCTGCAGGAATAA

ATTTCTTCTTAAAAATAAGCAGGCAGATAGAAGTTCCTGTCACTTTCTCCTTTTTTACGGGGTAGGATGT

GATATTCCTTCTAGTGGAAATACCAGTCAAATGTCCATGGATCATGAAGAATTACTACGTACTCCTGGAG

CCTCTCTCCGGAAGGGAAAAGGGAACTCCTCTATGGATAGTGCAGCAGGATGCAGCGGAACCCCCCCGAT

TTGCCGACAAGCCCAGACCAAACTAGAAGTGGCCCTGTACATGTTTCTGTGGAACCCTGACACTGAAGCT

GTTCTGGTTGCCATGTCCTGTTTCCGCCACCTCTGTGAGGAAGCAGATATCCGGTGTGGGGTGGATGAAG

TGTCAGTGCATAACCTCTTGCCCAACTATAACACATTCATGGAGTTTGCCTCTGTCAGCAATATGATGTC

AACAGGAAGAGCAGCACTTCAGAAAAGAGTGATGGCACTGCTGAGGCGCATTGAGCATCCCACTGCAGGA

AACACTGAGGCTTGGGAAGATACACATGCAAAATGGGAACAAGCAACAAAGCTAATCCTTAACTATCCAA

AAGCCAAAATGGAAGATGGCCAGGCTGCTGAAAGCCTTCACAAGACCATTGTTAAGAGGCGAATGTCCCA

TGTGAGTGGAGGAGGATCCATAGATTTGTCTGACACAGACTCCCTACAGGAATGGATCAACATGACTGGC

TTCCTTTGTGCCCTTGGGGGAGTGTGCCTCCAGCAGAGAAGCAATTCTGGCCTGGCAACCTATAGCCCAC

CCATGGGTCCAGTCAGTGAACGTAAGGGTTCTATGATTTCAGTGATGTCTTCAGAGGGAAACGCAGATAC

ACCTGTCAGCAAATTTATGGATCGGCTGTTGTCCTTAATGGTGTGTAACCATGAGAAAGTGGGACTTCAA

ATACGGACCAATGTTAAGGATCTGGTGGGTCTAGAATTGAGTCCTGCTCTGTATCCAATGCTATTTAACA

AATTGAAGAATACCATCAGCAAGTTTTTTGACTCCCAAGGACAGGTTTTATTGACTGATACCAATACTCA

ATTTGTAGAACAAACCATAGCTATAATGAAGAACTTGCTAGATAATCATACTGAAGGCAGCTCTGAACAT

CTAGGGCAAGCTAGCATTGAAACAATGATGTTAAATCTGGTCAGGTATGTTCGTGTGCTTGGGAATATGG

TCCATGCAATTCAAATAAAAACGAAACTGTGTCAATTAGTTGAAGTAATGATGGCAAGGAGAGATGACCT

CTCATTTTGCCAAGAGATGAAATTTAGGAATAAGATGGTAGAATACCTGACAGACTGGGTTATGGGAACA

TABLE 31-continued

NF1 variant (lacking exon 8) Nucleotide Sequence
(8444 nt, SEQ ID No. 76)

```
TCAAACCAAGCAGCAGATGATGATGTAAAATGTCTTACAAGAGATTTGGACCAGGCAAGCATGGAAGCAG
TAGTTTCACTTCTAGCTGGTCTCCCTCTGCAGCCTGAAGAAGGAGATGGTGTGGAATTGATGGAAGCCAA
ATCACAGTTATTTCTTAAATACTTCACATTATTTATGAACCTTTTGAATGACTGCAGTGAAGTTGAAGAT
GAAAGTGCGCAAACAGGTGGCAGGAAACGTGGCATGTCTCGGAGGCTGGCATCACTGAGGCACTGTACGG
TCCTTGCAATGTCAAACTTACTCAATGCCAACGTAGACAGTGGTCTCATGCACTCCATAGGCTTAGGTTA
CCACAAGGATCTCCAGACAAGAGCTACATTTATGGAAGTTCTGACAAAAATCCTTCAACAAGGCACAGAA
TTTGACACACTTGCAGAAACAGTATTGGCTGATCGGTTTGAGAGATTGGTGGAACTGGTCACAATGATGG
GTGATCAAGGAGAACTCCCTATAGCGATGGCTCTGGCCAATGTGGTTCCTTGTTCTCAGTGGGATGAACT
AGCTCGAGTTCTGGTTACTCTGTTTGATTCTCGGCATTTACTCTACCAACTGCTCTGGAACATGTTTTCT
AAAGAAGTAGAATTGGCAGACTCCATGCAGACTCTCTTCCGAGGCAACAGCTTGGCCAGTAAAATAATGA
CATTCTGTTTCAAGGTATATGGTGCTACCTATCTACAAAAACTCCTGGATCCTTTATTACGAATTGTGAT
CACATCCTCTGATTGGCAACATGTTAGCTTTGAAGTGGATCCTACCAGGTTAGAACCATCAGAGAGCCTT
GAGGAAAACCAGCGGAACCTCCTTCAGATGACTGAAAAGTTCTTCCATGCCATCATCAGTTCCTCCTCAG
AATTCCCCCCTCAACTTCGAAGTGTGTGCCACTGTTTATACCAGGCAACTTGCCACTCCCTACTGAATAA
AGCTACAGTAAAAGAAAAAAAGGAAAACAAAAAATCAGTGGTTAGCCAGCGTTTCCCTCAGAACAGCATC
GGTGCAGTAGGAAGTGCCATGTTCCTCAGATTTATCAATCCTGCCATTGTCTCACCGTATGAAGCAGGGA
TTTTAGATAAAAAGCCACCACCTAGAATCGAAAGGGGCTTGAAGTTAATGTCAAAGATACTTCAGAGTAT
TGCCAATCATGTTCTCTTCACAAAAGAAGAACATATGCGGCCTTTCAATGATTTTGTGAAAAGCAACTTT
GATGCAGCACGCAGGTTTTTCCTTGATATAGCATCTGATTGTCCTACAAGTGATGCAGTAAATCATAGTC
TTTCCTTCATAAGTGACGGCAATGTGCTTGCTTTACATCGTCTACTCTGGAACAATCAGGAGAAAATTGG
GCAGTATCTTTCCAGCAACAGGGATCATAAAGCTGTTGGAAGACGACCTTTTGATAAGATGGCAACACTT
CTTGCATACCTGGGTCCTCCAGAGCACAAACCTGTGGCAGATACACACTGGTCCAGCCTTAACCTTACCA
GTTCAAAGTTTGAGGAATTTATGACTAGGCATCAGGTACATGAAAAAGAAGAATTCAAGGCTTTGAAAAC
GTTAAGTATTTTCTACCAAGCTGGGACTTCCAAAGCTGGGAATCCTATTTTTTATTATGTTGCACGGAGG
TTCAAAACTGGTCAAATCAATGGTGATTTGCTGATATACCATGTCTTACTGACTTTAAAGCCATATTATG
CAAAGCCATATGAAATTGTAGTGGACCTTACCCATACCGGGCCTAGCAATCGCTTTAAAACAGACTTTCT
CTCTAAGTGGTTTGTTGTTTTTCCTGGCTTTGCTTACGACAACGTCTCCGCAGTCTATATCTATAACTGT
AACTCCTGGGTCAGGGAGTACACCAAGTATCATGAGCGGCTGCTGACTGGCCTCAAAGGTAGCAAAAGGC
TTGTTTTCATAGACTGTCCTGGGAAACTGGCTGAGCACATAGAGCATGAACAACAGAAACTACCTGCTGC
CACCTTGGCTTTAGAAGAGGACCTGAAGGTATTCCACAATGCTCTCAAGCTAGCTCACAAAGACACCAAA
GTTTCTATTAAAGTTGGTTCTACTGCTGTCCAAGTAACTTCAGCAGAGCGAACAAAAGTCCTAGGGCAAT
CAGTCTTTCTAAATGACATTTATTATGCTTCGGAAATTGAAGAAATCTGCCTAGTAGATGAGAACCAGTT
CACCTTAACCATTGCAAACCAGGGCACGCCGCTCACCTTCATGCACCAGGAGTGTGAAGCCATTGTCCAG
TCTATCATTCATATCCGGACCCGCTGGGAACTGTCACAGCCCGACTCTATCCCCAACACACCAAGATTC
GGCCAAAAGATGTCCCTGGGACACTGCTCAATATCGCATTACTTAATTTAGGCAGTTCTGACCCGAGTTT
ACGGTCAGCTGCCTATAATCTTCTGTGTGCCTTAACTTGTACCTTTAATTTAAAAATCGAGGGCCAGTTA
CTAGAGACATCAGGTTTATGTATCCCTGCCAACAACACCCTCTTTATTGTCTCTATTAGTAAGCACTGG
CAGCCAATGAGCCACACCTCACGTTAGAATTTTTGGAAGAGTGTATTTCTGGATTTAGCAAATCTAGTAT
```

TABLE 31-continued

NF1 variant (lacking exon 8) Nucleotide Sequence
(8444 nt, SEQ ID No. 76)

TGAATTGAAACACCTTTGTTTGGAATACATGACTCCATGGCTGTCAAATCTAGTTCGTTTTTGCAAGCAT

AATGATGATGCCAAACGACAAAGAGTTACTGCTATTCTTGACAAGCTGATAACAATGACCATCAATGAAA

AACAGATGTACCCATCTATTCAAGCAAAAATATGGGGAAGCCTTGGGCAGATTACAGATCTGCTTGATGT

TGTACTAGACAGTTTCATCAAAACCAGTGCAACAGGTGGCTTGGGATCAATAAAAGCTGAGGTGATGGCA

GATACTGCTGTAGCTTTGGCTTCTGGAAATGTGAAATTGGTTTCAAGCAAGGTTATTGGAAGGATGTGCA

AAATAATTGACAAGACATGCTTATCTCCAACTCCTACTTTAGAACAACATCTTATGTGGGATGATATTGC

TATTTTAGCACGCTACATGCTGATGCTGTCCTTCAACAATTCCCTTGATGTGGCAGCTCATCTTCCCTAC

CTCTTCCACGTTGTTACTTTCTTAGTAGCCACAGGTCCGCTCTCCCTTAGAGCTTCCACACATGGACTGG

TCATTAATATCATTCACTCTCTGTGTACTTGTTCACAGCTTCATTTTAGTGAAGAGACCAAGCAAGTTTT

GAGACTCAGTCTGACAGAGTTCTCATTACCCAAATTTTACTTGCTGTTTGGCATTAGCAAAGTCAAGTCA

GCTGCTGTCATTGCCTTCCGTTCCAGTTACCGGGACAGGTCATTCTCTCCTGGCTCCTATGAGAGAGAGA

CTTTTGCTTTGACATCCTTGGAAACAGTCACAGAAGCTTTGTTGGAGATCATGGAGGCATGCATGAGAGA

TATTCCAACGTGCAAGTGGCTGGACCAGTGGACAGAACTAGCTCAAAGATTTGCATTCCAATATAATCCA

TCCCTGCAACCAAGAGCTCTTGTTGTCTTTGGGTGTATTAGCAAACGAGTGTCTCATGGGCAGATAAAGC

AGATAATCCGTATTCTTAGCAAGGCACTTGAGAGTTGCTTAAAAGGACCTGACACTTACAACAGTCAAGT

TCTGATAGAAGCTACAGTAATAGCACTAACCAAATTACAGCCACTTCTTAATAAGGACTCGCCTCTGCAC

AAAGCCCTCTTTTGGGTAGCTGTGGCTGTGCTGCAGCTTGATGAGGTCAACTTGTATTCAGCAGGTACCG

CACTTCTTGAACAAAACCTGCATACTTTAGATAGTCTCCGTATATTCAATGACAAGAGTCCAGAGGAAGT

ATTTATGGCAATCCGGAATCCTCTGGAGTGGCACTGCAAGCAAATGGATCATTTTGTTGGACTCAATTTC

AACTCTAACTTTAACTTTGCATTGGTTGGACACCTTTTAAAAGGGTACAGGCATCCTTCACCTGCTATTG

TTGCAAGAACAGTCAGAATTTTACATACACTACTAACTCTGGTTAACAAACACAGAAATTGTGACAAATT

TGAAGTGAATACACAGAGCGTGGCCTACTTAGCAGCTTTACTTACAGTGTCTGAAGAAGTTCGAAGTCGC

TGCAGCCTAAAACATAGAAAGTCACTTCTTCTTACTGATATTTCAATGGAAAATGTTCCTATGGATACAT

ATCCCATTCATCATGGTGACCCTTCCTATAGGACACTAAAGGAGACTCAGCCATGGTCCTCTCCCAAGG

TTCTGAAGGATACCTTGCAGCCACCTATCCAACTGTCGGCCAGACCAGTCCCCGAGCCAGGAAATCCATG

AGCCTGGACATGGGGCAACCTTCTCAGGCCAACACTAAGAAGTTGCTTGGAACAAGGAAAAGTTTTGATC

ACTTGATATCAGACACAAAGGCTCCTAAAAGGCAAGAAATGGAATCAGGGATCACAACACCCCCCAAAAT

GAGGAGAGTAGCAGAAACTGATTATGAAATGGAAACTCAGAGGATTTCCTCATCACAACAGCACCCACAT

TTACGTAAAGTTTCAGTGTCTGAATCAAATGTTCTCTTGGATGAAGAAGTACTTACTGATCCGAAGATCC

AGGCGCTGCTTCTTACTGTTCTAGCTACACTGGTAAAATATACCACAGATGAGTTTGATCAACGAATTCT

TTATGAATACTTAGCAGAGGCCAGTGTTGTGTTTCCCAAAGTCTTTCCTGTTGTGCATAATTTGTTGGAC

TCTAAGATCAACACCCTGTTATCATTGTGCCAAGATCCAAATTTGTTAAATCCAATCCATGGAATTGTGC

AGAGTGTGGTGTACCATGAAGAATCCCCACCACAATACCAAACATCTTACCTGCAAAGTTTTGGTTTTAA

TGGCTTGTGGCGGTTTGCAGGACCGTTTTCAAAGCAAACACAAATTCCAGACTATGCTGAGCTTATTGTT

AAGTTTCTTGATGCCTTGATTGACACGTACCTGCCTGGAATTGATGAAGAAACCAGTGAAGAATCCCTCC

TABLE 31-continued

NF1 variant (lacking exon 8) Nucleotide Sequence (8444 nt, SEQ ID No. 76)

TGACTCCCACATCTCCTTACCCTCCTGCACTGCAGAGCCAGCTTAGTATCACTGCCAACCTTAACCTTTC

TAATTCCATGACCTCACTTGCAACTTCCCAGCATTCCCCAGGAATCGACAAGGAGAACGTTGAACTCTCC

CCTACCACTGGCCACTGTAACAGTGGACGAACTCGCCACGGATCCGCAAGCCAAGTGCAGAAGCAAAGAA

GCGCTGGCAGTTTCAAACGTAATAGCATTAAGAAGATCGTGTGA (Double underline indicates bases bordering the splice junction)

TABLE 32

Primer across the junction between NF1 exon 7 and 9

Primer across the junction between NF1 exon 7 and 9 (SEQ ID No. 75)    GCCTGGAAAAGAATGTGCAGA (Double underline indicates bases bordering the splice junction)

TABLE 33 siRNA for selectively knockdown NF1 full length and variants expression siRNA targeting NF1 exon 8

Sense (SEQ ID No. 73) 5' CCAGAUCCCACAGACUGAUdTdT 3'

Antisense (SEQ ID No. 74) 3' dTdTGGUCUAGGGUGUCUGA-CUA (5'-P)5' siRNA targeting splice junction between NF1 exon 7 and exon 9

Sense (SEQ ID No. 77) 5' GGAAAAGAAUGUGCAGAAAdTdT 3'

Antisense (SEQ ID No. 78) 3' dTdTCCUUUUCUUACACGUC-UUU(5'-P)5'

(Double underline indicates bases bordering the splice junction)

TABLE 34

BAK1 (full length)Nucleotide Sequence (636 nt, SEQ ID No. 79)

ATGGCTTCGGGGCAAGGCCCAGGTCCTCCCAGGCAGGAGTGCGGAGAGCC

TGCCCTGCCCTCTGCTTCTGAGGAGCAGGTAGCCCAGGACACAGAGGAGG

TTTTCCGCAGCTACGTTTTTTACCGCCATCAGCAGGAACAGGAGGCTGAA

GGGGTGGCTGCCCCTGCCGACCCAGAGATGGTCACCTTACCTCTGCAACC

TAGCAGCACCATGGGGCAGGTGGGACGGCAGCTCGCCATCATCGGGGACG

ACATCAACCGACGCTATGACTCAGAGTTCCAGACCATGTTGCAGCACCTG

CAGCCCACGGCAGAGAATGCCTATGAGTACTTCACCAAGATTGCCACCAG

CCTGTTTGAGAGTGGCATCAATTGGGGCCGTGTGGTGGCTCTTCTGGGCT

TCGGCTACCGTCTGGCCCTACACGTCTACCAGCATGGCCTGACTGGCTTC

CTAGGCCAGGTGACCCGCTTCGTGGTCGACTTCATGCTGCATCACTGCAT

TGCCCGGTGGATTGCACAGAGGGGTGGCTGGGTGGCAGCCCTGAACTTGG

BAK1 (full length)Nucleotide Sequence (636 nt, SEQ ID No. 79)

GCAATGGTCCCATCCTGAACGTGCTGGTGGTTCTGGGTGTGGTTCTGTTG

GGCCAGTTTGTGGTACGAAGATTCTTCAAATCATGA (Exon 2 is indicated as double underline.)

TABLE 35

BAK1 variant (lacking exon 2) Nucleotide Sequence (501 nt, SEQ ID No. 85).

ATGGCTTCGGGGCAAGGCCCAGGTCCTCCCAGGCAGGAGTGCGGAGAGCC

TGCCCTGCCCTCTGCTTCTGGCACCATGGGGCAGGTGGGACGGCAGCTCG

CCATCATCGGGGACGACATCAACCGACGCTATGACTCAGAGTTCCAGACC

ATGTTGCAGCACCTGCAGCCCACGGCAGAGAATGCCTATGAGTACTTCAC

CAAGATTGCCACCAGCCTGTTTGAGAGTGGCATCAATTGGGGCCGTGTGG

TGGCTCTTCTGGGCTTCGGCTACCGTCTGGCCCTACACGTCTACCAGCAT

GGCCTGACTGGCTTCCTAGGCCAGGTGACCCGCTTCGTGGTCGACTTCAT

GCTGCATCACTGCATTGCCCGGTGGATTGCACAGAGGGGTGGCTGGGTGG

CAGCCCTGAACTTGGGCAATGGTCCCATCCTGAACGTGCTGGTGGTTCTG

GGTGTGGTTCTGTTGGGCCAGTTTGTGGTACGAAGATTCTTCAAATCATG

A (Double underline indicates bases bordering the splice junction)

TABLE 36

Primer across the junction between BAK1 exon 7 and 9

Primer across the junction between BAK1 exon 1 and 3 (SEQ ID No. 84)    TCTGCTTCTGGCACCATGGG (Double underline indicates bases bordering the splice junction)

TABLE 37 siRNA for selectively knockdown BAK1 full length and variants expression siRNA targeting exon 2

Sense (SEQ ID No. 82) 5' GGUCACCUUACCUCUGCAAdTdT 3'

TABLE 37-continued siRNA for selectively knockdown BAK1
full length and variants expression Antisense (SEQ ID No. 83) 3' dTdTCCAGUGGAAUGGAGAC-GUU(5'-P)5' siRNA targeting splice junction between
exon 1 and exon 3

Sense (SEQ ID No. 86) 5' CCCUCUGCUUCUGGCACCAdTdT 3'

Antisense (SEQ ID No. 87) 3' dTdTGGGAGACGAAGACCGU-GGU (5'-P)5'

(Double underline indicates bases bordering the splice junction)

Methods of Detection

The present invention provides a method of identifying splicing variants of genes associated with prostate cancer risk and survival. The method generally comprises detecting the splicing variants in a nucleic acid sample from an individual, such as a prostate biopsy specimen. Typically, total RNA is extracted from the specimen, cDNA is synthesized from the extracted RNA and subject to further analysis. Nucleic acid samples used in the methods and assays of the present invention may be prepared by any available method or process.

Detection of splicing variants may be accomplished by amplifying specific fragments directly from a cDNA preparation from the tumor tissue using PCR. Presence of certain PCR product can be indicative of the presence of certain splicing variants, when the primers for the PCR are designed in such way that PCR products are only available when certain variants are present in the sample. Alternatively, primers may be designed to produce easily differentiable products for different variants. The sequence composition of the variants may also be determined from the amplified product.

The PCR reaction is well known in the art (See, e.g., U.S. Pat. No. 4,683,203; and U.S. Pat. No. 4,683,195). In general, the PCR procedure describes a method of gene amplification which is comprised of (i) sequence-specific hybridization of primers to specific genes within a DNA sample (or library), (ii) subsequent amplification involving multiple rounds of annealing, elongation, and denaturation using a DNA polymerase, and (iii) screening the PCR products for a band of the correct size. The primers used are oligonucleotides of sufficient length and appropriate sequence to provide initiation of polymerization, i.e. each primer is specifically designed to be complementary to each strand of the genomic locus to be amplified. The primers are prepared using any suitable method, such as conventional phosphotriester or phosphodiester methods or automated embodiments thereof (Beaucage, *Tet. Lett.* 22:1859-1862, 1981).

For the detection of splicing variants, primers may be designed to flank a certain exon that may be alternatively spliced, i.e., one primer is complementary to the 5' side of the exon, and the other primer is complementary to the 3' side of the exon. The PCR amplification products thus would show different sizes. When the exon is present, a larger amplification product is obtained. When the exon is absent, a smaller amplification product is obtained. Alternatively, a primer may be designed to be complementary to a nucleotide sequence within the exon. This way, PCR amplification product is only available when the exon is present in the specimen. Additionally, a primer may be designed to be partially complementary to the 3' end of an exon 5' to the alternatively spliced exon, and partially complementary to the 5' end of an exon 3' to the alternatively spliced exon. PCR amplification product can only be obtained when the alternatively spliced exon is present in the sample.

The polymerization agent can be any compound or system (including enzymes) which will facilitate combination of the nucleotides in the proper manner to form the primer extension products which are complementary to each nucleic acid strand. Other fundamental conditions to allow amplification include the presence of nucleoside triphosphates and suitable temperature and pH (Thigpen et al., *J. Clin. Invest.* 90: 799-809, 1992; Saiki et al., *Science* 239: 487-491, 1988).

DNA sequences of the specified gene which have been amplified by use of polymerase chain reaction may also be screened using exon oligonucleotide probes. These probes are nucleic acid oligomers, each of which are complementary to a corresponding segment of the investigated gene and may or may not contain a known variant. The assay is performed by detecting the presence or absence of a hybridization signal for the specific sequence.

Oligonucleotide Probes

Another aspect of the subject invention is to provide for variant specific nucleic acid hybridization probes capable of detecting splicing variants of genes which predispose an individual to prostate cancer. The hybridization probes of the subject invention may be derived from the disclosed nucleotide sequences of the identified variants and form stable hybrids with the target sequences, under stringent to moderately stringent hybridization and wash conditions. Stringent conditions will be used in the case of perfect complementation with the target sequence, less stringent hybridization conditions will be used if mismatches are expected among the variants. Conditions will always be chosen such that nonspecific/adventitious bindings are eliminated or minimized. The probes may be of any suitable length, which span all or a portion of the specified gene region, and which allow specific hybridization.

Nucleic acid hybridization simply involves contacting a probe and target nucleic acid (from a nucleic acid sample) under conditions where the probe and its complementary target can form stable hybrid duplexes through complementary base pairing (see U.S. Pat. No. 6,333,155). Methods of nucleic acid hybridization are well known in the art. In a preferred embodiment, the probes are immobilized on solid supports such as beads, microarrays, or gene chips.

The probes include an isolated polynucleotide, preferably attached to a label or reporter molecule, may be used to isolate other polynucleotide sequences, having sequence similarity by standard methods. Techniques for preparing and labeling probes are known in the art and disclosed in Sambrook et al. (Molecular Cloning: A Laboratory Manual, Ed. 2; Cold Spring Harbor, N.Y.: Cold Spring Harbor Laboratory, 1989) or Ausubel et al. (Current Protocols in Molecular Biology, Wiley & Sons, New York, N.Y., 1995). The labels may be incorporated by any of a number of means well known to those of skill in the art (see U.S. Pat. No. 6,333,155). Commonly employed labels include, but are not limited to, biotin, fluorescent molecules, radioactive molecules, chromogenic substrates, chemiluminescent labels, enzymes, and the like. The methods for biotinylating nucleic acids are well known in the art, as are methods for introducing fluorescent molecules and radioactive molecules into oligonucleotides and nucleotides.

Other similar polynucleotides may be selected by using homologous polynucleotides. Alternatively, polynucleotides encoding these or similar polypeptides may be synthesized or selected by use of the redundancy in the genetic code. Various codon substitutions may be introduced, e.g., by silent changes (thereby producing various restriction sites) or to optimize expression for a particular system. Mutations may be introduced to modify the properties of the polypeptide, perhaps to change ligand-binding affinities, interchain affinities, or the polypeptide degradation or turnover rate.

Probes comprising synthetic oligonucleotides or other polynucleotides of the present invention may be derived from naturally occurring or recombinant single- or double-stranded polynucleotides, or be chemically synthesized. Probes may also be labeled by nick translation, Klenow fill-in reaction, or other methods known in the art.

Other means for producing specific hybridization probes for nucleic acids include the cloning of nucleic acid sequences into vectors for the production of mRNA probes. Such vectors are known in the art and are commercially available and may be used to synthesize RNA probes in vitro by means of the addition of the appropriate RNA polymerase as T7 or SP6 RNA polymerase and the appropriate radioactively labeled nucleotides.

The nucleotide sequences may be used to construct hybridization probes for mapping their respective genomic sequences. The nucleotide sequence provided herein may be mapped to a chromosome or specific regions of a chromosome using well known genetic and/or chromosomal mapping techniques. These techniques include in situ hybridization, linkage analysis against known chromosomal markers, hybridization screening with libraries or flow-sorted chromosomal preparations specific to known chromosomes, and the like (Verma et al., Human Chromosomes: A Manual of Basic Techniques, Pergamon Press, New York N.Y., 1988).

To detect the presence of the splicing variants of genes predisposing an individual to prostate cancer, a test sample is prepared and analyzed for the presence or absence of such susceptibility alleles. Thus, the present invention provides methods to identify the expression of one of the nucleic acids of the present invention, or homolog thereof, in a test sample, using a nucleic acid probe or antibodies of the present invention. In particular, such methods comprise incubating a test sample with one or more of oligonucleotide probes of the present invention (as described above) and assaying for binding of the nucleic acid probes or antibodies to components within the test sample.

Conditions for incubating a nucleic acid probe or antibody with a test sample depend on the format employed in the assay, the detection methods used, and the type and nature of the probe used in the assay. One skilled in the art will recognize that any one of the commonly available hybridization or amplification formats can readily be adapted to employ the nucleic acid probes or antibodies of the present invention. Examples of such assays can be found in Chard, An Introduction to Radioimmunoassay and Related Techniques, Elsevier Science Publishers, Amsterdam, Netherlands, 1986; Bullock et al., Techniques in Immunocytochemistry, Academic Press, Orlando, Fla. Vol. 1, 1982, Vol. 2, 1983, Vol. 3, 1985; Tijssen, Practice and Theory of Immunoassays: Laboratory Techniques in Biochemistry and Molecular Biology, Elsevier Science Publishers, Amsterdam, Netherlands, 1985.

The test samples of the present invention include cells, protein or membrane extracts of cells, or biological fluids such as sputum, blood, serum, plasma, or urine. The test sample used in the above-described method will vary based on the assay format, nature of the detection method and the tissues, cells or extracts used as the sample to be assayed. Methods for preparing DNA extracts from any of the above samples are well known in the art and can be readily be adapted in order to obtain a sample which is compatible with the system utilized.

Gene Silencing

The phrase "gene silencing" refers to a process by which the expression of a specific gene product is lessened or attenuated. It is also used interchangeably with the term "gene knockdown." Gene silencing can take place by a variety of pathways. Unless specified otherwise, as used herein, gene silencing refers to decreases in gene product expression that results from RNA interference (RNAi), a defined, though partially characterized pathway whereby small inhibitory RNA (siRNA) act in concert with host proteins (e.g. the RNA induced silencing complex, RISC) to degrade messenger RNA (mRNA) in a sequence-dependent fashion. The level of gene silencing can be measured by a variety of means, including, but not limited to, measurement of transcript levels by Northern Blot Analysis, B-DNA techniques, transcription-sensitive reporter constructs, expression profiling (e.g. DNA chips), and related technologies. Alternatively, the level of silencing can be measured by assessing the level of the protein encoded by a specific gene. This can be accomplished by performing a number of studies including Western Analysis, measuring the levels of expression of a reporter protein that has e.g. fluorescent properties (e.g. GFP) or enzymatic activity (e.g. alkaline phosphatases), or several other procedures.

The term "siRNA" refers to small inhibitory RNA duplexes that induce the RNA interference (RNAi) pathway. These molecules can vary in length (generally between 18-30 basepairs) and contain varying degrees of complementation to their target mRNA in the antisense strand. Some, but not all, siRNAs have unpaired overhanging bases on the 5' or 3' end of the sense strand and/or the antisense strand. The term "siRNA" includes duplexes of two separate strands, as well as single strands that can form hairpin structures comprising a duplex region. Designing a siRNA molecule that can specifically silence a certain gene is well known in the art, and can be routinely carried out using methods similar to what is disclosed in U.S. Pat. No. 8,008,474, which is incorporated herein by reference. siRNA can be routinely introduced to cells through conventional means such as transfection.

For targeted silencing of certain splicing variant, siRNA can be designed to target a specific exon that is only present in one variant. The mRNA of the variant that include this exon will be selectively silenced. Alternatively, siRNA can be designed to target a specific exon junction, which will only exist when certain splicing event occurs. In other words, siRNA can be designed to target the junction sequence of an exon immediately 5' to the alternatively spliced exon and an exon that is immediately 3' to the alternatively spliced exon. This particular junction sequence would only exist in a continuous polynucleotide sequence within an mRNA when the alternatively spliced exon is lacking.

What is claimed is:

1. An siRNA molecule characterized by a length of 15 to 31 nucleotides and that inhibits expression of PIK3CD and/or splicing variants thereof comprising:
   a) a duplex region comprising a sense region and an antisense region, wherein the sense and antisense regions of the duplex region each consist of 15-31 nucleotides and wherein the sense region includes a PIK3CD variant splice junction and is homologous with at least 15 nucleotides of SEQ ID No. 12; and
   b) an overhang region of 0-6 nucleotides.

2. The siRNA molecule of claim 1, wherein the antisense region is complementary to SEQ ID No. 12.

3. The siRNA molecule of claim 1, wherein the overhang region is 2 nucleotides in length.

4. The siRNA molecule of claim 1, wherein the siRNA molecule has no overhang region.

5. The siRNA molecule of claim 1, wherein the siRNA molecule is chemically synthesized.

6. An siRNA molecule that inhibits expression of PIK3CD and/or splicing variants of, wherein the siRNA is characterized by a length of 15 to 31 nucleotides, includes a PIK3CD variant splice junction, and is homologous with at least 15 nucleotides of SEQ ID No. 12.

7. The siRNA molecule of claim 6, comprises an overhang region of 0-6 nucleotides.

8. The siRNA molecule of claim 6 wherein the siRNA molecule is a single stranded molecule that can form hairpin structures comprising a duplex region.

* * * * *

UNITED STATES PATENT AND TRADEMARK OFFICE
CERTIFICATE OF CORRECTION

PATENT NO. : 9,453,261 B2
APPLICATION NO. : 14/344509
DATED : September 27, 2016
INVENTOR(S) : Norman H. Lee et al.

Page 1 of 3

It is certified that error appears in the above-identified patent and that said Letters Patent is hereby corrected as shown below:

In the Drawings

Figure 3A, change "Exon 10" to --Exon 8--; and

Figure 3A, change "Exon 23" to --Exon 20--;

Figure 4, change "  "

to -- 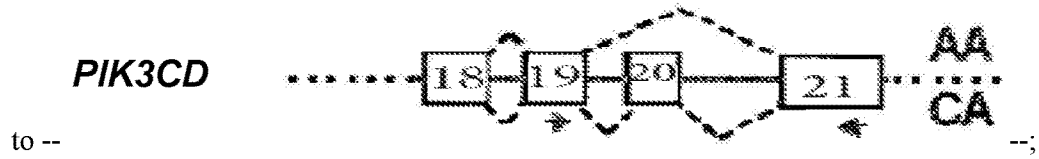 --;

Figure 7, change

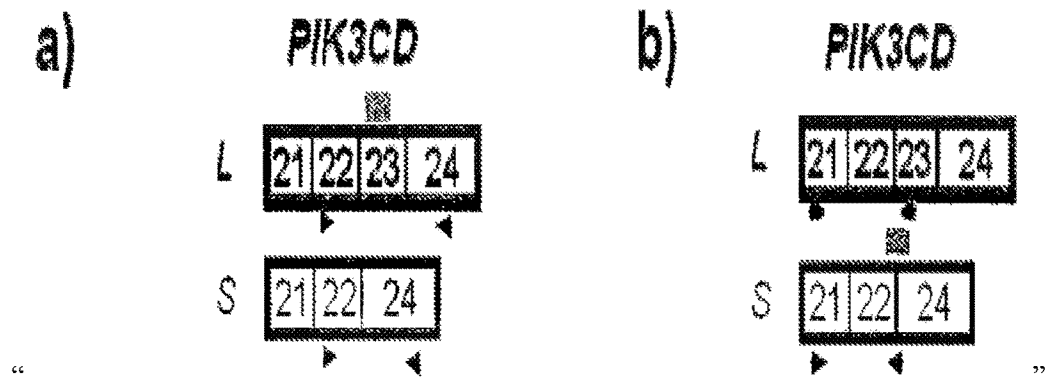

" "

Signed and Sealed this
Twentieth Day of November, 2018

Andrei Iancu
*Director of the United States Patent and Trademark Office*

CERTIFICATE OF CORRECTION (continued)
U.S. Pat. No. 9,453,261 B2

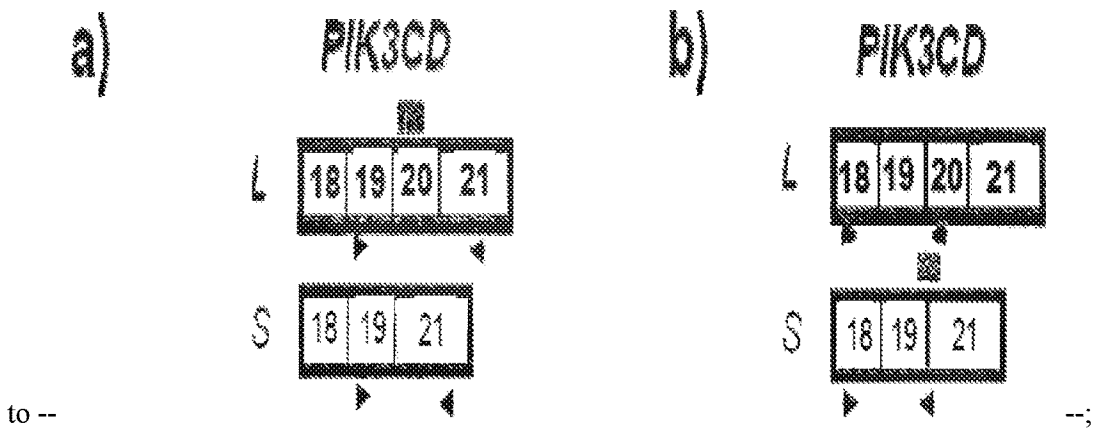

to --                                                                                   --;

In the Specification

At Column 4, Line number 67, change "lack exons 10 and 23," to --lack exons 8 and 20,--;

At Column 7, Line number 4, change "Exon 23" to --Exon 20--;

At Column 7, Line number 16, change "exon 10" to --exon 8--;

At Column 7, Line number 17, change "nt2430-2592" to --nt931-1020--;

At Column 7, Line number 19, change "variant 2 lacks exon 23" to --variant 2 lacks exon 20--;

At Column 7, Line number 20, change "nt931-1020), variant 3 lacks both exon 10 and 23" to --nt2427-2594), variant 3 lacks both exon 8 and 20--;

At Column 7, Line number 21, change "nt2430-2592)," to --nt2427-2594),--;

At Column 7, Line number 24, change "Exon 10 and exon 23" to --Exon 8 and exon 20--;

At Column 7, Line number 32, change "23," to --20--;

At Column 11, Table 2, change "(Exon 10" to --(Exon 8--;

At Column 11, Table 2, change "Exon 23" to --Exon 20--;

At Column 11, Table 3, change "exon 10)" to --exon 8)--;

At Column 13, Table 3-continued, change "exon 10)" to --exon 8)--;

At Column 13, Table 4, change "exon 23)" to --exon 20)--;

At Column 15, Table 4-continued, change "exon 23)" to --exon 20)--;

CERTIFICATE OF CORRECTION (continued)
U.S. Pat. No. 9,453,261 B2

At Column 15, Table 5, change "exon 10 and exon 23" to --exon 8 and exon 20--;

At Column 17, Table 5-continued, change "exon 10 and exon 23" to --exon 8 and exon 20--;

At Column 19, Table 7, change "exon 9 and 11" to --exon 7 and 9--;

At Column 19, Table 7, change "22 and 24" to --19 and 21--;

At Column 20, Table 8, change "exon 23" to --exon 20--;

At Column 20, Table 8, change "exon 9 and exon 11" to --exon 7 and exon 9--;

At Column 21, Table 8-continued, change "exon 22 and exon 24" to --exon 19 and exon 21--;

At Column 71, <223> of SEQ ID NO4, change "PI3KCD exon 23" to --PI3KCD exon 20--; and At Column 71, <223> of SEQ ID NO 5, change "targeting exon 23" to --targeting exon 20--.